(12) United States Patent
Blomquist

(10) Patent No.: US 8,823,528 B2
(45) Date of Patent: *Sep. 2, 2014

(54) INFUSION PUMP HAVING AN ALARM SIGNAL

(75) Inventor: Michael L. Blomquist, Blaine, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/481,091

(22) Filed: May 25, 2012

(65) Prior Publication Data

US 2012/0293328 A1 Nov. 22, 2012

Related U.S. Application Data

(63) Continuation of application No. 10/087,449, filed on Feb. 28, 2002, now Pat. No. 8,504,179.

(51) Int. Cl.
*G08B 23/00* (2006.01)
*G06F 19/00* (2011.01)
*A61M 5/142* (2006.01)

(52) U.S. Cl.
CPC ..... *A61M 5/142* (2013.01); *A61M 2005/14208* (2013.01); *G06F 19/3468* (2013.01); *G06F 19/3412* (2013.01); *A61M 2205/3553* (2013.01)
USPC .............. 340/573.1; 340/309.16; 340/539.12; 604/504

(58) Field of Classification Search
USPC .......... 340/573.1, 539.12, 309.16; 604/890.1, 604/504, 65–67, 151
See application file for complete search history.

(56) References Cited

U.S. PATENT DOCUMENTS

| | | |
|---|---|---|
| 4,151,845 A | 5/1979 | Clemens |
| 4,308,866 A | 1/1982 | Jelliffe et al. |
| 4,435,173 A | 3/1984 | Siposs |
| 4,457,751 A | 7/1984 | Rodler |
| 4,469,481 A | 9/1984 | Kobayashi |
| 4,529,401 A | 7/1985 | Leslie et al. |
| 4,776,842 A | 10/1988 | Franetzki et al. |
| 5,097,429 A | 3/1992 | Wood et al. |
| 5,190,522 A | 3/1993 | Wojcicki et al. |
| 5,713,856 A | 2/1998 | Eggers |
| 5,752,235 A | 5/1998 | Kehr et al. |
| 5,805,051 A | 9/1998 | Herrmann et al. |
| 5,997,475 A | 12/1999 | Bortz |
| 6,107,911 A | 8/2000 | Perrone |
| 6,167,362 A | 12/2000 | Brown et al. |
| 6,198,383 B1 | 3/2001 | Sekura et al. |
| 6,379,301 B1 | 4/2002 | Worthington et al. |

(Continued)

OTHER PUBLICATIONS

Application and File history for U.S. Appl. No. 10/087,460, filed Feb. 28, 2002. Inventor: Michael L. Blomquist.

(Continued)

*Primary Examiner* — Thomas Mullen
(74) *Attorney, Agent, or Firm* — Patterson Thuente Pedersen, P.A.

(57) ABSTRACT

A pump for delivering insulin to a user comprises a pump mechanism, an alarm and a timer and an alarm program in data communication with the alarm and the timer. The alarm program module is programmed to operate a plurality of types of alerts and to associate a predetermined interval of time and a predetermined event with a selected type of alert. An alarm signal can be generated by the alarm program module based on the predetermined event and interval.

26 Claims, 34 Drawing Sheets

(56) References Cited

U.S. PATENT DOCUMENTS

| | | | |
|---|---|---|---|
| 6,408,854 B1 | 6/2002 | Gonda et al. |
| 6,427,088 B1 | 7/2002 | Bowman et al. |
| 6,485,461 B1 | 11/2002 | Mason et al. |
| 6,551,276 B1 | 4/2003 | Mann et al. |
| 6,554,798 B1 | 4/2003 | Mann |
| 6,641,562 B1 | 11/2003 | Peterson |
| 6,650,951 B1 | 11/2003 | Jones |
| 6,744,350 B2 | 6/2004 | Blomquist |
| 6,852,104 B2 | 2/2005 | Blomquist |
| 6,999,854 B2 | 2/2006 | Roth |
| 7,033,338 B2 | 4/2006 | Vilks et al. |
| 8,250,483 B2 | 8/2012 | Blomquist |
| 8,346,399 B2 | 1/2013 | Blomquist |
| 2002/0046073 A1 | 4/2002 | Indseth |
| 2002/0107476 A1 | 8/2002 | Mann et al. |
| 2002/0193679 A1 | 12/2002 | Malave |
| 2003/0114836 A1 | 6/2003 | Estes |
| 2003/0160683 A1 | 8/2003 | Blomquist |
| 2003/0163088 A1 | 8/2003 | Blomquist |
| 2003/0176933 A1 | 9/2003 | Lebel et al. |
| 2003/0181851 A1 | 9/2003 | Mann et al. |
| 2003/0187525 A1 | 10/2003 | Mann et al. |
| 2003/0191431 A1 | 10/2003 | Mann et al. |
| 2003/0195462 A1 | 10/2003 | Mann et al. |
| 2004/0073329 A1 | 4/2004 | Engleson et al. |
| 2005/0030164 A1 | 2/2005 | Blomquist |
| 2006/0132292 A1 | 6/2006 | Blomquist |
| 2012/0191062 A1 | 7/2012 | Blomquist |
| 2012/0232484 A1 | 9/2012 | Blomquist |
| 2012/0232485 A1 | 9/2012 | Blomquist |
| 2012/0232486 A1 | 9/2012 | Blomquist |
| 2012/0232521 A1 | 9/2012 | Blomquist |
| 2012/0239362 A1 | 9/2012 | Blomquist |
| 2012/0296269 A1 | 11/2012 | Blomquist |
| 2012/0296310 A1 | 11/2012 | Blomquist |

OTHER PUBLICATIONS

Application and File history for U.S. Appl. No. 10/856,686, filed May 28, 2004. Inventor: Michael L. Blomquist.

Application and File history for U.S. Appl. No. 11/338,354, filed Dec. 28, 2007. Inventor: Michael L. Blomquist.

Delta, Inc. Received 510k Clearance for Insulin Pump; LogiMedix Press Release; Aug. 15, 2002. http://216.239.51.104/search?q=cache:-ZHPMXYdD5MJ:www.logimedix.com/pr20020815.htm+Deltec.

"Insulin Pumps" Diabetes Forecast, Jan. 2004.

"Insulin Pumps: Deltec Cozmo," Medical Express Depot. Apr. 19, 2004. http://216.239.51.104/search?q=cache:V_KngKBU6BQj:www.medicalexpressdepot.com/insulin-pumps.

"Children with Doabetes-Deltec Cozmo Chat," Apr. 19, 2004. http://216.239.51.104/search?q=cache:MxHBVd9_-RoJ:www.childrenwithdiabetes.com/chat/transcript/.

Application and File History for U.S. Appl. No. 09/596,648, filed Jun. 19, 2000, inventors Jones et al.

Application and File History for U.S. Appl. No. 13/481,050, filed May 25, 2012, inventor Blomquist.

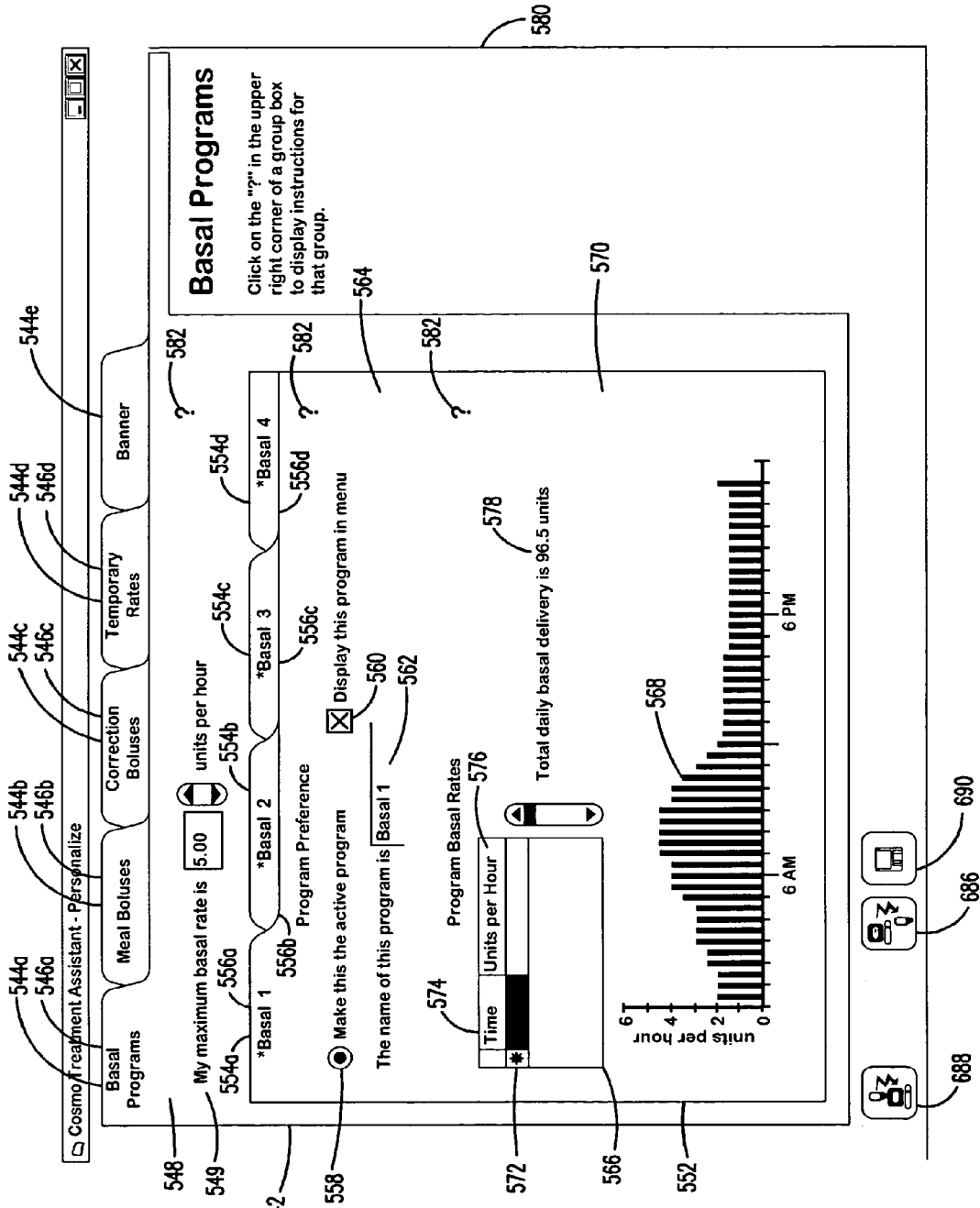

INFUSION PUMP HAVING AN ALARM SIGNAL

RELATED APPLICATION

This application is a continuation of application Ser. No. 10/087,449 filed Feb. 28, 2002, now U.S. Pat. No. 8,504,179, which is hereby fully incorporated herein by reference.

TECHNICAL FIELD

The present invention relates to insulin pumps, and more particularly, to insulin pumps having a missed meal bolus alarm.

BACKGROUND

A large portion of the world's population suffers from diabetes. Many of these people need to take injections of insulin to normalize the level of sugar in their bodies to prevent complications. Such complications can include kidney failure, loss of circulation, and blindness. The need to manually take injections with a syringe and the process of determining the dose for various shots can be a great inconvenience and can limit a diabetic's activities and restrict their movements. Furthermore, it can be difficult to maintain a consistent level of blood glucose because there is a practical limit to the number of injections that most patients can receive.

One solution to reduce some of the problems associated with the manual injection of insulin is an ambulatory pump that delivers insulin to the diabetic user. Such insulin pumps can provide a more consistently normal level of blood glucose, which reduces the risk of complications from diabetes. However, current pumps still have practical limits to their programming that make them cumbersome to program and that limits the potential of the pump to provide even greater control over blood glucose levels.

SUMMARY

One aspect of the present invention is a method of operating an insulin pump. The insulin pump is configured to selectively deliver a meal bolus. The method comprises entering into the pump a start time for an interval; entering into the pump an end time for the interval; and generating an alarm signal if a meal bolus is not delivered during the interval.

Another aspect of the present invention is a pump for delivering insulin to a user. The pump comprises a pump mechanism and a meal-bolus program module. The meal-bolus program module is programmed to control the pump mechanism to deliver a meal bolus. An alarm program module is in data communication with the alarm, the timer, and the meal-bolus program module. The alarm module is programmed to generate an alarm signal when the meal-bolus program module does not control the pump mechanism to deliver a meal bolus within a predetermined period of time.

DESCRIPTION OF THE DRAWINGS

FIGS. 30A-30E illustrate a user interface on the computer illustrated in FIG. 29.

DETAILED DESCRIPTION

Figure 1:
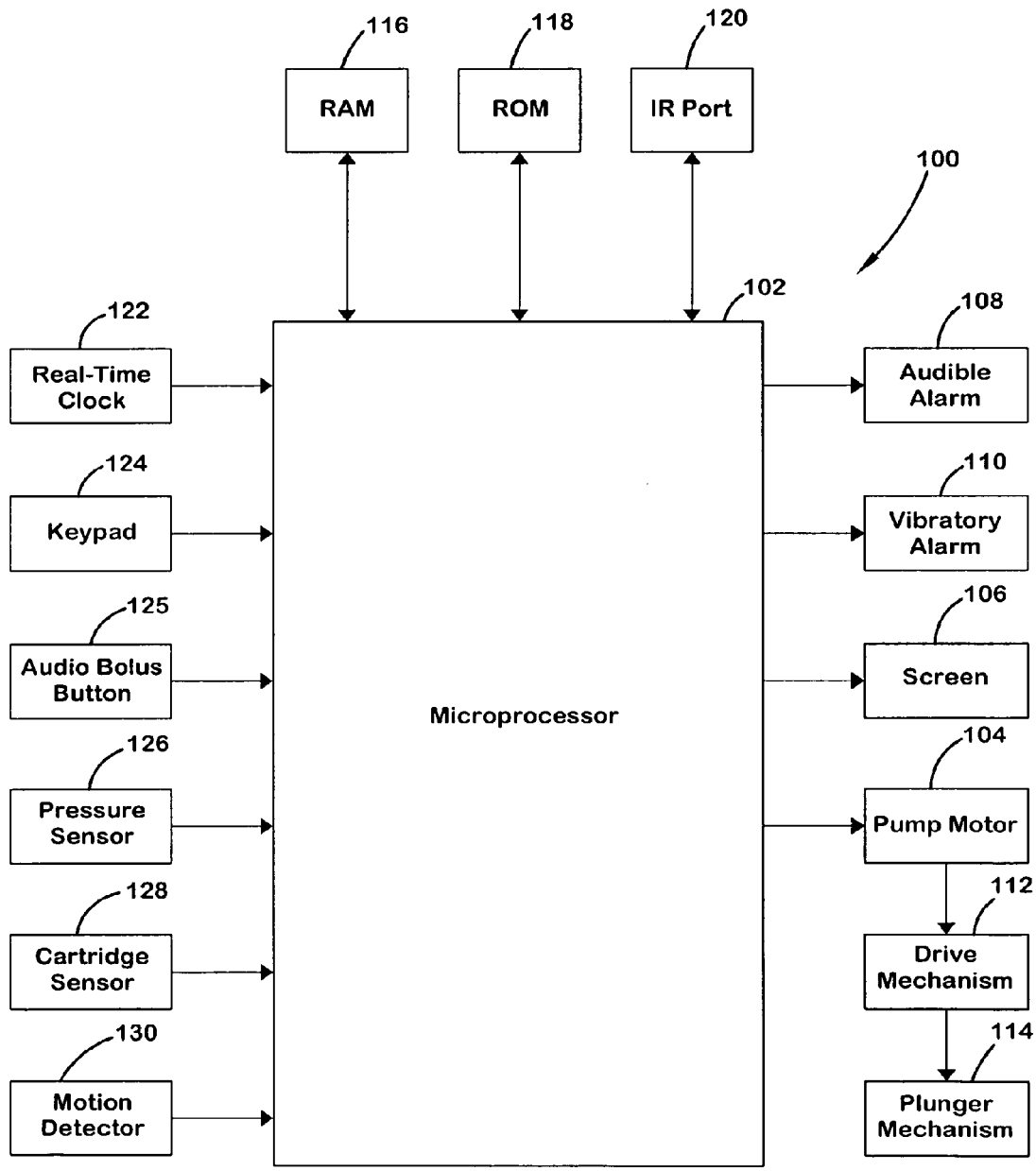
FIG. 1 illustrates the architecture of a pump that embodies the present invention.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

The logical operations of the various embodiments of the invention described herein are implemented as: (1) a sequence of computer implemented steps, operations, or procedures running on a programmable circuit within a computer, (2) a sequence of computer implemented steps, operations, or procedures running on a programmable circuit within a pump for delivering insulin; and/or (3) interconnected machine modules or program engines within the programmable circuits.

The various embodiments execute or utilize operating parameters, which customize or personalize operation of the computer implemented steps, machine modules, and programs to meet the requirements of individual pump users. The operating parameters can be numerical values, text strings, flags, argument names, or any other aspect of the insulin pump programming that the user can set to control operation of the pump.

Additionally, the pump generates and presents information and fields in user interfaces, which are also referred to as displays. The user interfaces can include fields, alpha/numeric character strings, times, and dates. The fields, also referred to as cells, prompt users to enter and/or select information. Because there is not an alpha/numeric keyboard on the pump, each of the field is associated with a spin box that includes values the user can enter into the field. The user spins or scrolls through values until the desired value is visible within the field. When the user selects the visible value it is entered into the field. The user selects a value with a Next function, Edit function, or Select function as identified herein. When the pump displays a field and the field has focus, it is said to prompt the user to select a value. Additionally, selecting a value in a field causes the pump to index focus to the next field as defined by the programmed operations or to display the next user interface as defined by the programmed operations. In an alternative embodiment, the pump has an alpha/numeric keyboard from which operating parameters can be typed directly into the pump.

The description set forth herein discusses pumping insulin. One skilled in the art will realize that many of the features, structures, and methods disclosed herein can be used with medical infusion pumps for delivering agents other than insulin. The term "user" generally applies to the person who is receiving insulin from the pump. In many contexts, however, the user could also refer to any other person such as a caregiver that is operating the pump.

A. Pump Architecture

FIG. 1 is a functional block diagram illustrating one of many possible embodiments of an insulin pump, generally identified as 100. A microprocessor 102 is in electrical communication with and controls a pump motor 104, a screen 106, an audible alarm 108, and a vibratory alarm 110. Other embodiments can use a microcomputer, or any other type of programmable circuit, in place of the microprocessor.

The pump motor 104 drives a drive mechanism 112 that pushes a plunger mechanism 114. The plunger mechanism 114 ejects insulin from an insulin cartridge (not shown). The insulin cartridge contains a supply of insulin for delivery to a patient. These mechanical components are illustrated and discussed in commonly assigned U.S. patent application Ser. No. 10/086,646, now U.S. Pat. No. 7,033,338, entitled Cartridge and Pump With Axial Loading, the disclosure of which was hereby incorporated by reference above.

The screen 106 can have many different configurations such as an LCD screen. As explained in more detail herein, the screen 106 displays a user interface that presents various items of information useful to a patient or caregiver. The audible alarm 108 is a beeper, and an alarm provides actual alarms, warnings, and reminders. Similar to other portable electronic devices such as a cellular telephone, the vibratory alarm 110 provides an alarm to either supplement the audio alarms or replace the audio alarm when an audible beep would be disruptive or not heard. A user can selectively enable or disable the audible 108 and vibratory 110 alarms. In one possible embodiment, however, both the audible 108 and vibratory 110 alarms cannot be disabled at the same time.

The microprocessor 102 is in electrical communication with both a random access memory (RAM) 116 and a read only memory (ROM) 118, which are onboard the pump 100 but external to the microprocessor 102 itself. In one possible embodiment, the microprocessor 102 includes internal memory as well. The RAM 116 is a static RAM that stores data that can change over time such as pump settings and a historical log of events experienced by the insulin pump 100. The ROM 118 stores code for the operating system and the application programs. The ROM 118 can be any type of programmable ROM such as an EPROM. In one possible embodiment, the RAM 116 has 500 kilobytes of memory capacity and the ROM 118 has 2 megabytes of memory capacity.

An infrared (IR) port 120 is in electrical communication with the microprocessor. As explained in more detail below, the IR port 120 provides data communication with an external device such as a computer for programming an application program, programming pump settings, and downloading historical data logs. The insulin pump 100 can include other types of communication ports in place of or in addition to the IR port 120. Examples of other possible communication ports include a radio frequency (RF) port or a port that provides a hard-wired data communication link such as an RS-232 port, a USB port, or the like.

A real-time clock 122 provides a clock signal to the microprocessor 102. An advantage of having a real-time clock 122 is that it provides the program with the actual time in real-time so that the programs executed by the insulin pump can track and control the actual time of day that insulin delivery and other events occur. Various durations described here are used for alerts, alarms, reminders, and other functions. In one possible embodiment, the timers are formed by the real-time clock 122 and software executed by the microprocessor 102.

A keypad 124 also provides input to the microprocessor 102. Although other possible types of keypads are possible, one type of keypad has four buttons and is a membrane-type of keypad, which provides resistance to water and other environmental conditions. The keypad 124 contains soft keys for which the function of the keys can change as a user executes different menu selections and commands.

Other inputs into the microprocessor 102 include a pressure sensor 126, which is sensitive to the pressure within a reservoir of insulin; a cartridge sensor 128, which is sensitive to the presence of an insulin cartridge; and a motion detector 130, which detects motion of a gear (not shown) in the drive mechanism 112. The pressure sensor 126, cartridge sensor 128, and motion detector 130 are described in more detail in U.S. patent application Ser. No. 10/086,646, now U.S. Pat. No. 7,033,338, which is entitled Cartridge and Pump With Axial Loading, the disclosure of which was incorporated by reference above.

Figure 2:
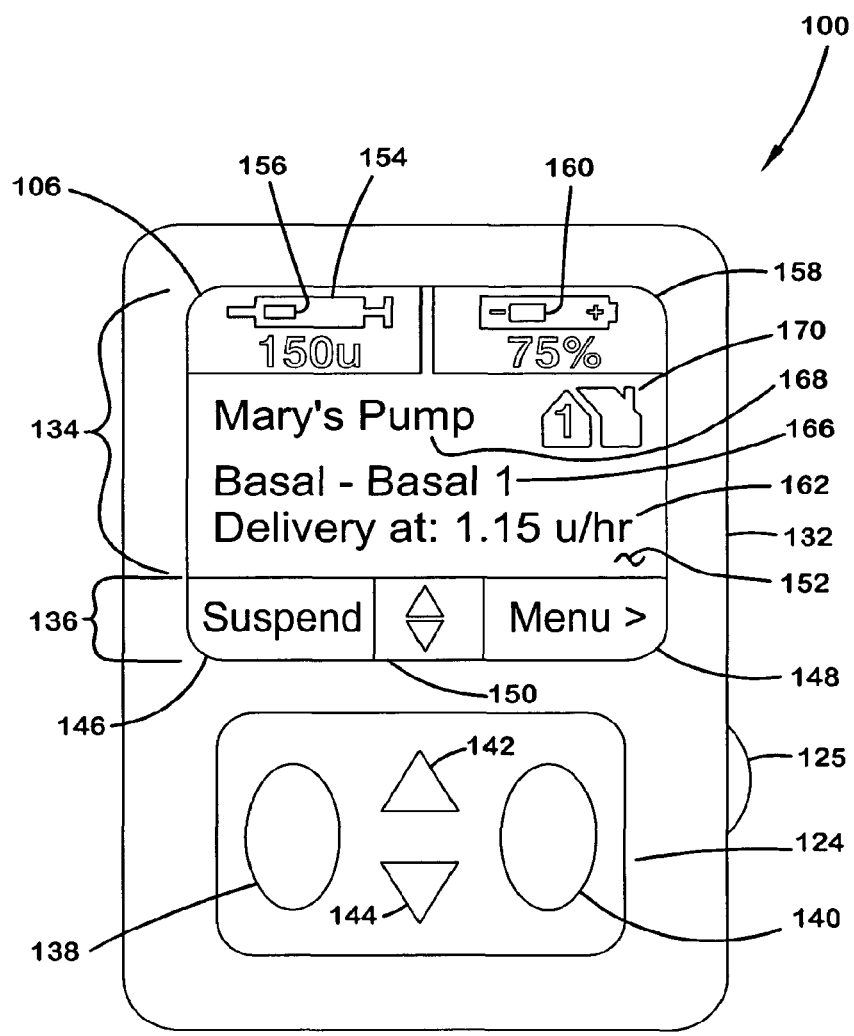
FIG. 2 is a top view of the pump shown in FIG. 1.

Referring to FIG. 2, the pump 100 is packaged in a housing 132. The keypad 124 is positioned on a first portion of the housing 132, and the screen 106 is positioned on a second portion of the housing 132. Additionally, the screen 106 has two portions, a display portion 134 and a template portion 136. A user interface is presented in the display portion 134 of the screen 106.

The template portion 136 provides a template that indicates the function assigned to each of the keys on the keypad. In the embodiment illustrated in the drawings, the keypad 124 has a first function key 138 and a second function key 140, and an up key 142 and a down key 144. The up and down keys 142 and 144 are for scrolling or spinning through operating parameters that are presented in a spin box associated with a field or between pages present within a user interface such as the home pages as described below. Additionally, a first portion 146 in the template identifies the function assigned to the first function key 138, and a second portion 148 identifies the function assigned to the second function key 140. A center portion 150 of the template presents an up arrow corresponding to the scroll direction of the up key 142, and a down arrow corresponding to the scroll direction of the down key 144.

B. Home Page

In one possible embodiment, the insulin pump 100 is controlled by a menu-driven application program that is stored in the ROM 118 and executed by the processor 102. The application program also is parameter-driven in that the outcome or steps executed by the various application programs depend on the operating parameters set by the user. Examples of outcomes and steps that depend on the operating parameters include delivery rates, delivery schedules, delivery amounts, the generation and presentation of menus, and the like.

The application program presents a home page 152 in the display portion 134 of the screen 106. The home page 152 includes a first icon 154 that illustrates the amount of insulin remaining in the insulin cartridge. This first icon 154 has the shape of a syringe and a bar 156 arranged relative to the syringe shape to illustrate the amount of remaining insulin. The amount of remaining insulin also is quantified and listed below the first icon 154. A second icon 158 has the shape of a battery and has a bar 160 arranged relative to the battery-shape to illustrate the amount of remaining battery life. The percentage of remaining life on the battery is positioned below the second icon 158.

In one possible embodiment, the home page 152 presents the current status 162 of the insulin pump's 100 operation. In the example set forth in the illustration, the insulin pump 100 is delivering insulin at a rate of 1.15 units per hour according to a first basal schedule. The home page 152 also presents the name 166 of the active delivery program it is executing and personal information 168 as programmed by the user. In the illustrated example, the personal information it displays is a banner "Mary's Pump," which identifies the owner of the insulin pump 100. Other examples of information that might be included in the personal field includes medical information about the pump user similar to that information included on a medical alert bracelet such as allergies and the fact that the patient is diabetic, more detailed information about the patient including the patient's full name, telephone number, and address, detailed information about the user's caregiver such as the name and telephone number of the user's physician, and a warning that the pump 100 is an insulin pump and should not be removed from the user.

Furthermore, the pump 100 can be configured to present more than one home page. In this embodiment, the user scrolls through the home pages using the up and down keys 142 and 144. For example, other home pages might include the date, time, and amount of the last bolus delivered by the insulin pump; contact information about the patient's caregiver; medical information about the patient such as a list of the user's allergies, a warning that the user is a diabetic, and a warning that the pump is an insulin pump and should not be removed.

The pump 100 displays an icon 170 in the home page 152 to identify the displayed page as the home page. Additionally, the icon 170 can include a page number to indicate which home page is currently being displayed. One possible shape for the home page icon is an icon having the shape of a house.

C. Suspending Delivery

Figure 3:
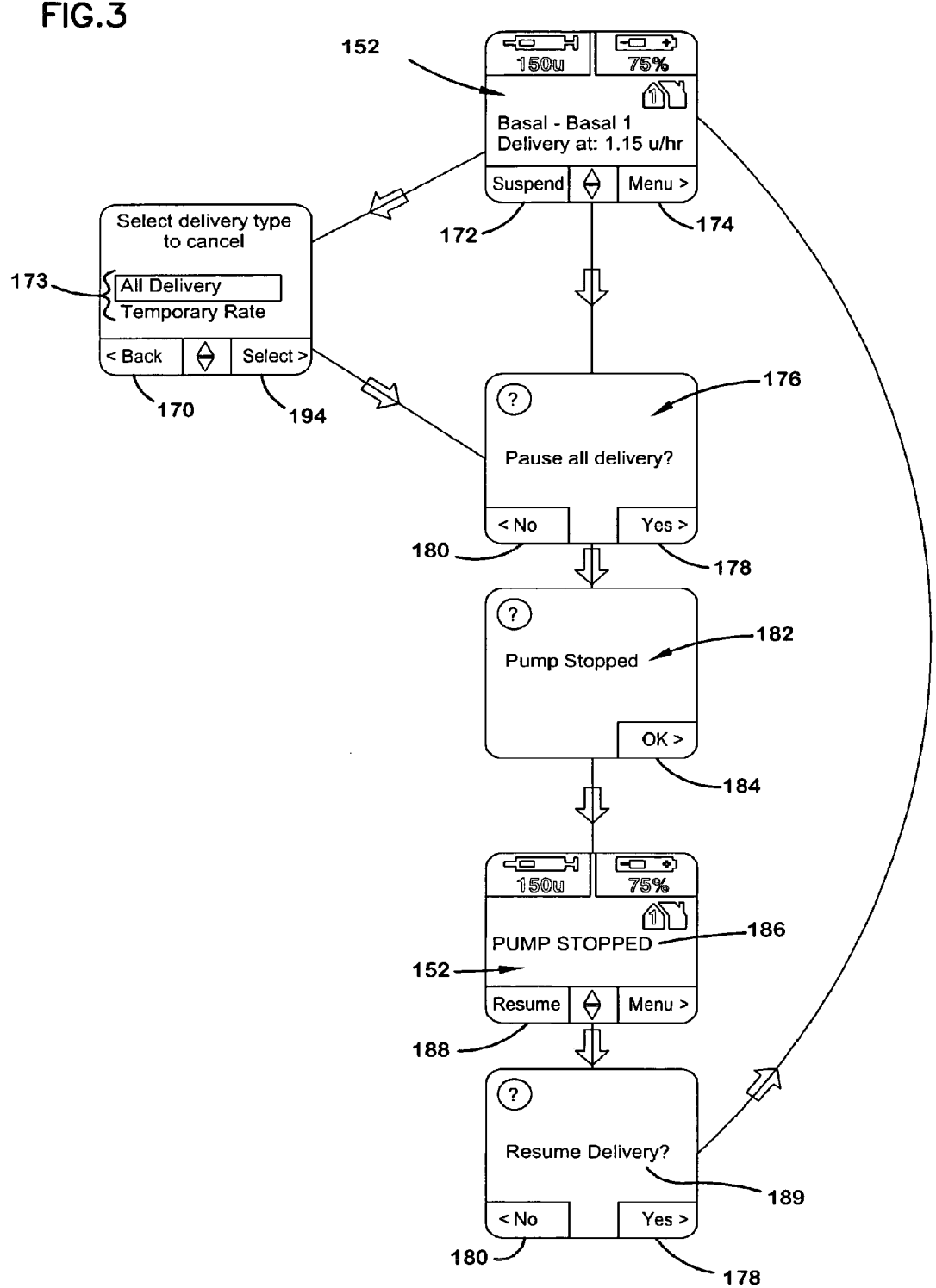
FIG. 3 illustrates a suspend operation executed by the pump shown in FIGS. 1 and 2.

Referring to FIG. 3, when the pump 100 is displaying the home page it assigns a suspend function 172 to the first function key 138 and a menu function 174 to the second function key 140. Accordingly, pressing the first function key 138 initiates a suspend pumping operation. If the pump 100 has an active delivery program in addition to the standard basal delivery program, the pump 100 displays a list of options that prompts 173 the user to select whether to suspend all active delivery programs or just one of the active delivery programs other than the standard delivery program. In one embodiment of the pump 100, there are three possible ways to deliver additional amounts of insulin over an extended period—an extended bolus, a combination bolus, and a temporary rate, all of which are described in more detail herein.

In the example set forth in FIG. 3, the pump 100 has an active temporary rate delivery program so the pump 100 prompts the user to select whether to suspend all active delivery programs or just the temporary rate delivery program by scrolling to the desired delivery program to suspend. The user then activates a Select function 194, which is assigned to the second function key 140.

After the user activates the Select function 194, the insulin pump 100 prompts 176 the user to confirm suspension of the selected delivery, whether it is all delivery, the extended bolus, the combination bolus, or the temporary rate. The user can confirm the suspend operation by activating the yes function 178 by pressing the second function key 140 or cancel the suspend operation by activating the no function 180 by pressing the first function key 138. If there is no insulin being delivered in addition to the standard basal rate, the insulin pump will automatically skip from the home page 152 to the prompt 176 asking the user to confirm suspension of the delivery.

When the user activates the yes function 178, the pump 100 displays a warning 182 that the insulin pump 100 is stopping delivery. The user then activates an o.k. function 184 and the pump 100 stops delivery, returns to the home page 152 and displays a banner 186 stating the pump 100 is stopped. On the home page 152, the pump 100 assigns a Resume function 188 in place of the suspend function 172. In one possible alternative embodiment, the insulin pump 100 merely displays the warning that the pump 100 is stopping delivery for a predetermined period of time (e.g., 5 seconds) and then stops the pump 100 and returns to the home page 152.

To resume pumping, the user activates the Resume function. The insulin pump 100 then prompts 189 the user to either confirm or cancel the resume function by activating either a yes function 178 or a no function 180.

Alternatively, at the list that prompts 173 the user to select whether to suspend all active delivery programs or just one of the active delivery programs other than the standard delivery program, the user can return to the previous display (i.e., the home page 152) by activating a Back function 170, which is assigned to the first function key 138. Activating the Back function, whenever it is assigned to the first function key 138, always returns the pump 100 back to the previous display.

D. Main Menu and Time/Date

Figure 4:
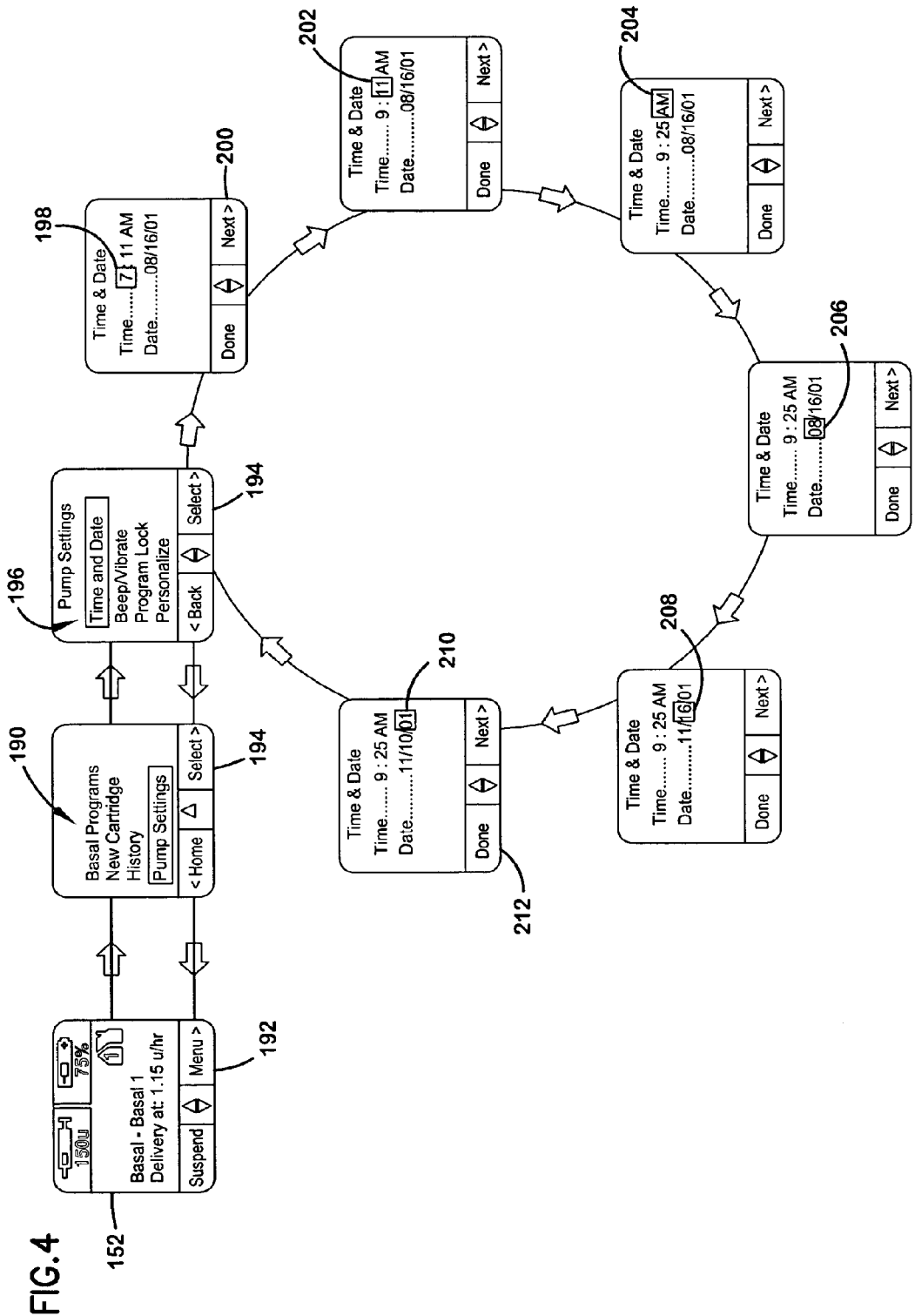
FIG. 4 illustrates setting time and date operating parameters in the pump shown in FIGS. 1 and 2.

Referring to FIG. 4, the user accesses a main menu 190 by activating a menu function 192 assigned to the second function key 140. The insulin pump 100 then displays the main menu 190, which includes a plurality of menu items that the user can select for setting operation parameters and performing various tasks as described herein. In one possible embodiment, the menu items in the main menu are Basal Programs, New Cartridge, History, and Pump Settings. In other possible embodiments, the main menu 190 can be customized to include other menu items such as Correction Bolus, Temporary Rate, Meal Bolus, and others. Furthermore, the user can customize at least some of the labels for various menu items in both the main menu 190 and submenus.

The New Cartridge menu item is selected to access the cartridge or syringe of insulin loaded in the pump 100. In one possible embodiment, selecting the New Cartridge menu item automatically sequences the user through the steps of loading the new cartridge, priming the tubing for the infusion set, priming the cannula, and setting the display site reminder, if the display site reminder is enabled. The display site reminder is discussed below in more detail. In yet another embodiment the user must affirmatively acknowledge each of these steps by pressing a predetermined key, either the first or second function keys 138 or 140 on the keypad 124, at the conclusion of each step, which causes the pump to index to the next step. After sequencing through each of these steps, the pump 100 prompts the user to enter an instruction whether to resume delivery of insulin.

Accessing the cartridge is discussed in more detail in U.S. patent application Ser. No. 10/086,646, now U.S. Pat. No. 7,033,338, entitled Cartridge and Pump With Axial Loading, the disclosure of which was incorporated by reference above.

The user selects the desired menu item by using the up and down keys 142 and 144 until the desired menu item is highlighted or otherwise marked. The user then activates the highlighted menu item by activating a select function 194 assigned to the second function key 140.

By selecting the Pump Settings menu item, the pump brings up a Pump Settings submenu 196 of several submenu items, including Time and Date, Beep/Vibrate, Program Lock, and Personalize. The Time and Date menu option is selected to set the time and date of the clock. This time and date is set in real time. When the Time and Date menu option is selected, the screen displays the time and date, and focus is placed on the hour field 198. The user scrolls through values for the hour until the desired value is set. The user then activates a next function 200 assigned to the second function key 140 to index through the remaining fields for the time and date (e.g., the minute field 202, the am/pm field 204, the month field 206, the day field 208, and the year field 210) and set the desired values for each of these fields. The user exits the Time and Date function at any time by activating the Done function 212 assigned to the first function key 138. Activating the Done function 212 saves the current time and date settings and returns the pump to the Pump Settings submenu 196.

E. Beep/Vibrate

Figure 5:
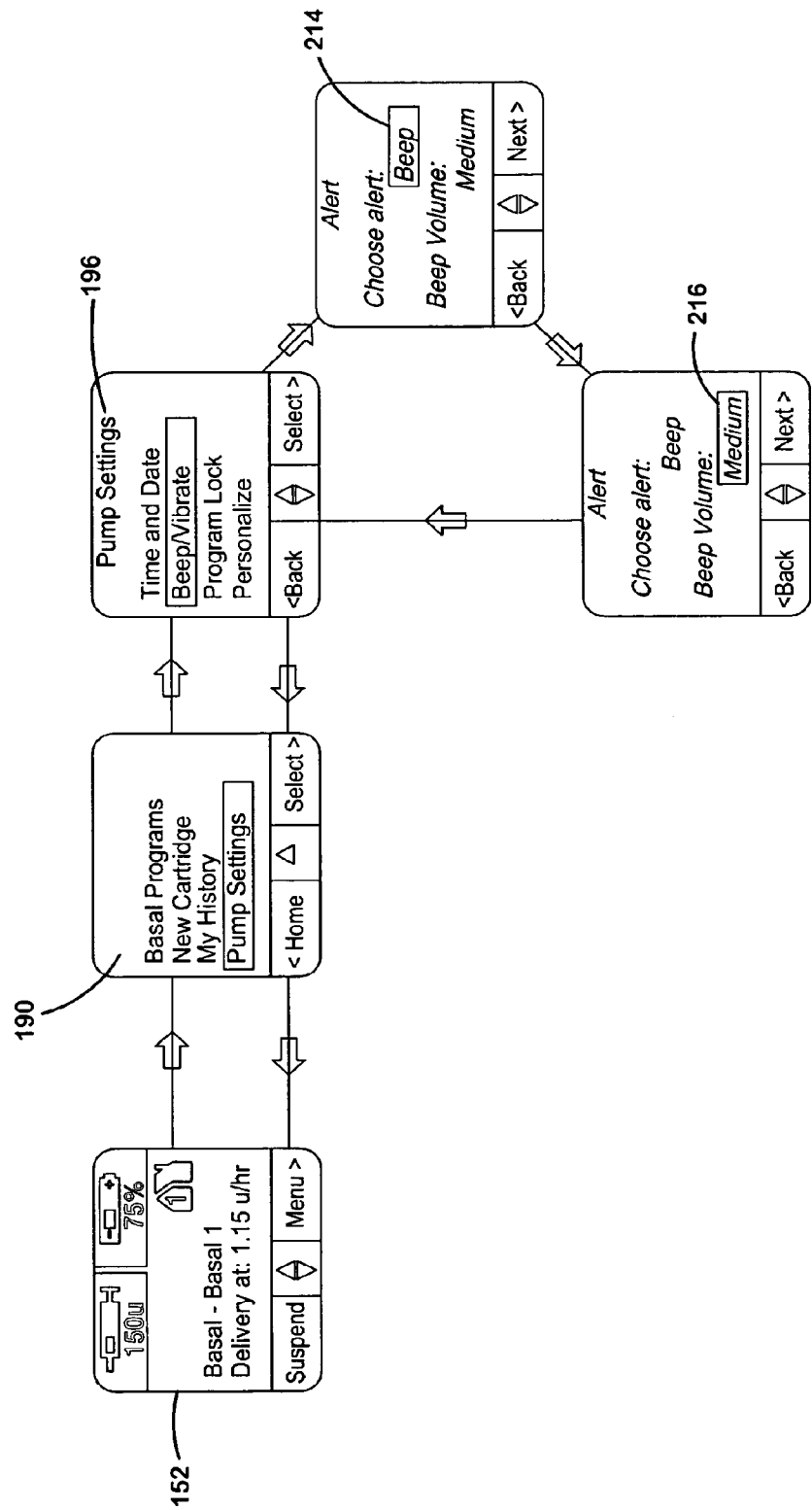
FIG. 5 illustrates setting alert styles in the pump shown in FIGS. 1 and 2.

Referring to FIG. 5, to configure an alarm function to generate either an audible or vibratory signal, the user selects the Beep/Vibrate menu option within the Pump Settings submenu 196. The pump 100 then indexes to the next user interface and places focus on a choose-alert field 214. The user scrolls to the desired beep setting or vibrate setting and selects that setting by activating the Next function 200 to select the desired setting. If the Beep setting is selected, focus changes to a beep-volume field 216 and the user scrolls to and selects the desired volume level. In one possible embodiment, the volume levels from which the user can select are low, medium, and high. Other embodiments use a numbered volume scale, labels such as indoor and outdoor, and the like. Upon selecting the desired volume level, the alert and volume settings are saved and the Pump Setting submenu 196 is displayed on the screen 106. If the user selects vibrate in the choose-alert field 214, the pump 100 will return directly to the Pump Setting submenu 196.

F. Lock

Figure 6:
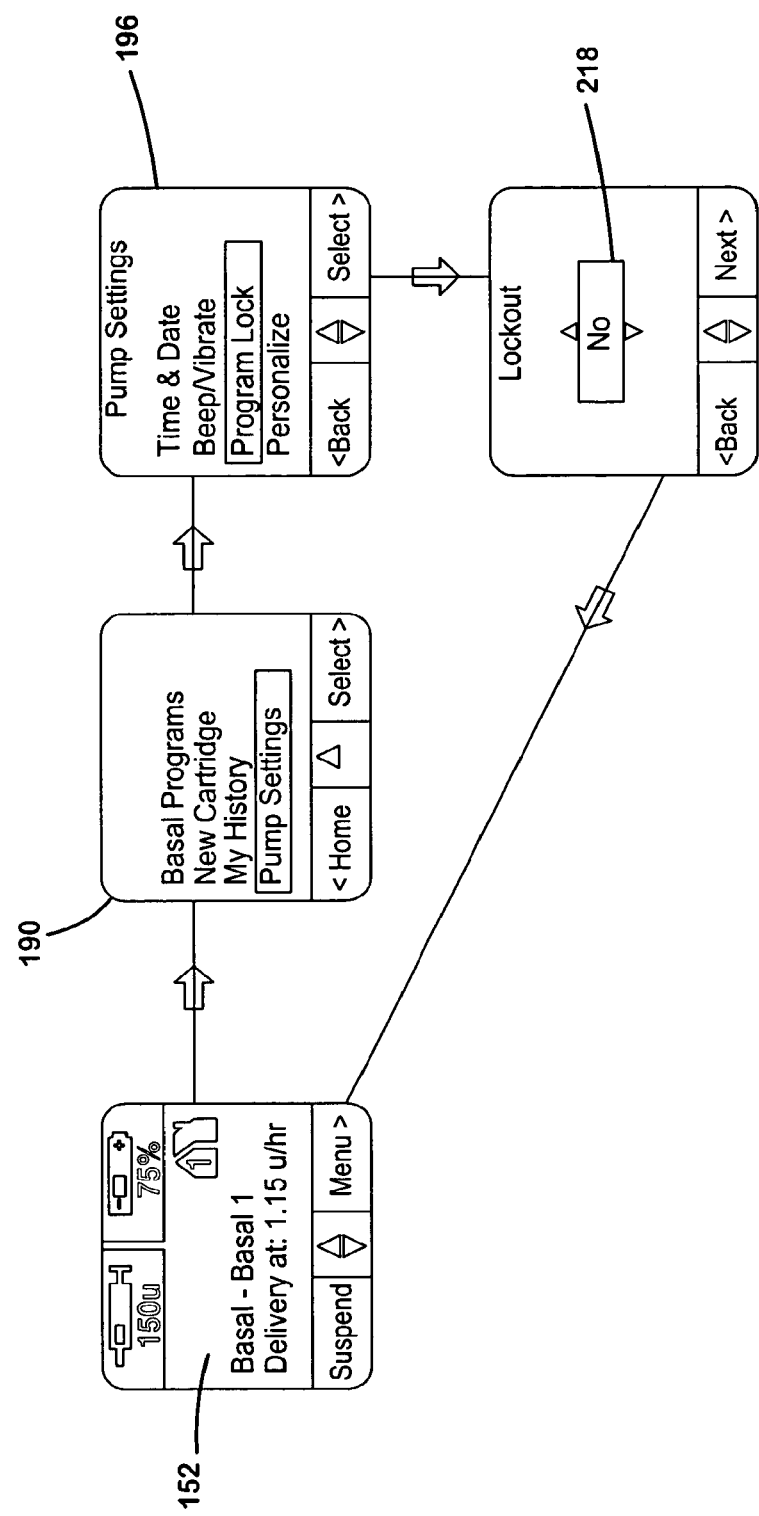
FIGS. 6 and 7 illustrate lock and unlock operations executed by the pump shown in FIGS. 1 and 2.

Referring to FIG. 6, to lock out the pump 100 and prevent anyone from entering the main menu 190, the user selects the Program Lock menu item in the Pump Settings submenu 196. Focus then indexes to a lockout user interface having a lockout field 218, which is placed in focus. The user scrolls and selects to the desired yes or no value. If the user selects no, the pump 100 continues operating and the pump 100 is not locked out. If the user selects yes, the pump 100 is locked and must be unlocked to access the main 190 menu from the home page 152. In one possible embodiment, if there are multiple home pages, the user can still scroll through all of the home pages without unlocking the main menu 190. In another possible embodiment, the user can still troubleshoot alarms without unlocking the pump 100.

Figure 7:
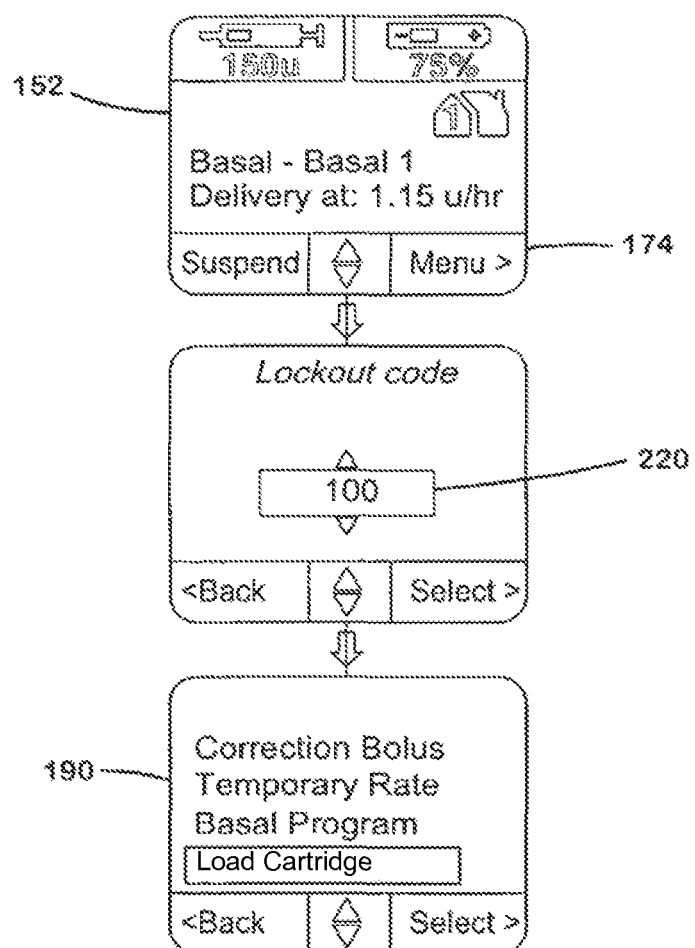

Referring to FIG. 7, to unlock the pump 100 the user activates the menu function 174 and the pump 100 indexes to a user interface having a lockout-code field 220, which is placed in focus. The user scrolls to and selects the lockout code. In one possible embodiment, the lockout code is a number and the user enters the lockout code by scrolling through possible codes. Upon selecting the proper lock-out code, the main menu 190 is unlocked and the main menu is displayed.

In alternative embodiments, there are separate fields for each digit in the lockout code. In this embodiment, the user indexes through the digits using the Next function 200 until the last digit is set at which time the pump 100 either unlocks the main menu or admonishes the user that the wrong code was entered.

Yet another embodiment of the pump 100 has lock levels in which the different codes can be entered into the pump 100, each code permitting access to a different set of commands and functions. Lock levels are described in more detail in commonly assigned U.S. Pat. No. 5,935,099, which is entitled DRUG PUMP SYSTEMS AND METHODS and issued on Aug. 10, 1999, the complete disclosure of which is hereby incorporated by reference.

G. Customizing Time and Date Formats

Figure 8:
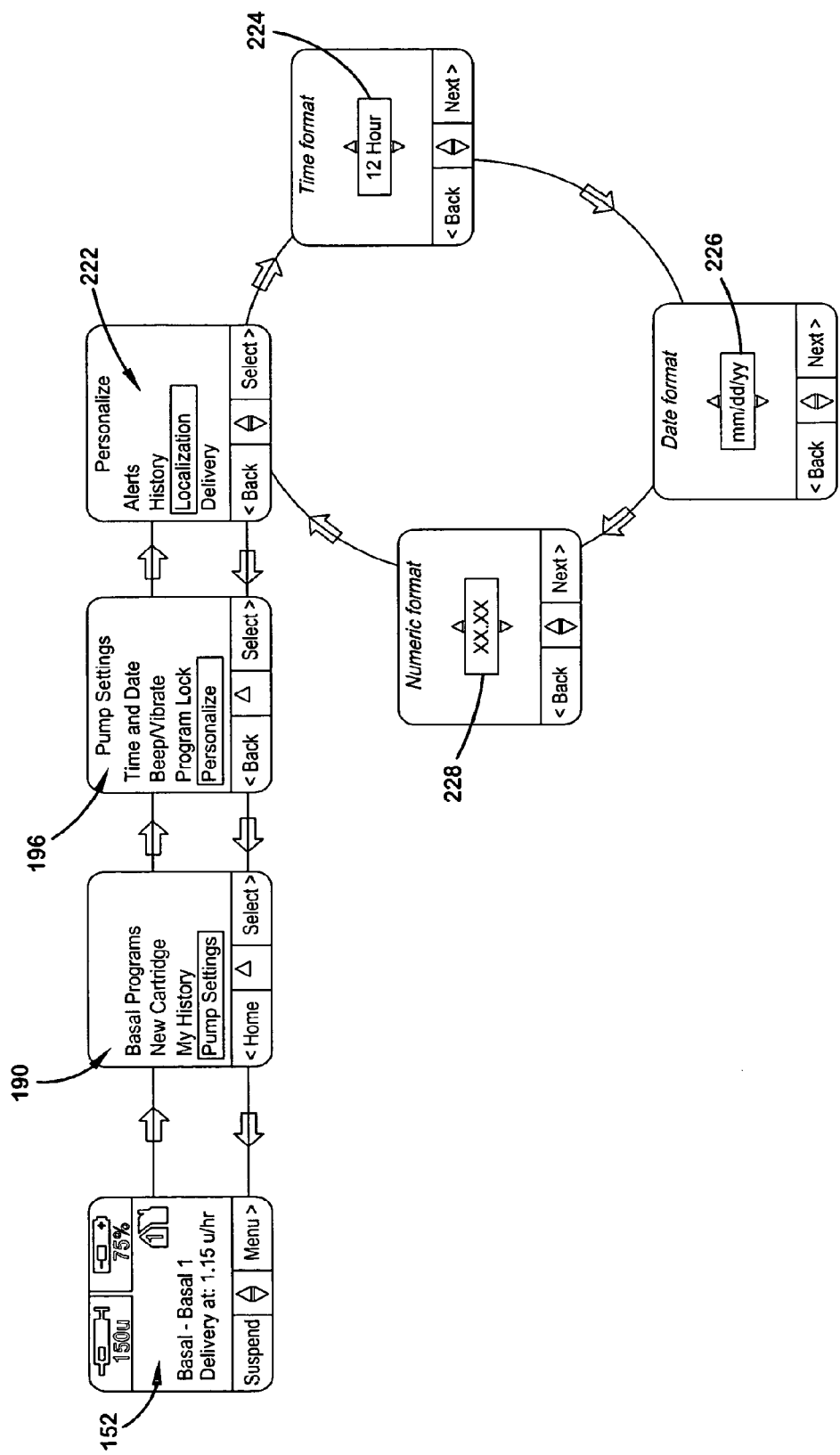
FIG. 8 illustrates setting time and date formats in the pump shown in FIGS. 1 and 2.

Referring to FIG. 8, to customize the time and date formats, the user selects a Personalize menu item in the Pump Settings submenu 196. The pump 100 then indexes to a Personalize submenu 222 in which the user selects a Localization menu item. The pump then indexes to a time-format field 224, which is placed in focus. The user scrolls to and selects the desired time format (e.g., 12-hour or 24-hour). The pump 100 then indexes focus to a date-format field 226. The user scrolls to and selects the desired date format (e.g., mm/dd/yy or dd/mm/yy). The pump 100 then indexes focus to a numeric-format field 228. The user scrolls to and selects the desired numeric format (e.g., xx.xx or xx,xx). The pump 100 then returns to the Personalize submenu 222. In an alternative embodiment, the user can also set a flag that causes the pump to automatically change time at the beginning and end of daylight savings time.

H. Customizing and Setting Alerts and Reminders

Figure 9:
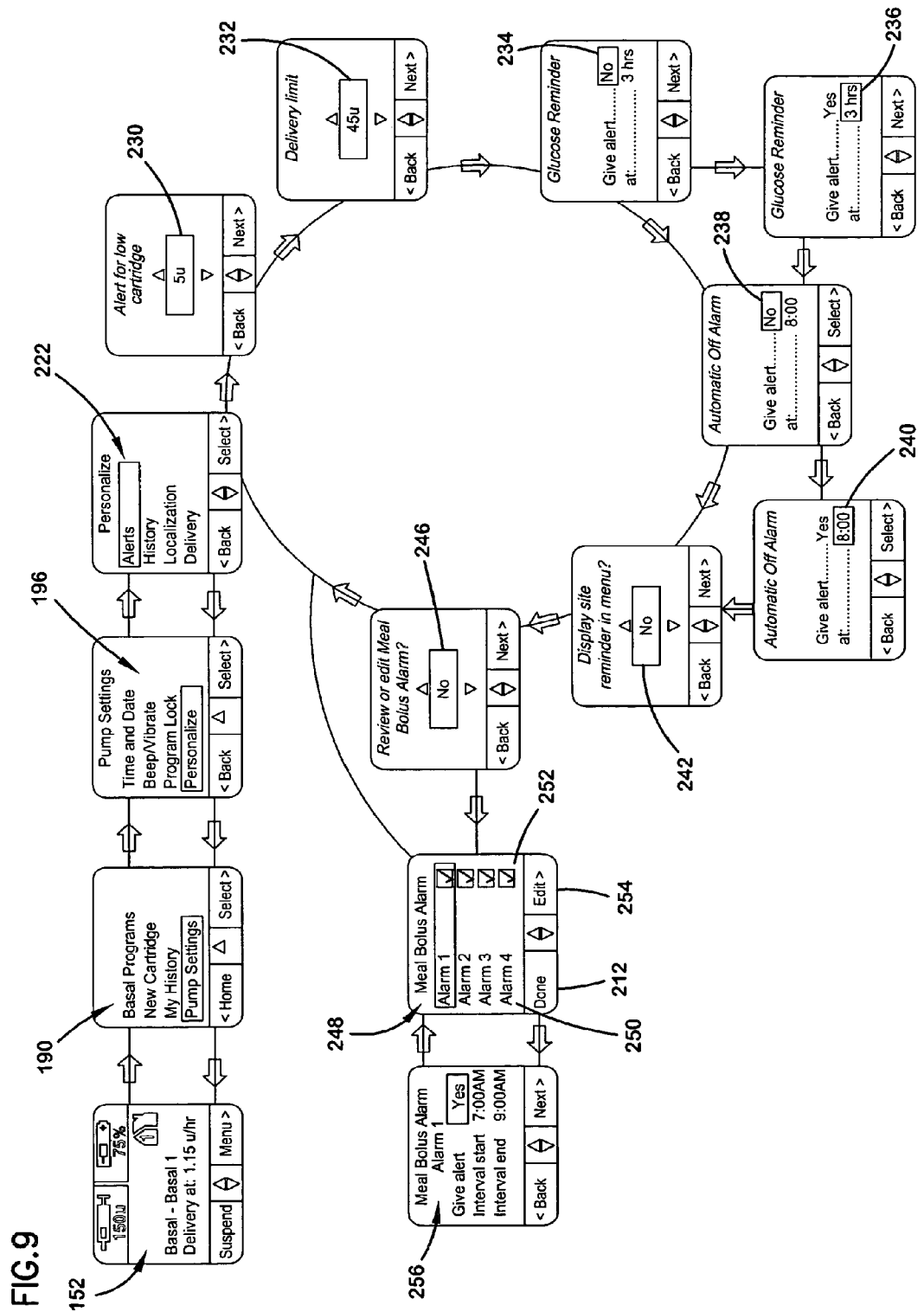
FIG. 9 illustrates setting alerts and reminders in the pump shown in FIGS. 1 and 2.

Referring to FIG. 9, to customize and set various alerts and reminders the user selects the Alerts item from the Personalize submenu 222. When the user selects the Alert menu item, the pump 100 indexes to a low-cartridge-alert field 230, which is placed into focus. The user scrolls to and selects the desired volume (i.e., remaining volume within the cartridge) at which the pump 100 will generate a low cartridge alert. In one possible embodiment, the user can select whether to set the threshold for the low volume alert in the range from 5 units to 50 units. Upon selecting the desired volume, focus indexes to a delivery-limit field 232. The user scrolls to and selects the desired delivery limit at which an alarm is generated when there is an attempt to deliver more insulin than is allowed in a one-hour period of time. In one possible embodiment, the user can select whether to set the threshold for the delivery limit alarm in the range from 2 units to 100 units.

The insulin pump 100 then indexes focus to a glucose-reminder field 234, which is an alert that reminds the pump user to check their blood glucose level, based on a triggering event such as when the user last loaded a new insulin cartridge into the pump 100 or administered a meal bolus. The user scrolls to the desired yes and no values or settings. The yes value enables the glucose reminder and the no value disables the glucose reminder.

The pump 100 then indexes focus to a duration field 236 in which the user sets the duration between the triggering event and when the glucose reminder signals an alert. The user scrolls to and selects the desired duration. In one possible embodiment, the user scrolls through values in the range from 1 hour to 5 hours in a predetermined increment, such as 15 minute, half hours, or one hour increments. The pump 100 then indexes focus to an automatic-off field 238. If the user selects no in the glucose-reminder field 234, the pump 100 will skip over the duration field 236 and index focus directly to the automatic-off field 238.

In this embodiment occurrence of the triggering event will begin a timer running, which will time out and generate an alarm when the duration lapses. When the alert is signaled, the pump displays a message reminding the user to check their blood glucose levels. The user activates a predetermined key, either the first or second function key 138 or 140 on the keypad 124, to clear the alert and the message.

Within the automatic-off field 238, the user sets an automatic-off alarm that is generated when no keys or buttons on the insulin pump or a remote control unit associated with the pump 100 are pressed within a predetermined period of time. The pump 100 also suspends delivery when the automatic off alarm is generated and generates an alarm display. In one possible embodiment, when the automatic off alarm is generated, the user must acknowledge the alarm while the alarm display is presented and then must reinitialize the pump 100 to resume delivery. Another embodiment, the alarm display includes a message stating that the pump is an insulin pump.

When the automatic-off field 238 is in focus, the user scrolls to and selects the desired yes or no value. If the user selects the yes value, the pump 100 enables the automatic-off alarm, and the pump 100 indexes focus to a duration field 240 in which the user scrolls to the desired duration corresponding to the delay before the automatic-off alarm is sounded and delivery is suspended. After the delay is set, the pump 100 indexes focus to a display-site-reminder field 242. If the user selects the no value in the automatic-off field 238, the pump 100 disables the automatic-off alarm, and indexes focus to the display-site-reminder field 242 and skips the duration field 240.

The display-site reminder is an alert that reminds the user to change their infusion set and access site (i.e., where on their body the insulin is injected). Within the display-site-reminder field 242, the user scrolls to and selects the desired yes and no values. If the user selects the yes function the pump 100 enables the display-site reminder, and if the user selects the no value, the user will disable the display-site reminder. In one possible embodiment, the display-site reminder will generate an alarm at a predetermined interval after the last time that the user changed their infusion set and access site. Upon selecting the yes or no value, focus indexes to a review/edit-meal-bolus-alarm field 246.

If the user enables the display site reminder, the pump 100 prompts the user to enter the interval (i.e., the number of days) after which to generate a reminder or alarm and the time of day at which to generate the reminder. For example, setting an interval of 2 days and a time of 4:00 pm, would cause the pump 100 to generate a display-site reminder at 4:00 pm on the second day after the interval starts to run. When the pump 100 generates the display-site reminder to change the user's infusion set and access site, it generates an audio and/or vibratory alarm and displays a banner or other visual reminder that the user acknowledges by pressing a designated function key 138 or 140 on the key pad 124. The pump 100 includes a display-site reminder menu item that the user selects to reset the display site reminder and to adjust the interval and time of day if so desired. The user would access this menu item and reset the display-site reminder when changing his or her infusion set and access site.

In one possible embodiment, the pump automatically takes the user through the process of setting the interval and time of day for the display site reminder when going through the sequence of loading the new cartridge or syringe into the pump 100 and priming the infusion set.

A meal bolus alarm is an alarm that reminds the user to deliver a meal bolus during a predetermined time interval. For example, if the user eats breakfast every day between 7:00 am and 8:00 am every day, the user may set a missed-meal-bolus alarm for an interval between 6:15 am and 8 am. In this example, an alarm sounds if a meal bolus is not delivered within this interval. In one possible embodiment, the user can set up to four separate missed-meal-bolus alarms.

Within the review/edit-meal-bolus-alarm field 246, the user scrolls to and selects the desired yes or no value. If the user selects the no value, the pump 100 returns to the Personalize submenu 222. If the user selects the yes value, the pump 100 presents a user interface 248 entitled "Meal Bolus Alarm," which lists the names 250 of the available alarms (Alarms 1-4 in the illustrated embodiment) and a check box 252 next to the name of each alarm. If a missed-meal-bolus alarm is enabled, the check box 252 is set. If a missed-meal-bolus alarm is not enabled, the check box 252 is cleared.

To set an alarm, the user scrolls to the name 250 of the desired alarm and activates an edit function 254, which is assigned to the second function key 140. The pump 100 then displays a user interface 256 entitled "Meal Bolus Alarm: Alarm X", where X identifies the alarm to which the screen relates. In the illustrated embodiment, the display 256 relates to Alarm 1. There is one Meal Bolus Alarm: Alarm X display 256 associated with each of the alarms 250. Within the Meal Bolus Alarm: Alarm X display 256, there are three fields, a give-alert field 258, an interval-start field 260, and an interval-end field 262.

The give-alert field 258 is the first field placed in focus. The user scrolls to and selects the desired yes or no value. The yes value enables the meal bolus alarm, and the no value disables the meal bolus alarm. If the user selects the no value, the pump 100 returns to the "Meal Bolus Alarm" user interface 248. If the user selects the yes value, the pump indexes focus to the interval-start field 260. The user then scrolls to and selects the desired start time for the interval. The pump 100 then indexes focus to the interval-end field 262. The user scrolls to and selects the desired end time for the interval. In one possible embodiment, the time values through which the use scrolls are set at 15 minute increments, although other embodiments will have other time increments.

The pump 100 then saves interval start and stop times for that meal bolus alarm and returns to the Meal Bolus Alarm display 248. The user can then select another meal bolus alarm to enable and set or to disable using the procedures discussed above. Alternatively, the user can activate the Done function 212 and the pump 100 will save the settings for all of the meal bolus alarms and return to the Personalize submenu 222.

I. Pump History

Figure 10:
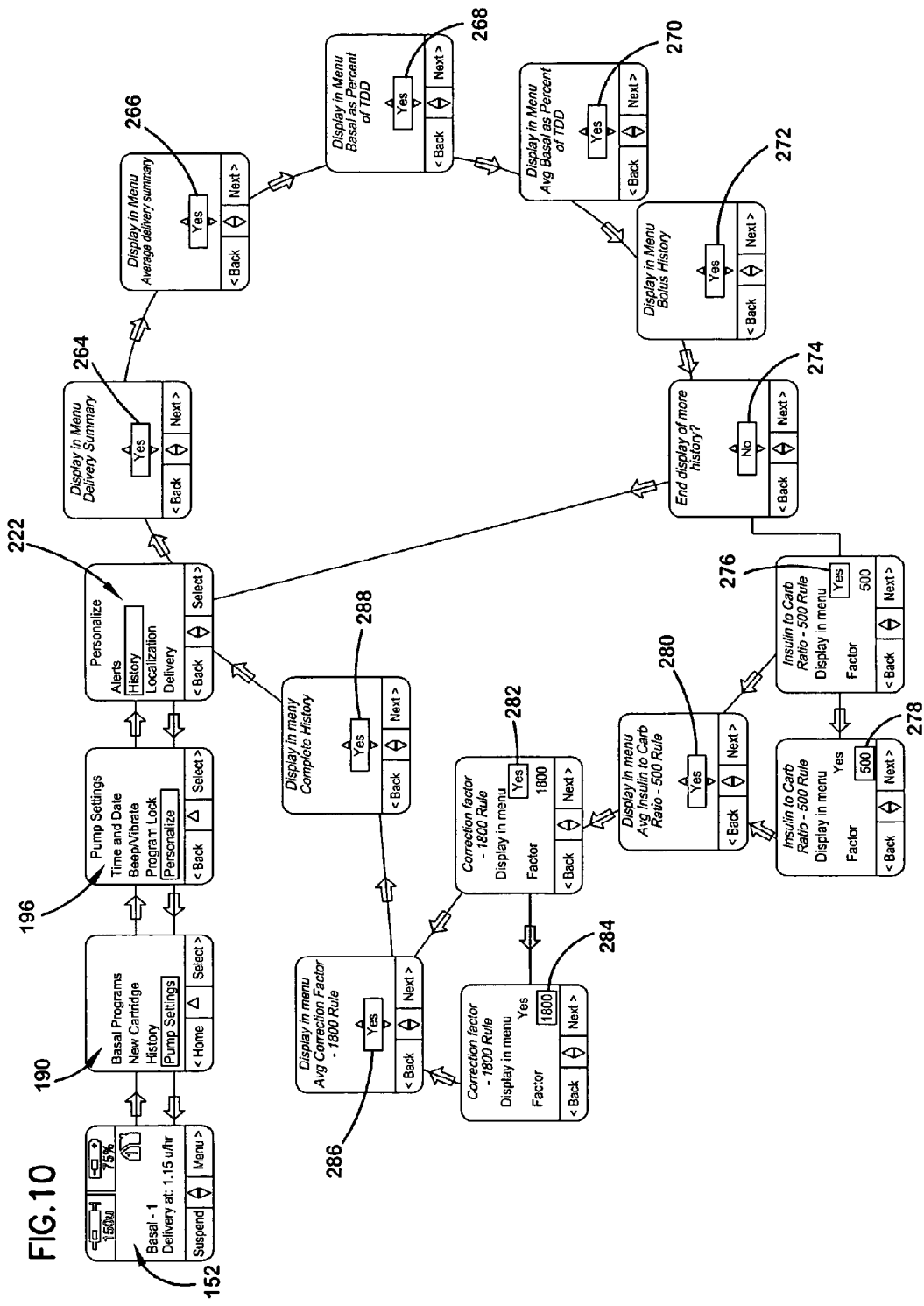
FIGS. 10 and 11 illustrate setting operational parameters related to the pump history for the pump shown in FIGS. 1 and 2.

Referring to FIG. 10, one possible embodiment of the insulin pump 100 tracks historical information related to the pump 100 such as delivery information and other events related to the pump 100. Historical information can be viewed on the screen 106 of the pump 100 or uploaded to a computer as discussed in more detail herein. The pump 100 can be customized to view historical delivery and event information in individual history screens or under the History item of the main menu 190. Additionally, the pump 100 can display delivery information either as individual events or as averages. These alternatives are only some of the possible embodiments.

The pump 100 can be programmed to track many different types of historical information, to present the historical information in many different ways, and to provide different ways to access historical information. In one possible embodiment, the historical information that the pump 100 tracks includes:

(1) The aggregate insulin delivered by the pump 100 as well as the amount of insulin broken down by insulin delivered as a meal bolus, insulin delivered to counteract estimated carbohydrates consumed by the user (if the carbohydrate estimator is used), delivered as a correction bolus, and delivered according to basal delivery protocols. In various embodiments, the pump 100 will record delivery according to basal delivery protocols as a total for all basal delivery protocols, or if the pump 100 is programmed with multiple delivery basal protocols, the delivered insulin can be broken down by each basal protocol used by the pump 100. In one possible embodiment, this data is stored as a daily total and an average daily total for a predetermined number of days. Additionally, in various embodiments, the average data can be recorded as actual average values or the average data can be calculated from the daily totals when requested for display or upon other requests.

(2) The amount of insulin delivered by the pump 100 according to a basal protocol as a percent of the total insulin delivered by the pump 100. In one possible embodiment, this data is stored as a daily percentage and an average daily percentage for a predetermined number of days. Additionally, in various embodiments, the average data can be recorded as actual average values or the average data can be calculated from the daily totals when requested for display or upon other requests.

(3) The date, time, and amount of each bolus delivered.

(4) The 500-Rule factor, which is used to estimate the grams of carbohydrates that are covered by each unit of insulin. To determine the grams of carbohydrates that are covered by each unit of insulin, the 500-Rule factor is divided by the total daily dose of insulin required to maintain the user blood sugar level in an acceptable range. The typical 500-Rule factor is 500, and hence the ratio is called the 500 Rule. However, the factor may vary for different types of insulin and from user to user and the value for the 500-Rule factor is calculated and stored. In one possible embodiment, the 500-Rule factor is stored as a daily value depending on the total delivery dose and an average value for a predetermined number of days. In an alternative embodiment, the 500-Rule factor is not stored but is calculated as the 500-Rule factor is required for a display, calculation, or other function.

(5) The 1800-Rule factor, which is used to estimate the number of units of insulin is required for each mg/dL (or mmol/L) drop in blood glucose. To determine the drop in blood glucose for each unit if insulin delivered to the user, the 1800-Rule factor is divided by the total daily dose of insulin required to maintain the user blood sugar level in an acceptable range. The typical 1800-Rule factor is 1800, and hence the ratio is called the 1800 Rule. However, the factor may vary for different types of insulin and from user to user and the value for the 1800-Rule factor is calculated and stored. In one possible embodiment, the 1800-Rule factor is stored as a daily value depending on the total delivery dose and an average value for a predetermined number of days. In an alternative embodiment, the 1800-Rule factor is not stored but is calculated as the 1800-Rule factor is required for a display, calculation, or other function.

(6) The complete history, which in one possible embodiment is the last 2000 events that are experienced by the pump, including all daily delivery totals, all alerts, all errors, all battery changes, all insulin cartridge changes, all changes to the pump program, and the like. Each record of an event includes the date and time that the event occurred. In other embodiments, a predetermined number of events other than 2000 are recorded. In yet another possible embodiment, the pump 100 records the events for a predetermined number of days rather than an absolute quantity, although there might be a limit to the total number of events that are recorded depending on available memory and other factors.

In one possible embodiment, as used herein total daily dose, also referred to as Total Daily Dose or TDD, refers to the total amount of insulin delivered during a single day excluding the amount of insulin delivered as a correction bolus. Other embodiments might includes the amount of insulin delivered as a correction bolus in the total daily dose of insulin.

To customize how the historical information is displayed on the pump 100, the user selects the History menu item from the Personalize submenu 222. The pump 100 indexes to a delivery-summary field 264, which is placed in focus. The user scrolls to and selects the desired yes or no value. The yes value enables the Delivery Summary menu item in the History submenu 290 (FIG. 11), and the no value disables the Delivery Summary menu item in the History submenu 290. Disabled menu items are not displayed as part of the menu. In one possible embodiment, the delivery summary displayed under this menu item includes the total daily dose of insulin delivered by the pump 100 as well as the amount of insulin broken down by insulin delivered as a meal bolus, insulin delivered to counteract estimated carbohydrates consumed by the user (if the carbohydrate estimator is used), delivered as a correction bolus, and delivered according to basal delivery protocols. In an alternative embodiment, the delivery summary includes the total or aggregate amount of insulin, including insulin delivered as a correction bolus.

Upon selecting the yes or no value in the delivery-summary field 264, focus indexes to an average-delivery-summary field 266, in which the user scrolls to and selects either a yes value or a no value. The yes value enables the Average Delivery Summary menu item in the History submenu 290, and the no value disables the Average Delivery Summary menu item in the History submenu 290. In one possible embodiment, the Average Delivery Summary displayed under this menu item includes the average daily total for a predetermined number of days for the aggregate insulin delivered by the pump as well as the amount of insulin broken down by insulin delivered as a meal bolus, insulin delivered to counteract estimated carbohydrates consumed by the user (if the carbohydrate estimator is used), delivered as a correction bolus, and delivered according to basal delivery protocols.

Upon selecting the yes or no value in the average-delivery-summary field 266, focus indexes to a basal-as-percent-of-TDD field 268. In one possible embodiment, basal as a percent of TDD is the amount of insulin delivered by the pump 100 according to a basal protocol as a daily percent of the total insulin delivered by the pump 100. The user selects whether to display the Basal as a Percent of TDD menu item in the History submenu 290 using a procedure similar to that described for the Delivery Summary. Under this menu item, the pump 100 lists the total daily amount of insulin delivered as a basal as a percent of the total daily dose of insulin delivered. In an alternative embodiment, the pump 100 lists the total daily amount of insulin delivered as a bolus as a percent of the total daily dose of insulin delivered. In various embodiments, the bolus as a percent can be listed as the meal bolus as a percent of the total daily dose of insulin delivered, correction bolus as a percent of the total daily dose of insulin delivered, or total bolus as a percent of the total daily dose of insulin delivered. The pump 100 then indexes focus to an average-basal-as-percent-of-TDD field 270. In one possible embodiment, average basal as a percent of total daily delivery (TDD) is the amount of insulin delivered by the pump 100 according to a basal protocol as an average daily percent over a predetermined number of days of the total insulin delivered by the pump 100. The user selects whether to display the Avg Basal as a Percent of TDD menu item in the History submenu 290 using a procedure similar to that described for the Delivery Summary. The pump 100 lists the average basal as a percent of the total daily delivery under this menu item.

The pump 100 then indexes focus to a bolus-history field 272. In one possible embodiment, the Bolus History is the date, time, and amount of each bolus delivered. The user selects whether to display a Bolus History menu item in the History submenu 290 using a procedure similar to that described for the Delivery Summary. The pump 100 lists the pump's 100 Bolus History under the Bolus History menu item.

The pump 100 then indexes focus to an edit-display-of-more-history field 274. The user scrolls to a yes value or a no value as desired and then activates the next function. If the user selects the no value, the pump returns to the Personalize submenu 222. If the user selects the yes value, the focus indexes to a carbohydrate-ratio field 276 in which the user scrolls to a yes value or a no value as desired and activates the Next function. Selecting the yes value causes the pump 100 to display a Calc 500 Rule menu item in the history submenu 290 and to display the calculated carbohydrate ratio. The pump indexes focus to a 500-rule-factor field 278 when the user selects yes in the 500-rule-factor field 276. The user then scrolls to the desired 500-Rule factor to use in various calculations and activates the Next function. In one possible embodiment, the potential factors are in the range from 400 to 600 in increments of 15. The pump 100 then indexes focus from the 500-rule-factor field to an average-carb-ratio field 280. Selecting the no value in the 500-Rule-factor field 276 disables display of the Calc 500 Rule menu item in the History submenu 290 and causes the pump 100 to index directly from the 500-rule-factor field 276 to the average-carb-ratio field 280.

Within the average-carb-ratio field 280, the user scrolls to and selects either a yes value or a no value. If the user selects the yes value, the pump 100 will enable an Avg Calc 500 Rule menu item in the History submenu 290. Under the Avg Calc 500 Rule menu item, the pump displays the average carbohydrate ratio for a predetermined number of days. In one possible embodiment, the pump 100 calculates the average carbohydrate ratio for a 7-day period. Upon selecting the yes or no value, the pump indexes focus to a correction-factor field 282.

In other embodiments, the pump calculates the average carbohydrate ratio for periods other than 7 days. For example, the range could be in the range from 2 to 90 days. In another possible embodiment, the pump 100 calculates the average carbohydrate ratio for however number of days it stores historical data. In yet another embodiment, the user can select a predetermined number of days over which to calculate and average the carbohydrate ratio.

If the user selects the yes value in the correction-factor field 282, the focus indexes to an 1800-rule-factor field 284. The user then scrolls to and selects the desired 1800-Rule factor to use in various calculations. In one possible embodiment, the potential 1800-Rule factors are in the range from 1500 to 2200 in increments of 100. The pump then indexes focus to an average-correction-factor field 286. Selecting the no value in the correction-factor field 282 disables display of the Calc 1800-Rule menu item in the History submenu 290 and causes the pump to index directly from the correction-factor field 282 to the average-correction-factor field 286.

Within the average-correction-factor field 286, the user scrolls to and selects a yes value or a no value. If the user selects the yes value, the pump 100 will enable the Avg. Calc 1800 Rule menu item in the History submenu 290. Under the Avg. Calc 1800 Rule menu item, the pump 100 displays the average correction factor for a predetermined number of days. In one possible embodiment, the pump 100 calculates the average correction factor for a 7-day period. Upon selecting the yes or no value, in the average-correction-factor field 286, the pump indexes focus to a complete-history field 288.

In other embodiments, the pump calculates the average correction factor for periods other than 7 days. For example, the range could be in the range from 2 to 90 days. In another possible embodiment, the pump 100 calculates the average correction factor for however number of days it stores historical data. In yet another embodiment, the user can select a predetermined number of days over which to calculate and average the correction factor.

Within the complete-history field 288, the user scrolls between either a yes value or a no value. The user selects yes to enable a Complete History menu item in the History submenu 290 and selects the no value to disable the Complete History menu item. Upon selecting either the yes or no value, the pump returns to the Personalize submenu. Under the Complete History menu item, the pump displays the complete body of historical information stored in RAM 116.

Figure 11:
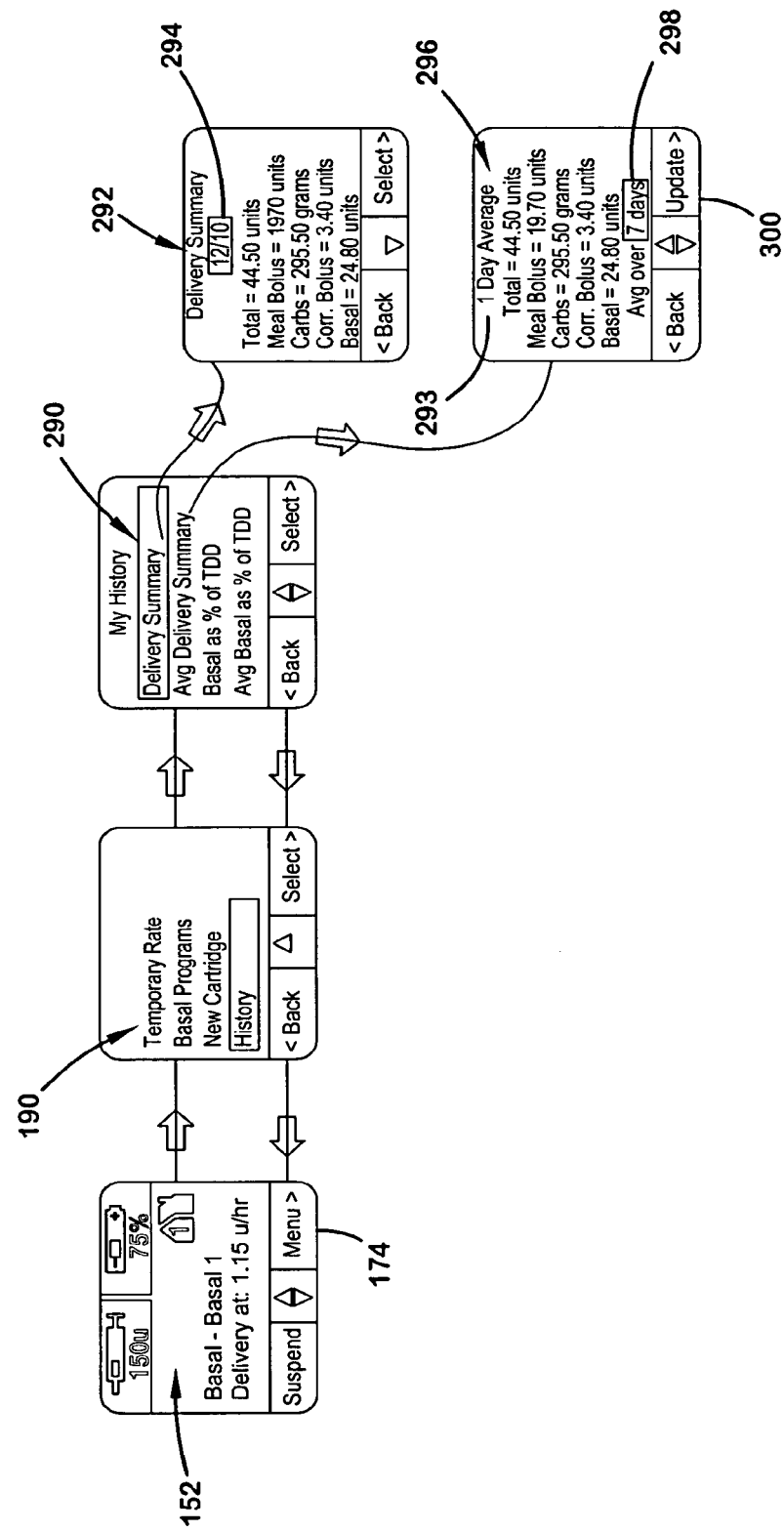

Referring now to FIG. 11, viewing historical information about the pump 100 is accomplished through the main menu 190. The user activates the Menu function 174 to access the main menu 190. Within the Main Menu 190, the user selects and activates the History menu item. The pump then indexes to the History submenu 290 that lists the historical information that is available to view on the pump 100. As described above, the historical information that is available, depending on the setting made within the History item of the Personalize submenu 222 as described above, are Delivery Summary, Avg Delivery Summary, Basal as a Percent of TDD, Avg Basal as a percent of TDD, Calc 500 Rule, Avg Calc 500 Rule, Calc 1800 Rule, and Avg Calc 1800 rule.

If the user selects Delivery Summary, the pump indexes to a Delivery Summary 292 that has a date field 294 in which the current date is listed and a Total field in which the total number of insulin units delivered is listed, a Meal Bolus field in which the number of insulin units delivered as a meal bolus is listed, a Carbs field in which the total number of carbohydrates that the user entered as an estimate of carbohydrate consumption is listed, Corr. Bolus field in which the total number of insulin units delivered as a correction bolus are listed, and a Basal field in which the total number of insulin units delivered according to the basal protocols employed by the pump are listed.

The user can scroll through dates in the date field 294 and see this historical information for dates other than the current date. In one possible embodiment, the user can scroll through the seven different dates, including the current date and the six previous dates. When the user scrolls to a different date, the pump automatically updates the historical delivery information relating to delivery that occurred on the date now listed in the date field. In an alternative embodiment, the user can scroll through the previous 90 days of data. In yet another possible embodiment, the user can scroll through however many days of data are stored on the pump 100.

If the user selects the Avg Delivery Summary menu item in the History submenu 290, the pump 100 indexes to a display 296 entitled "7 Day Average," 293 and displays the same fields (Total field, Meal Bolus field, Carbs field, Con. Bolus field, Basal field) as the Delivery Summary display 292. However, rather than daily totals, the fields present that average number of insulin units delivered over a predetermined number of days. Additionally, in place of the date field 294, the screen for the Avg Delivery Summary presents an avg-over field 298, which contains the number of days for which the historical data is being averaged. The user can change the number of days by scrolling up or down using the up or down keys, respectively. In one possible embodiment, the number of days that can be averaged are in the range from 2-30. In another possible embodiment, the number of days that can be averaged are in the range from 2-90 days. In yet another possible embodiment, the number of days that can be averaged are in the range from 2 days to however many days of historical data are stored on the pump 100. After scrolling to a new number of days to average, the user activates an Update Function 300 and the pump 100 recalculates the averages.

If the user changes the number of days over which the average data is calculated, the title "7 Day Average" 293 changes to "X Day Average," where X is the selected number of days over which the data is averaged.

If the use selects the Basal as % of TDD item menu from the History submenu 290, the pump 100 will display a "Basal as % of TDD" display (not shown) and present the percent of total insulin delivered by the pump according to the basal delivery protocols on any given day. The Basal as % of TDD display will present a date field in which the user can change the day for which the historical information is presented in a manner similar to the Delivery Summary display 292 as described above.

If the use selects the Avg Basal as % of TDD item menu from the History submenu 290, the pump 100 will display an "Avg Basal as % of TDD" display (not shown) and present the average percent of total insulin delivered by the pump 100 according to the basal delivery protocols for a predefined number of days. The Basal as % of TDD screen will display an avg-over field 298 in which the user can change the number of days for which the historical information averaged in a manner similar to the 7 Day Summary display 296 as described above.

If the user selects Calc 500 Rule, the pump will index to a "Carb Ratio—500 Rule" display and present a table of information. In each row of the table, the pump will list a date and the calculated carbohydrate ratio for that date. The carbohydrate ratio is calculated by dividing the 500-Rule factor by the total number of insulin units delivered for that day. In one possible embodiment, the pump 100 will calculate and list the carbohydrate ratio for 30 days and the user can scroll through those values using the up and down keys. However, other embodiments will calculate and list the carbohydrate ratio for any other number of days.

If the user selects Avg Calc 500 Rule, the pump 100 indexes to an "Avg Carb Ratio—500 Rule" display. The pump 100 calculates and presents the average carbohydrate ratio for a predetermined number of days. The "Avg Carb Ratio—500 Rule" display includes an avg-over field 298 in which the user can change the number of days for which the average carbohydrate ratio is averaged in a manner similar to the "Avg Delivery Summary" display as described above.

If the user selects Calc 1800 Rule, the pump 100 will index to a "Correction Factor—1800 Rule" display and present a table of information. In each row of the table, the pump 100 will list a date and the calculated correction factor for that date. The correction factor is calculated by dividing the 1800-Rule factor by the total daily dose of insulin required to maintain the user blood sugar level in an acceptable range. In one possible embodiment, the pump 100 will calculate and list the correction factor for 30 days and the user can scroll through those values using the up and down keys 142 and 144. However, other embodiments will calculate and list the correction factor for other numbers of days.

If the user selects Avg Calc 1800 Rule, the pump 100 indexes to an "Avg Correction Factor—1800 Rule" display. The pump 100 calculates and presents the average correction factor for a predetermined number of days. The Avg Correction Factor—1800 Rule screen includes an avg-over field 298 in which the user can change the number of days for which the average correction factor is averaged in a manner similar to the "Avg Delivery Summary" display as described above.

J. Basal Rates

Figure 12:
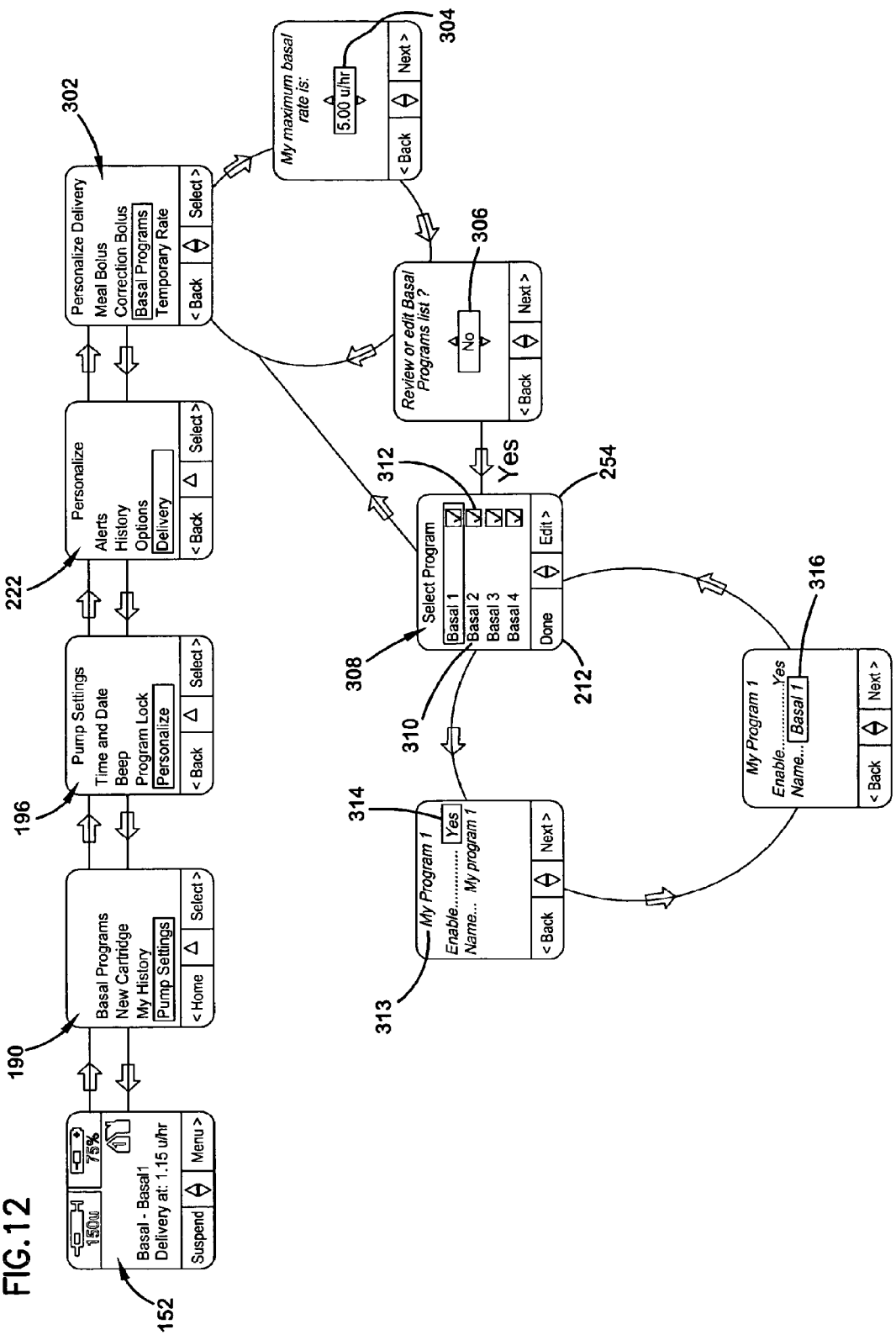
FIGS. 12-14 illustrate setting operational parameters for the basal rate delivery programs executed by the pump shown in FIGS. 1 and 2.

Referring to FIG. 12, the insulin pump 100 can deliver insulin either according to a basal rate or as a bolus. In one possible embodiment, the pump 100 can deliver insulin according to four different basal delivery programs. To customize the basal delivery programs, the user accesses the Personalize Delivery submenu 222.

Selecting the Delivery menu item in the Personalize submenu 222 causes the pump to index to a Personalize Delivery submenu 302 in which the user can select the type of bolus or basal delivery protocol to edit. Selecting the Basal Program menu item causes the pump 100 to index a maximum-basal-rate field 304, which is placed in focus. Within the maximum-basal-rate field 304, the user scrolls to and selects the desired maximum basal rate. In one possible embodiment, the maximum basal rate values are in the units of u/hr and the user can scroll through values in the range from 0.5 u/hr to 36 u/hr in increments of 0.5 u/hr. When the desired maximum basal rate is selected, focus indexes to a review/edit-basal-programs field 306 in which the user selects either a yes or a no value. If the user selects the no value, the insulin pump 100 returns to the Personalize Delivery submenu 302.

If the user selects the yes value, the pump 100 indexes to a display 308 entitled "Select Program" and lists the name 310 for each of the basal programs, Basal 1, Basal 2, Basal 3, and Basal 4. A check box 312 is also displayed next to each name 310 for the basal delivery programs. If a Basal program is enabled, the check box 312 next to its name is set. If a Basal program is not enabled, the check box 312 next to its name is cleared. The name 310 of each enabled basal-delivery program is displayed as a menu item in the Basal Programs submenu 318 (FIG. 13) and the user can selectively activate the enabled programs.

To enable or disable a basal program, the user scrolls to the desired basal program and activates the Edit function 254. The pump 100 indexes to a display 313 entitled "My Program X," where X is the number of the basal program being edited. In the illustrated example, the title of the display is My Program 1 because Basal program 1 is being edited. The display has two fields, an enable field 314 and a name field 316. Within the enable field 314, the user selects either a yes value or a no value. If the user selects the no value, the pump 100 disables the basal program associated with the screen 313 (Basal Program 1 in the illustrated example) and returns to the Select Program display 308. The check box 312 for the disabled program is cleared. In one possible embodiment, if the pump 100 is actually executing the basal program that the user attempts to disable, the pump 100 will not disable the program and will present an error message stating, "You may not disable the active program."

If the user selects the yes value in the enable field 314, the pump 100 indexes focus to the name field 316. Within the name field 316, the user can assign a custom name to the basal delivery program. In one possible embodiment, the user can scroll through names that are preloaded into the pump 100. Examples of names might include Weekday, Weekend, Sick Day, Travel, Monthly, and the generic name Basal X, where X is the number of the basal program being edited. When the user has scrolled to the desired name, the user activates the Next function and the pump 100 returns to the Select Program display 308. The check box 312 for the program that was just edited is set to indicate that the basal program is enabled. Additionally, the name selected in the name field 316 is displayed in the Select Program display 308 in place of the previously assigned name. The name selected in the name field 316 is also displayed as a menu item in the Basal Programs submenu 318.

The user repeats this procedure from the Select Program display 308 for each basal program 310 for which he or she desires to change the enabled state and/or name. When the user is done changing the enabled states and program names for the various basal programs 310, the user activates the Done function 212. The pump 100 then returns to the Personalize Delivery submenu 302. As described below, the names of the enabled basal delivery programs will then appear the Basal Programs submenu 318.

In an alternative embodiment, within the display entitled "My Program X," the user can access a spin box in which they scroll through a list of optional names and select a custom name for the enabled basal delivery programs. The selected name would then replace the generic name (e.g., Basal 1, Basal 2, Basal 3, and Basal 4 in the illustrated example) for the program associated with the display. Examples of optional names that might be loaded in the pump 100 include weekday, weekend, sick, and monthly (which is to designate a basal delivery program set for a woman's menstrual cycle).

Figure 13:
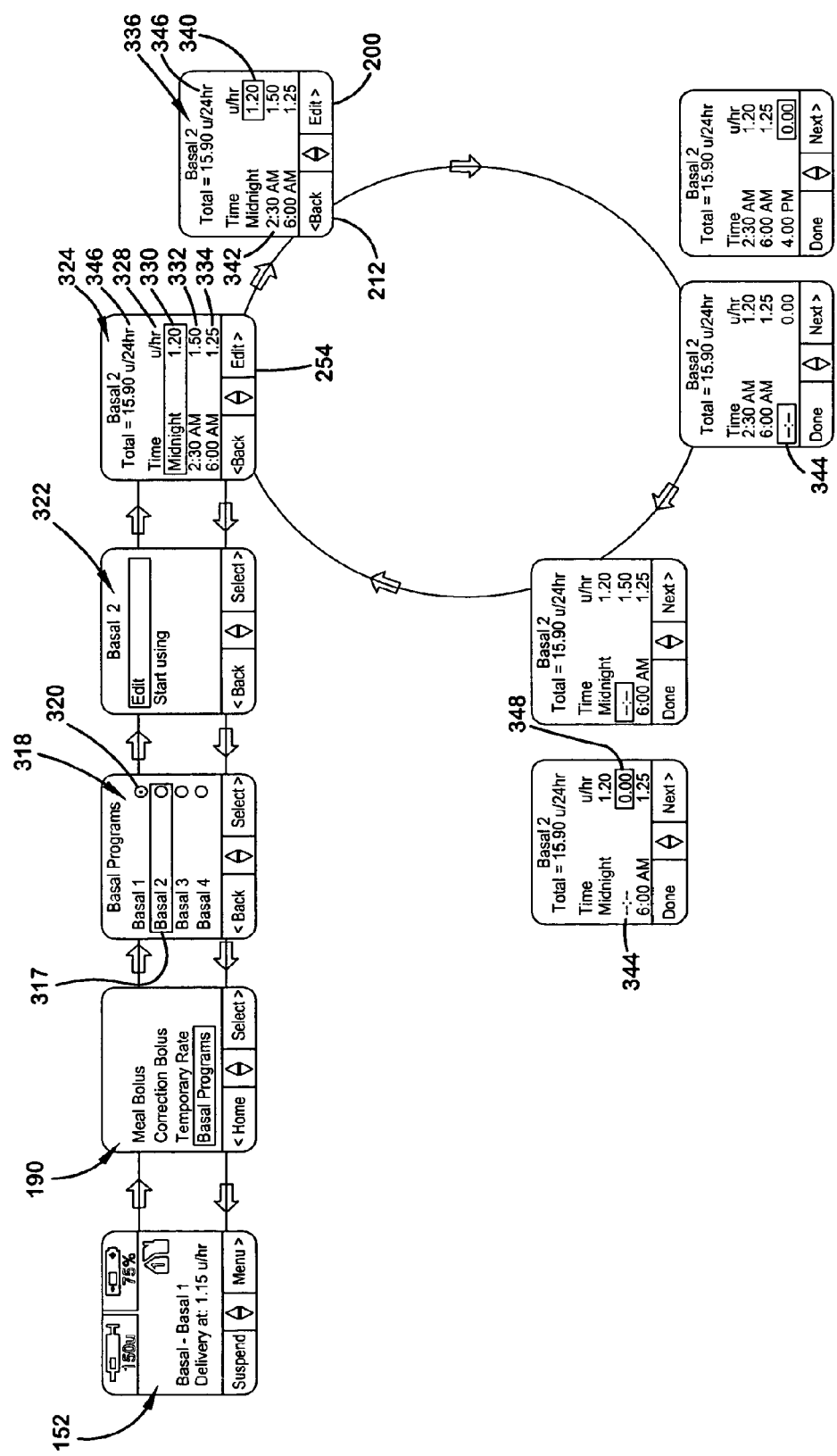

Referring now to FIG. 13, the user can edit the operating parameters for the delivery protocols assigned to each of the enabled basal programs. From the main menu, the user selects the Basal Programs menu item. The pump then indexes to a Basal Programs submenu 318 that lists those basal programs 317 that have been enabled as menu items. Each Basal Delivery program listed in the submenu 318 is identified by the name assigned to that particular program (e.g., Basal X, Weekend, Weekday, Sick Day, Travel, Monthly). In the illustrated example, all four basal programs are enabled and identified by the generic name Basal X. Additionally, there is button 320 next to each of the menu items (names for the enabled basal programs). The buttons 320 associated with the active basal program are set, and the buttons for the other basal delivery programs are cleared.

To edit a basal program, the user scrolls to and selects the desired basal program. The pump 100 indexes to a submenu 322 for which the title is the same name as the selected basal program. The menu has two menu items, an Edit menu item and a Start Using menu item. The user selects the edit menu item and the pump 100 indexes to a Summary user interface 324 that presents a table in which each row identifies a start time 326 and a scheduled delivery rate 328 for each time interval in the basal program. In the illustrated embodiment, there is a first time interval 330 having a start time and a delivery rate, a second time interval 332 having a start time and a delivery rate, and a third time interval having 334 a start time and a delivery rate. The start times are listed in a start-time field, and the delivery rates, are listed in a delivery-rate field.

To edit the start times and the delivery rates, the user activates the edit function 254 in the Summary user interface 324 and the pump 100 indexes to an Edit user interface 336 and assigns the Done function 212 to the first function key 138. Additionally, the pump 100 places focus on the delivery-rate field 340 for the first interval 330. The user scrolls to and selects the desired delivery rate. The user selects the desired delivery by scrolling to the desired value and activating the Next function 200. In one possible embodiment, the pump 100 scrolls through delivery rates in the range from 0 u/hr to 2 u/hr in increments of 0.05 units per hour. The delivery rate does not exceed the maximum delivery rate (FIG. 12, Item 304).

When the desired delivery rate is selected, the pump 100 indexes focus to the start-time field 342 for the second time interval 332. The user scrolls to and selects the desired start time. In one possible embodiment, the pump 100 scrolls through start times in increments of 30 minutes. In one possible embodiment, the start time cannot be earlier than or equal to the start time of the previous time interval and cannot be later than or equal to the start time of the next subsequent time interval. Other embodiments will implement different scrolling increments and limitations on the start time that can be selected. In another embodiment, if a selected start time is not in sequence, the pump 100 will automatically reposition the delivery intervals so they are in chronological order.

When the desired start time is selected, pump 100 then indexes focus to the delivery-rate field 340 for the second time interval 332, which the user sets using the procedures described above with respect to the first time interval 330. The user continues this procedure indexing through the start times for each of the time intervals and their associated delivery rates until the start time for each of the delivery intervals and their associated delivery rates are set. When the user is finished setting and/or editing the start times and delivery rates for the various intervals, he or she activates the Done function 212 and the pump 100 returns to the Summary Display 324.

In one possible embodiment, the first time interval 330 always starts at 12:00 midnight. In this embodiment, the last time interval will terminate at 12:00 midnight. If, within the Summary Display 324, the user highlights and selects the first time interval 330 for editing, the pump 100 indexes to the Edit display 336 and initially highlights the delivery rate 328 for the first time interval 330 rather than the start time 326. In another embodiment, however, the user can change the start time 320 for the first time interval 330. The last time interval would then extend until the start time for the first time interval 330. Additionally, within the Summary Display 324, the user can scroll to a delivery interval other than the first interval 330 and activate the Edit function 254. In this situation, the start-time field 342 for the selected interval is initially placed into focus rather than the delivery-rate field 340.

To add a time interval to the basal program, the user continues to index through all of the time intervals and associated fields until the pump generates a new delivery interval and displays the characters "--:--" 344 in the start-time field 342 of the new interval, which occurs after indexing through the delivery-rate field 340 for the last time interval. The user then scrolls through desired start times for the new time interval. After the desired start time is selected, the user activates the Next function 200 and the pump 100 indexes to the delivery-rate field 340 for the new time interval, which the user sets by scrolling through available delivery rate values. The user can then activate the Next function 200 to add yet another new time interval or can activate the Done function 212 to return to the Summary display 324. In one embodiment, the pump 100 can include up to 48 time segments, although other embodiment will include more or fewer time segments.

To delete a time interval from the basal program, the user places the start-time field 342 for the desired interval into focus and scrolls down until the time reads "--:--" 344. The user then activates the Next function 200 to index focus to the delivery-rate field 340. The user then scrolls the delivery rate down to 0.00348 and either activates the Next function 200 to index to another time interval for editing or activates the Done function 212 to return to the Summary display 324.

Additionally, both the Summary user interface 324 and the Edit user interface 336 include a total field 346 in which the total insulin scheduled to be delivered over a 24-hour period for that basal program is listed. The total insulin scheduled to be delivered is calculated by multiplying the delivery rate by the length of each time interval to calculate the total insulin to be delivered for each time interval by the basal program being edited. The total insulin to be delivered for each time interval is then summed to calculate the total insulin scheduled to be delivered over a 24-hour period.

Figure 14:
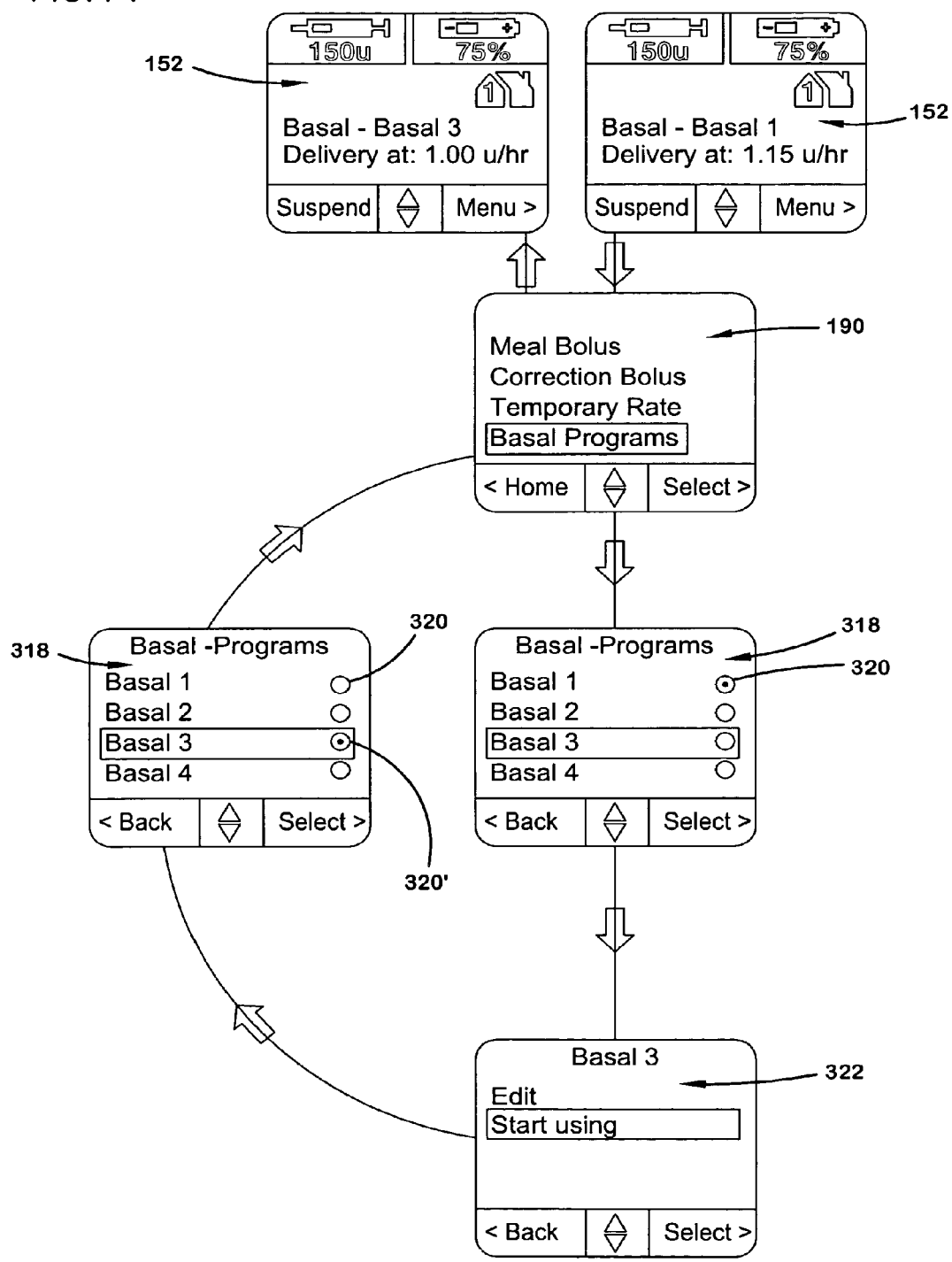

Referring to FIG. 14, to begin a basal program the user indexes to the Basal Programs submenu 318 and selects the name of the desired basal program. The pump indexes to the Basal X submenu 322 and selects the Start Using menu item. The pump returns to the Basal Programs submenu 318 and sets the button 320' for the newly activated basal program. The pump 100 also clears the button 320 for the previously active basal program.

K. Temporary Rate

Figure 15:
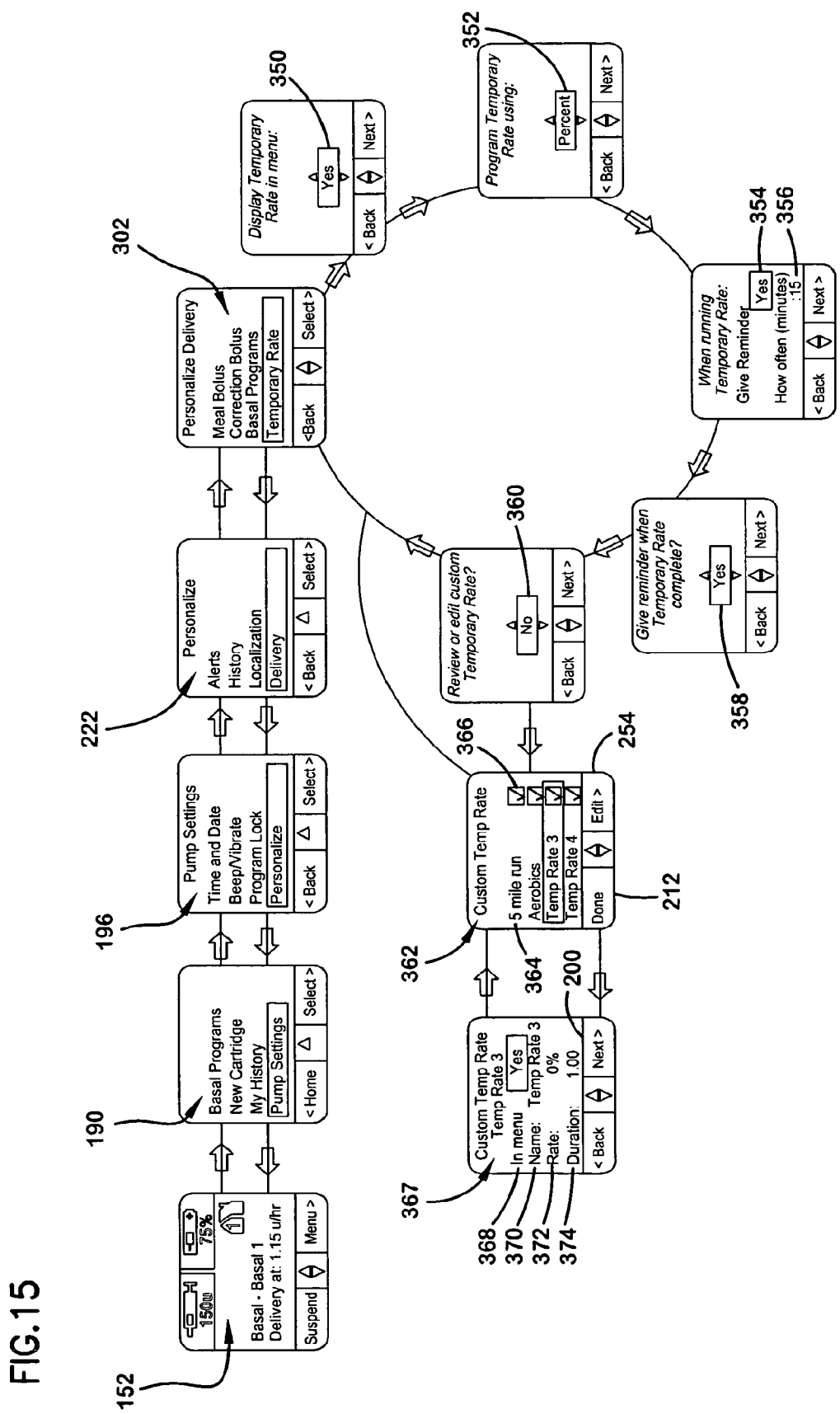
FIGS. 15-17 illustrate setting operational parameters for the temporary rate delivery programs executed by the pump shown in FIGS. 1 and 2.

A temporary rate allows the user to temporarily raise or lower the delivery rate being administered by the active bolus program. The user can personalize or customize the temporary rate programs and how they are present in the user interface. Referring to FIG. 15, to personalize the temporary rate programs, the user accesses the Personalize Delivery submenu 302.

Selecting the Delivery menu item in the Personalize submenu 222 causes the pump 100 to index to the Personalize Delivery submenu 302 and the user selects the Temporary Rate menu item. The pump 100 then displays a display-temporary-rate field 350, which is placed in focus. The user scrolls to and selects either a yes value or a no value. If the user selects the no value, the pump 100 returns to the Personalize Delivery submenu 302. If the user selects the yes value, the pump 100 indexes focus to program-temporary-rate-using field 352 in which the user scrolls between and selects either a Percent value and a Units/hr value. If the user selects the Percent value, the pump 100 sets the temporary rate delivery programs to increase and decrease the basal rate in terms of a percentage of the programmed basal rate and indexes focus to a give-reminder field. If the user selects the Units/hr value, the pump 100 sets the temporary rate delivery programs to increase and decrease the basal rate in terms of absolute units per hour and indexes focus to the give-reminder field.

When focus is on the give-reminder field 354, the user scrolls to and selects either a yes value or a no value. Selecting the yes value enables a temporary-rate reminder (either audible or vibratory) that is periodically generated while the pump 100 is delivering a temporary rate. Focus then indexes to an interval field 356 in which the user scrolls to and selects an interval that sets how frequently the pump 100 gives a reminder. In one possible embodiment, the user scrolls between 5 minutes and 1 hour in increments such as 5 minutes, 10 minutes, or 15 minutes. Upon selection of the interval, focus indexes to an end-temporary-rate-reminder field 358. Selecting the no value in the give-reminder field 358 disables the temporary-rate reminder and indexes focus directly from the give-reminder field 354 to the end-temporary-rate-reminder field 358.

Within the end-temporary-rate-reminder field 358, the user scrolls to and selects either a yes value or a no value. If the user selects the yes value, the pump 100 enables generation of the reminder upon completion of the temporary rate. The reminder is either an audible or vibratory reminder when delivery at the temporary rate is complete. In one possible embodiment, the reminder upon completion of the temporary rate is different than the reminder given to indicate that the temporary rate is still running. For example, an audible alarm might be longer, louder, or have a different sequence of beeps. Similarly, a vibratory alarm might be longer, stronger, or have a different sequence of vibrations. If the user selects the no value, the pump 100 disables the reminder.

The pump 100 next indexes focus to a review/edit-custom-temporary-rate field 360. The user scrolls to and selects either a yes value or a no value. If the user selects the no value, the pump returns to the Personalize Delivery submenu 302. If the user selects the yes value, the pump indexes to a display 362 entitled "Custom Temp Rate" and lists the name 364 of each customized temporary rate delivery program and displays a check box 366 next to each name 364. In one possible embodiment, there are four separate temporary rate programs. If a customized temporary rate program is enabled, the check box 366 for that delivery program is set. If a customized temporary rate program is disabled, the check box 366 for that temporary rate delivery program is cleared. When a customized temporary rate delivery program is enabled, it is displayed in the Temporary Basal Rates submenu 376 (FIG. 16) as described below and the user can then selectively execute the temporary rate delivery program through the Temporary Rates submenu 376. If the customized temporary rate delivery program is not enabled, it is not displayed in the Temporary Rates submenu 376 as described below and it cannot be executed.

To enable or disable a customized temporary rate program, the user scrolls to the name 364 of the desired program and activates the Edit function 254. The pump 100 indexes to a display 367 entitled "Custom Temp Rate: Temp Rate X," where X is the number of the customized temporary rate program being edited. In the illustrated example, the title of the screen is "Custom Temp Rate: Temp Rate 3" because temporary rate 3 is being edited. The screen has four fields, an in-menu field 368, a name field 370, a rate field 372, and a duration field 374.

The in-menu field 368 is initially placed in focus. Within this field, the user scrolls to and selects either a yes value and a no value. If the user activates the no value, the pump 100 disables the customized temporary rate program associated with the screen 367 (Temporary Rate Program 3 in the illustrated example) and returns to the Custom Temp Rate display 362. The check box 366 for the disabled temporary rate program is cleared. In one possible embodiment, if the pump 100 is actually executing the temporary rate program that the user attempts to disable, the pump 100 will not disable the program and will present an error message stating, "You may not disable the active temporary rate program."

If the user selects the yes value in the in-menu field 368, focus indexes to the name field 370. Within the name field 370, the user scrolls to and selects a name to assign the program. In one possible embodiment, the user can scroll through names such as Sick, Travel, Exercise, and the generic name Temp Rate X, where X is the number of the temporary rate program being edited. When the user has scrolled to the desired name, the user activates the Next function 200 and the pump 100 indexes to the rate field 372.

Within the rate field 372, the user scrolls to and selects a percentage to modify the basal rate. In one possible embodiment, the user can scroll through percentages in the range from 0% to 250%. When the desired percentage is selected, focus indexes to the duration field 374. Within the duration field 374, the user scrolls to and selects a duration for which they would like the temporary rate to be active once it begins.

In one possible embodiment, the user can scroll through rates in the range from 30 minutes to 72 hours. When the duration is selected, the pump 100 returns to the Custom Temp Rate display 362.

The user repeats this procedure from the Custom Temp Rate display 362 for each custom temporary rate program 364 for which they desire to edit the enabled state, name, rate, or duration. When the user is done editing custom temporary rate programs, he or she activates the Done function 212. The pump 100 then returns to the Personalize Delivery submenu 302. As described below, the names of the enabled custom temporary rate delivery programs will then appear in a submenu 376 entitled "Temporary Basal Rate".

Figure 16:
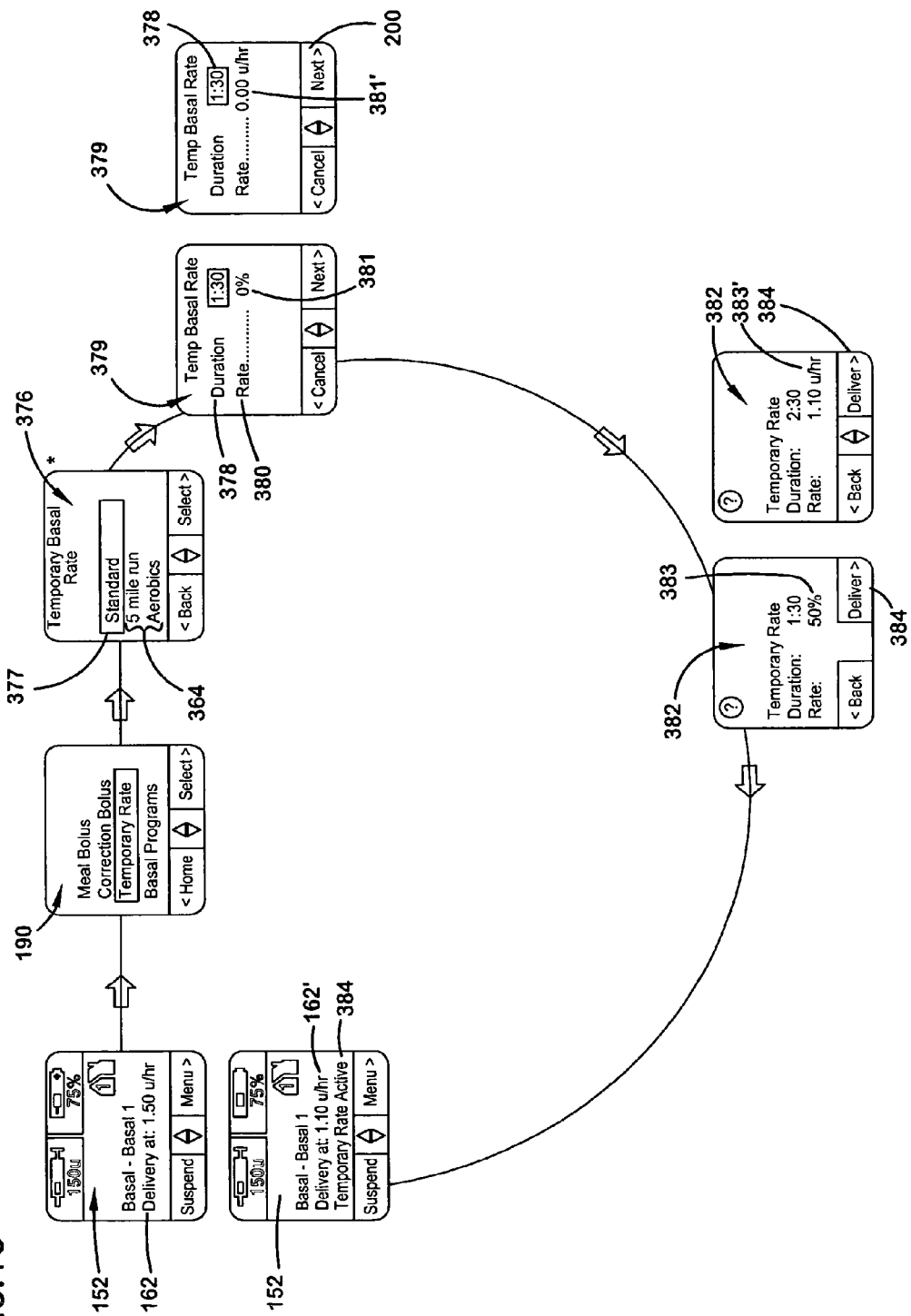

Referring to FIG. 16, a user activates a temporary rate by selecting the Temporary Rate menu item from the main menu 190. If the user has enabled any customized temporary rates as described above with reference to FIG. 15, the pump indexes to a Temporary Basal Rate submenu 376, which lists the standard temporary rate delivery program 377 and all of the custom temporary rate delivery programs 364 that are enabled. In the illustrated example, the two custom temporary rate delivery programs 364 are 5 mile run and aerobics. The user scrolls to and selects the desired delivery program.

When the user selects a temporary rate program for execution, the pump 100 indexes from the Temporary Basal Rate submenu 376 to an edit screen 379. In an alternative embodiment, if there are not any custom temporary rate programs 364 enabled (i.e., only the standard program 377 can be used), the pump 100 indexes directly from the main menu 190 to the edit screen 379 and skips the Temporary Basal Rate display 376.

The edit screen 379 has a duration field 378 that contains the duration for the temporary rate and a rate field 380 that contain data to set the temporary rate. If the temporary rate is one that was customized as described in conjunction with FIG. 15, the duration field 378 contains the duration as it was initially set in the "Custom Temp Rate: Temp Rate X" display 367. Similarly, the rate field 380 initially contains the rate data originally set in the "Custom Temp Rate: Temp Rate X" display 367. The user can then adjust these values by using the scroll keys to change the values and the Next function to index from the duration field 378 to the rate field 380. In one possible embodiment, for example, the duration can be set in the range from 0 minutes to 72 hours, and the rate can be set in the range from about 0% to about 400% if percent is the rate factor (or from a rate of 0 units per hour to the maximum basal rate if the units per hour is the rate factor).

If the user selects the Standard temporary basal rate program, the duration field 378 and rate field 380 are preprogrammed with a predetermined value that the user then adjusts to desired levels. If the temporary basal program is set to receive a percentage by which to adjust the basal rate, values in the rate field 380 are percentages 381. If the temporary basal program is set to receive a new basal rate, values in the rate field 380 are in units/hr 381'. In one possible embodiment, for example, the rate field 378 might be set at 100% (the current basal rate if units per hour is used) and the duration field 380 at 30 minutes. In another possible embodiment, the duration field 380 is preprogrammed at 0 minutes.

The user sets the duration, activates the Next function 200, sets the rate, activates the next function 200, and then the pump 100 indexes to a confirmation screen 382 that lists the set duration and rate (as a percentage 383 or in units/hr 383' depending on settings for the temporary rate program, for the temporary basal rate program. The user then activates a Deliver function 384 assigned to the second function key 140 and the pump 100 begins delivering insulin according to the operating parameters set in the temporary rate program. While the temporary rate is being delivered, the home page 152 will display the delivery rate 383' as modified 162' by the temporary rate and display a banner 384 stating that a temporary rate is active. In an alternative embodiment, if a custom temporary rate is active, the pump will display the name 364 assigned to the active custom temporary rate.

Figure 17:
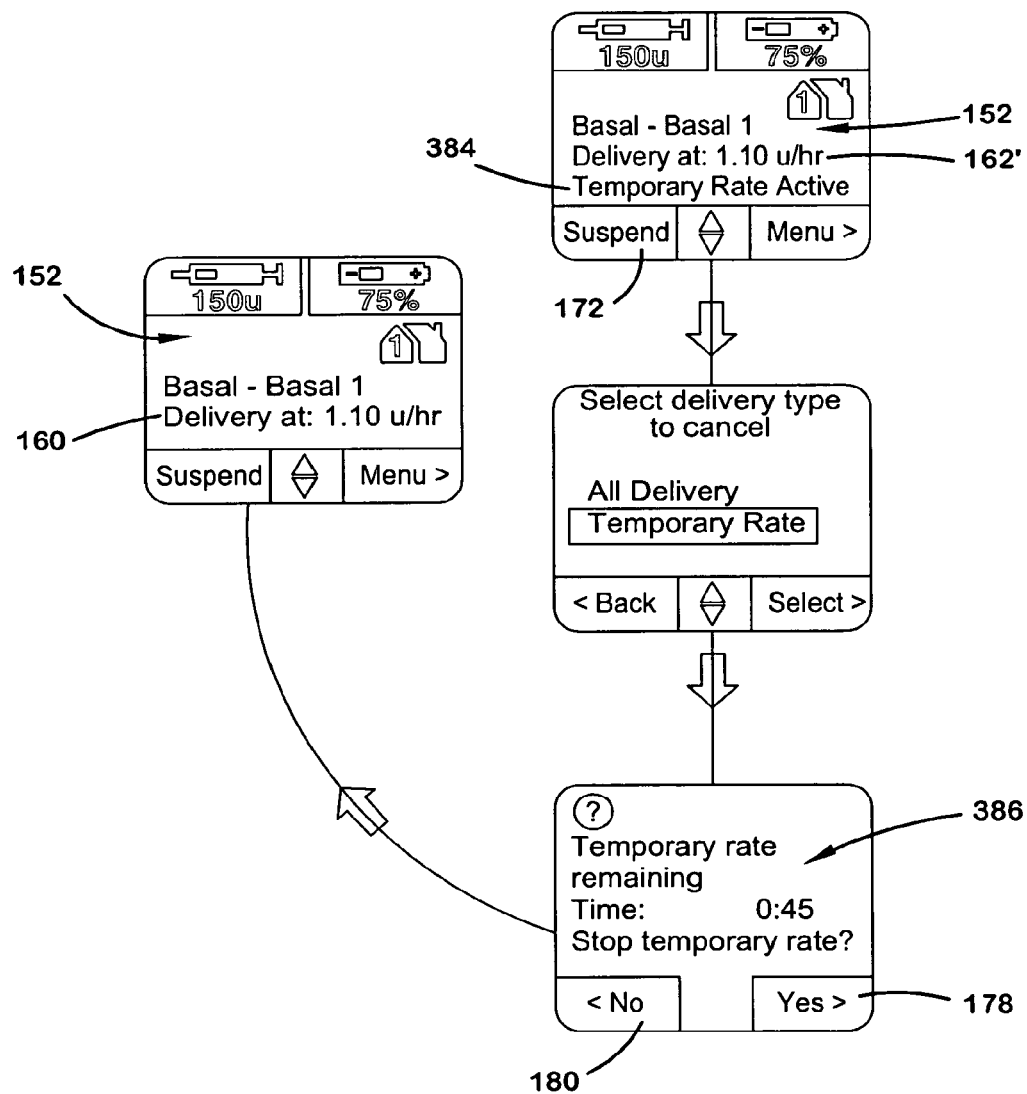

Referring to FIG. 17, the user can suspend an active temporary rate program by activating the Suspend function 172 on the home page 152. As described above, the pump 100 prompts the user to select suspension of all delivery or just the temporary rate. The user highlights and selects the temporary rate. The pump 100 then prints a banner 386 indicating how much time remains in the duration of the temporary rate and prompting the user to confirm suspension. The user confirms suspension by activating the yes function 178. The pump 100 then suspends delivery at the temporary rate and returns to pumping that according to the normal basal rate 160. If the user activates the no function 180, the pump 100 will continue delivering according to the temporary rate and will return to the home page 152 with a banner 384 stating that the temporary rate is active and a display of the temporary basal rate 162'.

L. Correction Bolus

In addition to delivering a basal rate the pump 100 may administer a bolus to lower the user's blood glucose level. One possible embodiment of the pump 100 can deliver two types of boluses, a correction bolus and a meal bolus. The correction bolus delivers a dose of insulin over and above the basal rate to lower or correct the user's blood glucose level if it becomes too high. A meal bolus is a dose of insulin delivered in anticipation of consuming a meal to counteract the effects that the meal may have on the user's blood glucose.

Figure 18:
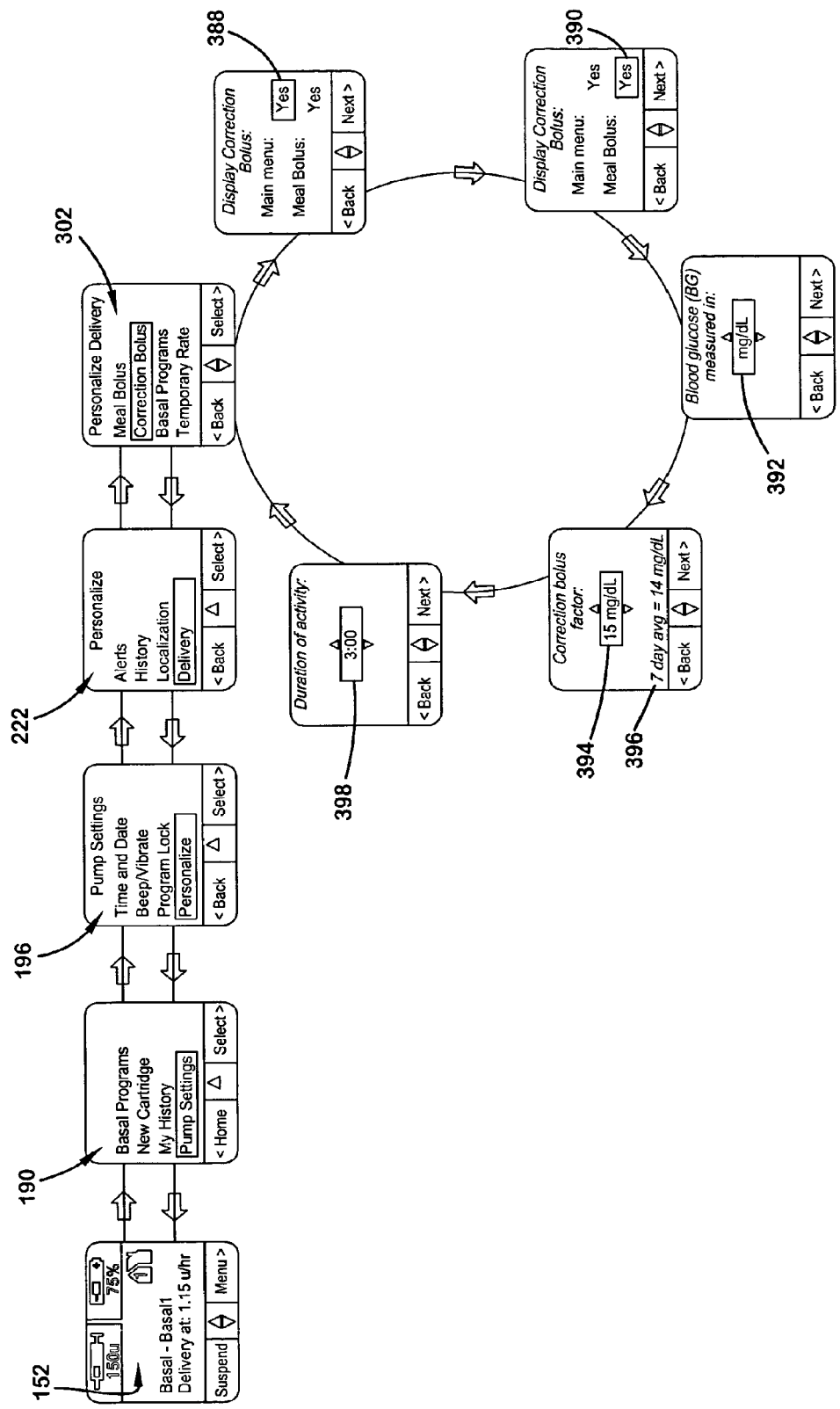
FIGS. 18 and 19 illustrate setting the operational parameters for the correction bolus delivery programs executed by the pump shown in FIGS. 1 and 2.

Referring to FIG. 18, the user can personalize or customize the correction bolus program and how the program is presented in the user interface. To personalize the temporary rate programs, the user accesses the Personalize Delivery submenu 302.

Selecting the Correction Bolus menu item causes the pump 100 to display a main-menu field 388, and places it in focus. The user scrolls to and selects either a yes value or a no value. The yes value enables a Correction Bolus menu item in the main menu 190, and a no value disables the Correction Bolus menu item in the main menu 190. Upon selecting the yes or no value, focus indexes to a meal-bolus field 390 in which the user scrolls to and selects either a yes value or a no value. A yes value enables the user to set a correction bolus through the meal bolus delivery program as described below. A no value disables the ability to set a correction bolus through the meal bolus delivery program.

Upon selecting a yes or no value in the meal-bolus field 390, focus indexes to a units field 392 in which the user scrolls to and selects units for measuring blood glucose levels in either mg/dL and mmol/L. Upon selecting the units, focus indexes to a correction-bolus-factor field 394 in which the user scrolls to and selects a desired correction factor. The correction factor is the amount that the user's blood glucose drops for each unit of delivered insulin. In one possible embodiment, the user scrolls through values ranging from 5 mg/dL to 200 mg/dL (or 0.2 mmol/L to 12 mmol/L). When the desired correction factor is set, focus indexes to a duration-of-activity field 398.

Additionally, the pump 100 calculates the average correction value for a predetermined number of days beginning with the previous day and extending backwards in time, and then displays 396 the average correction factor together with the correction-bolus-factor field 394. In the illustrated example, the pump 100 displays the average correction factor for the previous seven days. As discussed above, other embodiments average the correction factor over other periods of time. In yet other embodiments the user can select the period of time over which to average the correction factor. Within the duration-of-activity field 398, the user scrolls to and selects the duration of time over which insulin remains in the user's body. This amount will vary from user to user depending on a variety of factors including physical traits of the user and the type of insulin that is used. In one possible embodiment, the user scrolls through durations in the range from 2 hours to 6 hours. When the duration is set, the pump 100 returns to the Personalize Delivery submenu 302.

Figure 19:
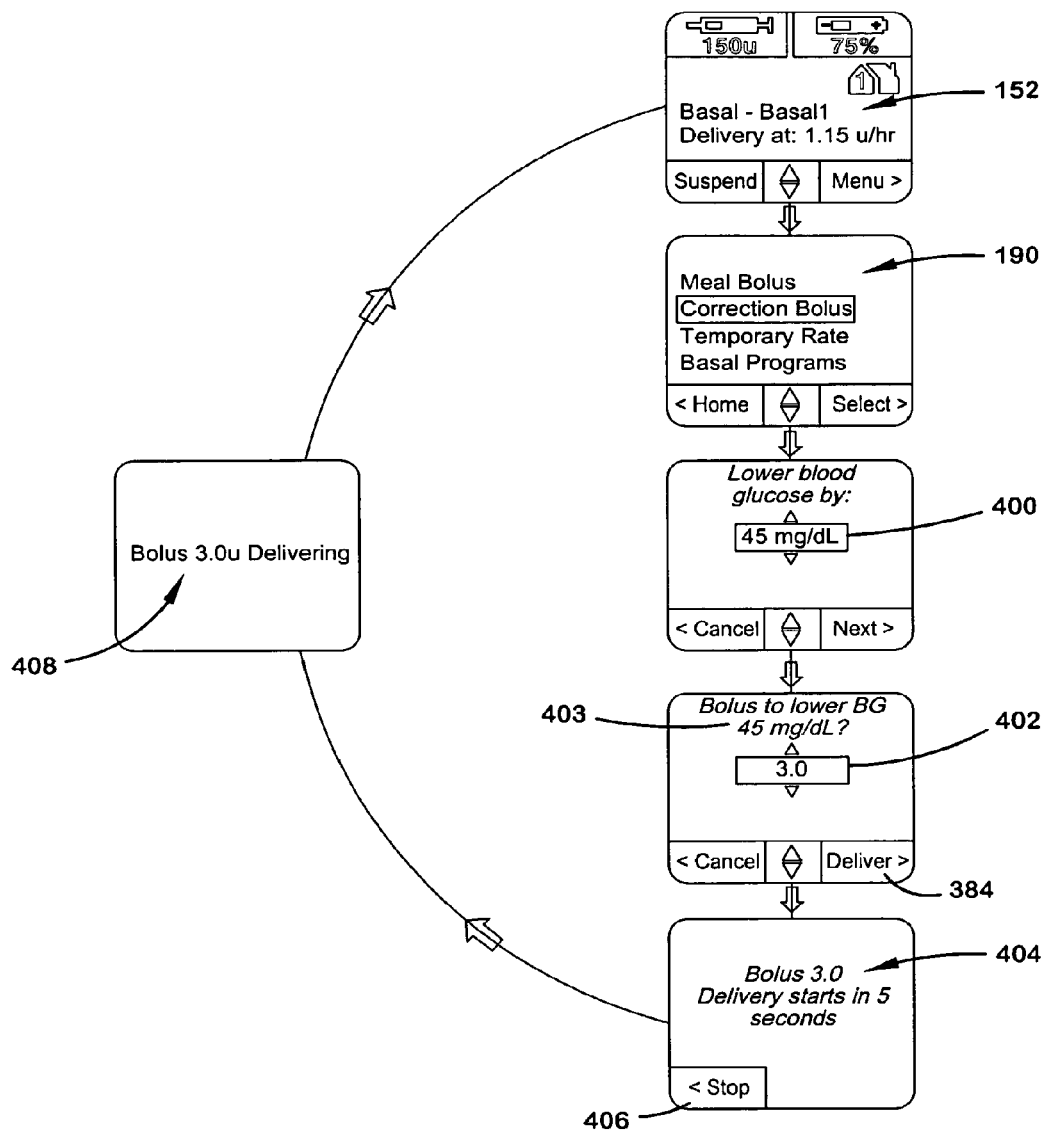

Referring now to FIG. 19, the user delivers a correction bolus by selecting the correction bolus menu item from the main menu 190. The pump 100 then displays an amount field 400 in which the user enters the amount by which they would like to lower their blood glucose. The user scrolls to and selects the desired amount. The pump 100 then calculates a recommended bolus and indexes focus to a recommend-bolus field 402. The pump 100 also displays a banner 403 with the recommend-bolus field 402 which reads "Bolus to Lower BG X?" where X is the amount that the user entered to lower his or her blood glucose. The pump 100 calculates the recommended bolus according to the equation:

$$\text{Correction Bolus} = \frac{\text{Drop in Glucose Level}}{\text{Correction Factor}} \tag{1}$$

and displays the recommended correction bolus in the recommend-bolus field 402. The user can adjust the recommended correction bolus by incrementing the recommend amount up or down using the up and down keys 142 and 144, respectively.

When the desired correction bolus is displayed in the recommend-bolus field 402, the user activates the Deliver function 384 and the pump 100 presents a verification display 404 that presents the bolus amount and a countdown timer. The pump 100 also assigns a stop function 406 to the first function key 138. The pump 100 then counts down a predetermined period of time, such as 5 seconds, and begins to deliver the bolus after the countdown timer times out. If the user activates the Stop function 406 while the timer is still counting down, the pump 100 will cancel delivery of the bolus and return to the home page 152.

During delivery of the bolus, the pump 100 displays a banner 408 in the screen stating the bolus is delivering and the amount of the bolus. The pump 100 then returns to the home page 152 after delivery of the bolus is complete.

Additionally, the pump 100 has a duration of activity program that determines whether any bolus that was previously delivered is still active. If a previous bolus is still active, the pump 100 calculates the estimated amount of insulin that is still active in the patient's body according to the equation:

$$\text{Residual Insulin} = \frac{\text{Last Bolus Amount} \times (\text{Duration} - \text{Time Since Last Bolus})}{\text{Duration}} \tag{2}$$

if (Duration−Time Since Last Bolus)≥0, otherwise Residual Insulin=0.
where Residual Insulin is the amount of insulin from a previous correction bolus still active within the user's body, Last Bolus Amount is the amount of the last correction bolus, Duration is the duration of insulin, which is set as described in conjunction with FIG. 15, and Time Since Last Bolus is the amount of time lapsed since the last correction bolus was delivered. Additionally, there could be more than one correction boluses still active within the user's body. In this situation, equation 2 is used to calculate the residual insulin from each of the still active correction boluses and the amount of residual insulin for each of the previous correction boluses is summed to determine Residual Insulin.

The pump 100 then calculates an adjusted correction bolus according to the equation:

$$\text{Reduced Correction Bolus} = \text{Correction Bolus} - \text{Residual Insulin} \tag{3}$$

The pump 100 then displays the reduced recommended corrected bolus in the correction-bolus field 402 rather than the recommended correction bolus. The display also presents a banner (not shown) with the recommended-bolus field that indicates that the recommended bolus is reduced to accommodate residual bolus insulin that is still working in the user's body. An example of such a banner is "*reduced for insulin on-board".

In an alternative embodiment, when the user selects the Correction Bolus menu item from the main menu 190, the pump 100 indexes to a display that presents the correction factor, displays the user's target blood glucose level, and displays a current-blood-glucose field that prompts the user to enter the user's current blood glucose level. The user scrolls to and selects their current blood glucose level. The pump 100 then calculates the appropriate amount of the bolus to lower the user's blood glucose level to the target value and then presents the verification display. In this embodiment, the pump 100 calculates the desired drop in the glucose level, and the pump 100 calculates the correction bolus according to the equation:

$$\text{Correction Bolus} = \frac{\text{Current Glucose Level} - \text{Target Glucose Level}}{\text{Correction Factor}} \tag{4}$$

M. Meal Bolus Programs

A meal bolus is a bolus that the pump delivers in anticipation of a meal that the user plans to consume. In one possible embodiment, the amount of the meal bolus is based on how much insulin is required to work against the carbohydrates that the user plans to consume. There are several types of meal bolus programs that the pump 100 may include. One type is a standard bolus in which the pump 100 delivers the meal bolus a predetermined time prior to when the user consumes the meal or snack. The standard program delivers the bolus at the maximum rate that the pump 100 is able to deliver it. As explained below, the standard program can be set for programming in either units of insulin or number of carbohydrates. Another type of meal bolus that the pump 100 can be programmed to deliver is an extended bolus in which the pump 100 delivers the meal bolus over an extended period. Yet another type of meal bolus that the pump 100 can be programmed to deliver is a combination bolus in which the pump 100 immediately delivers a portion of the meal bolus and the balance of the meal bolus over an extended period of time.

Figure 20:
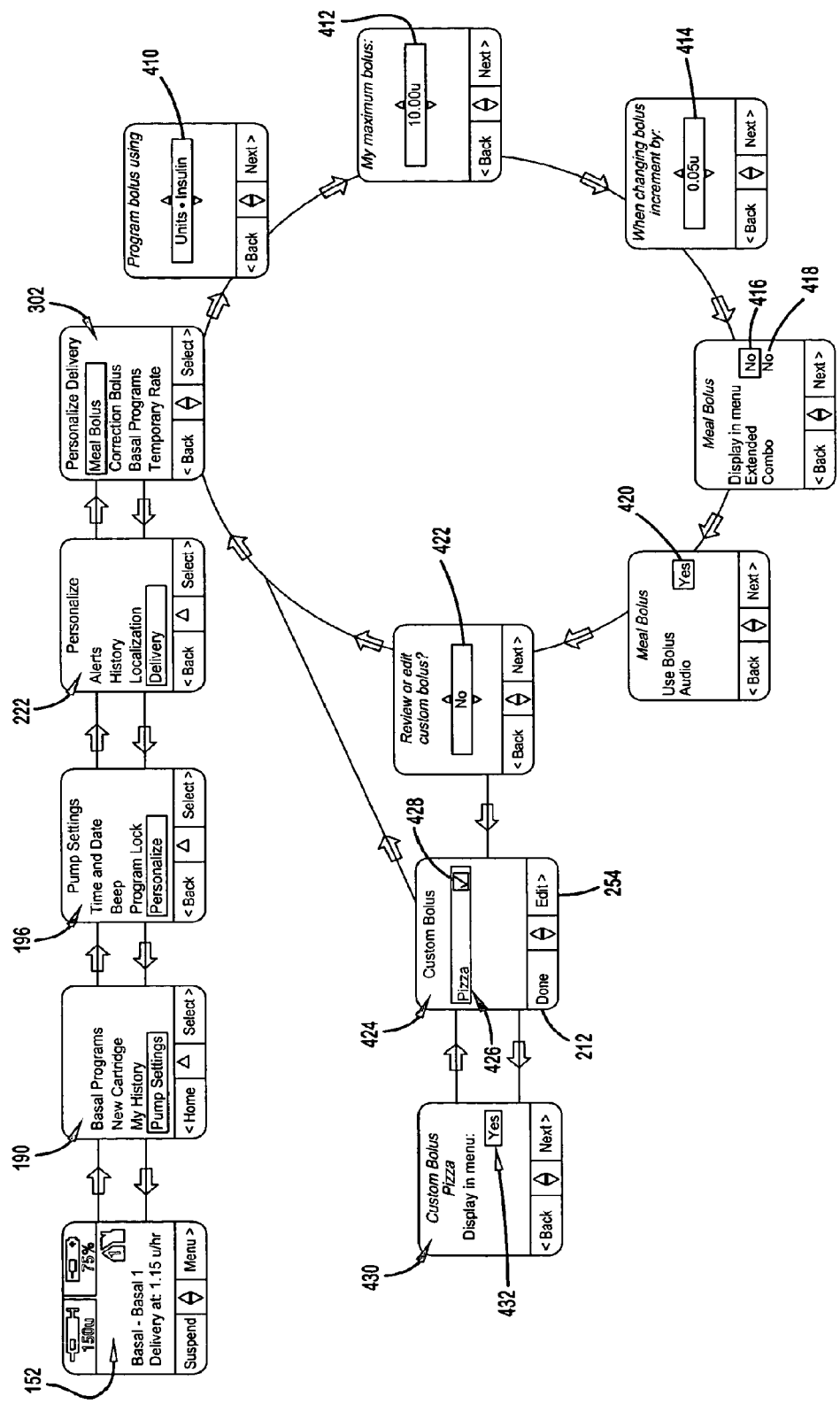
FIGS. 20-27 illustrate setting the operational parameters for the meal bolus delivery programs executed by the pump shown in FIGS. 1 and 2.

Referring to FIG. 20, to instruct the pump 100 to program the standard meal bolus in units of insulin and to otherwise personalize the meal bolus program, the user accesses the Personalize Delivery submenu 302. From the Personalize Delivery submenu 302, the user selects the Meal Bolus menu item and the pump 100 prompts 410 the user to select whether to program in units of insulin or carbohydrates. The user selects units of insulin. The pump 100 then prompts 412 the user to select the maximum bolus that can be delivered. In one possible embodiment, the user scrolls through values in the range between 0 units and 40 units of insulin in increments of 1 until the desired value is highlighted. Next, the pump 100 prompts 414 the user to select the increments in which the user can select the actual bolus to be delivered. In one possible embodiment, the user scrolls between 0.05 units, 0.10 units, 0.50 units, and 1.00 units.

Figure 21:
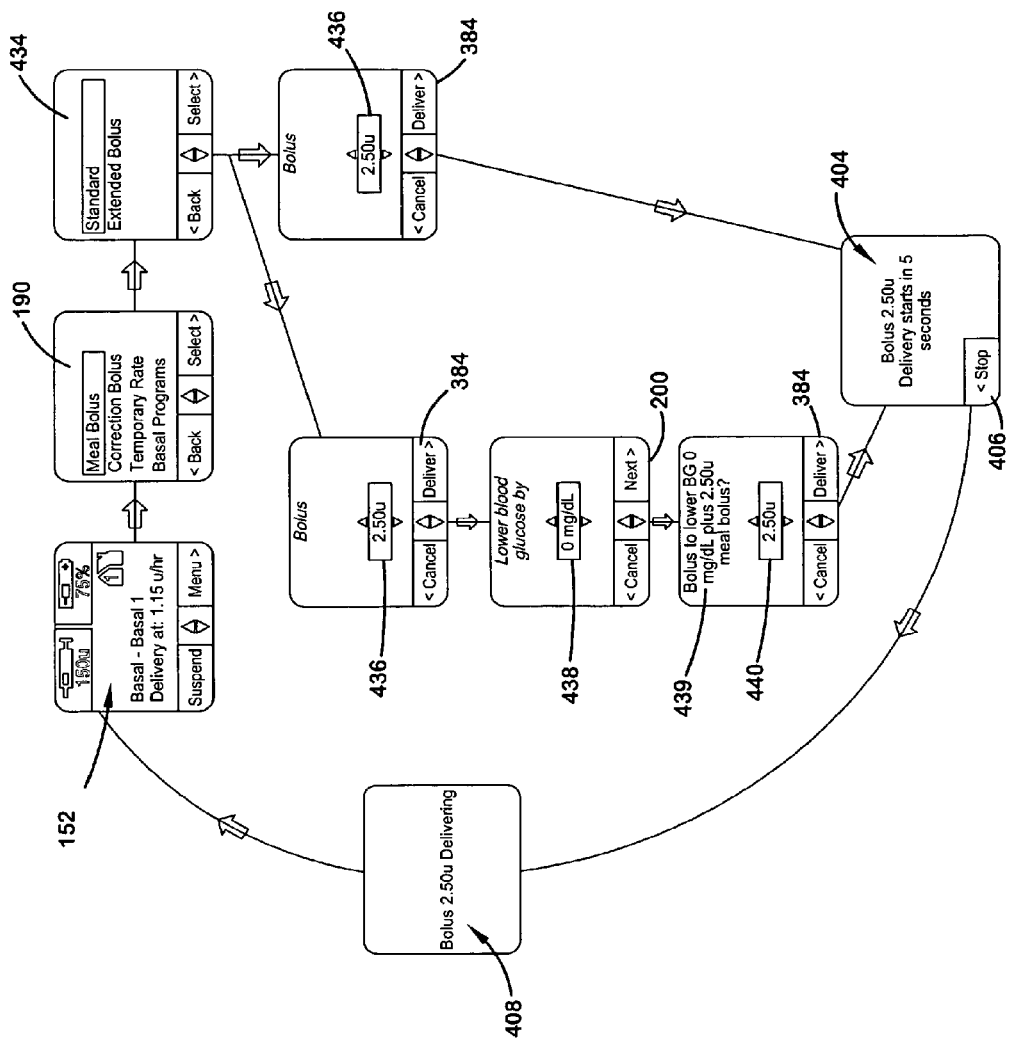

The pump 100 then prompts 416 the user to select whether to enable an extended bolus program and to display an Extended Bolus menu item within a Meal Bolus submenu 434 (FIG. 21). The extended bolus program is selected by selecting a yes value and disabled by selecting a no value. The pump 100 also prompts 418 the user to select whether to enable a combination bolus program and to display a Combo Bolus menu item within the Meal Bolus submenu 434. The combination bolus program is activated by selecting a yes value and is disabled by selecting a no value. The pump 100 then prompts 420 the user to choose whether to enable an audio bolus program. The user selects a yes value to enable the audio bolus program and selects a no value to disable the audio bolus program.

If the pump 100 is preprogrammed with one or more custom meal boluses, the pump prompts 422 the user to select whether to review or edit a custom bolus. If the user does not want to review or edit a custom bolus, the user selects no and the pump 100 returns to the Personalize Delivery submenu 302. If the user selects yes, the pump 100 presents a display 424 entitled "Custom Bolus," which lists the names 426 of the available custom meal bolus programs. The display 424 also presents a check box 428 for each of the custom meal bolus programs 426. If a custom meal bolus program 426 is enabled, the check box 428 is set. If a custom meal bolus program 426 is not enabled, the check box 428 is cleared. When a custom meal bolus is enabled, it is displayed in the Meal Bolus submenu 434 as a separate menu item. If the custom meal bolus program is not enabled, it is not displayed in the Meal Bolus submenu 434 and the user cannot execute the program.

To enable or disable a meal bolus program, the user scrolls to the desired custom meal bolus program and activates the Edit function 254. The pump 100 presents a display 430 entitled "Custom Bolus: X," where X is the name of the selected custom meal bolus program. In the illustrated example, the title of the display is Custom Meal Bolus: Pizza". Upon activating the Edit function 254, the pump 100 prompts 432 the user to select either a yes value or no value. If the user selects the yes value, the pump 100 enables the custom meal bolus program 426 and displays the name of the program as a menu item in the Meal Bolus submenu 434. If the user selects the no value, the pump 100 disables the custom meal bolus program 426 and does not display the name of the program as menu item in the Meal Bolus submenu 434. After the yes or no value is selected, the pump 100 returns to the "Custom Bolus" display 424.

The user repeats this procedure from the "Custom Bolus" display 424 for each custom meal bolus program 426 for which they desire to change the enabled state. When the user is done changing the enabled states for the available custom meal bolus programs 426, the user activates the Done function 212 in the "Custom Bolus" display 424. The pump 100 then returns to the Personalize Delivery submenu 302.

Additionally, in one possible embodiment, if there are no custom meal bolus programs available for the user to enable, the pump 100 automatically returns to the Personalize Delivery submenu 302 after the user instructs 420 the pump 100 whether to enable an Audio Bolus.

FIG. 21 illustrates administration of a standard meal bolus when the pump 100 is set to program meal boluses using units of insulin. The user selects the meal bolus menu item from the main menu, and the pump indexes to a Meal Bolus submenu 434. The meal bolus submenu 434 lists the available meal bolus programs. Examples include the standard meal bolus program, the extended meal bolus program, the combination meal bolus program, and any enabled custom meal bolus programs. In the illustrated example, only the extended meal bolus program is enabled and thus the Meal Bolus submenu 434 includes a Standard Bolus and an Extended Bolus. The user highlights the Standard Menu item and the pump 100 prompts 436 the user to enter the number of units to deliver. In one possible embodiment, the user can scroll through values in the range from 0 units to 17 units in increments of 0.5 units.

If the pump 100 is programmed to enable administration of a correction bolus through the Meal Bolus program, the pump 100 prompts 436 the user to enter the number of units to deliver as a meal bolus. The user then activates the Deliver function 384 and the pump 100 prompts 438 the user to enter the amount by which they want to lower their blood glucose level. In one possible embodiment, the user enters the amount by scrolling through values in units of either mg/dL or mmol/L. When the desired drop in blood glucose is entered, the user activates the Next function 200, which causes the pump 100 to calculate a recommended bolus amount and to display a user interface with the banner 439 stating "Bolus to Lower BG X plus Y meal bolus." X is the amount the user entered to lower the blood glucose level, and Y is the amount of the meal bolus entered by the user.

The user interface also displays the recommended bolus amount 440 to deliver. The recommended bolus amount 440 is the recommended correction bolus as calculated above, plus the amount of the meal bolus. This feature allows the user to correct a high blood glucose level and deliver additional insulin to work against carbohydrates that they plan to consume. The user can adjust the recommended bolus amount by increasing or decreasing the recommended bolus amount by scrolling up or down. In one possible embodiment, the user scrolls in increments of 0.5 units. Once the desired bolus amount is set, the user activates the Deliver function 384.

Activating the Deliver function 384 causes the pump 100 to start a countdown timer and display a banner 404 that states a bolus will be delivered in predetermined time. In one possible embodiment, that time is 5 seconds and the pump 100 displays the bolus amount in the banner 404. An example of a possible banner states "Bolus X Delivery Starts in 5 Seconds," where X is the bolus amount. The pump 100 also assigns a Stop function 406 to the first function key 138.

If the user activates the Stop function 406 before the countdown timer times out, the pump 100 will terminate delivery of the bolus and return to the home page 152. If the user does not activate the Stop function 406, when the timer times out, the pump 100 will begin to deliver the bolus and display a banner 408 stating that the bolus is being delivered. An example of such a banner is "Bolus X is Delivering", where X is the bolus amount. When delivery of the bolus is complete, the pump 100 returns to the home page 152.

In an alternative embodiment, when the pump 100 is programmed to enable administration of a correction bolus through a Meal Bolus, the pump 100 displays a user interface entitled Current Blood Glucose." The pump 100 calculates the current correction factor and displays the correction factor in the user interface. The pump 100 also displays the target blood glucose level. The user then enters his or her current blood glucose level in units of either mg/dL or mmol/L, by scrolling through a range of values until the current blood glucose level is displayed. In this embodiment, the target blood glucose level and the appropriate units are programmed into the pump 100 when personalizing the correction bolus program as described herein. Once the user enters the current blood glucose level, the user activates the Next function 200 and the pump 100 calculates a recommended bolus amount, using the equations set forth above, and adds it to the meal bolus. The pump 100 displays the user interface with the banner "Bolus to Lower BG X plus Y Meal Bolus" 439. The user can then change the amount 440 and activate the Deliver function 384 to begin delivery of the bolus as described above.

Additionally, in one possible embodiment, the pump 100 adjusts the recommended bolus based on the meal bolus or the meal bolus plus the correction bolus to accommodate insulin on board or residual insulin that is still working within the user's body. In this embodiment, the amount of the adjusted correction bolus is adjusted using the equations described above in conjunction with the duration-of-activity function. The methods of adjusting the bolus amount for insulin on board is described above.

Figure 22:
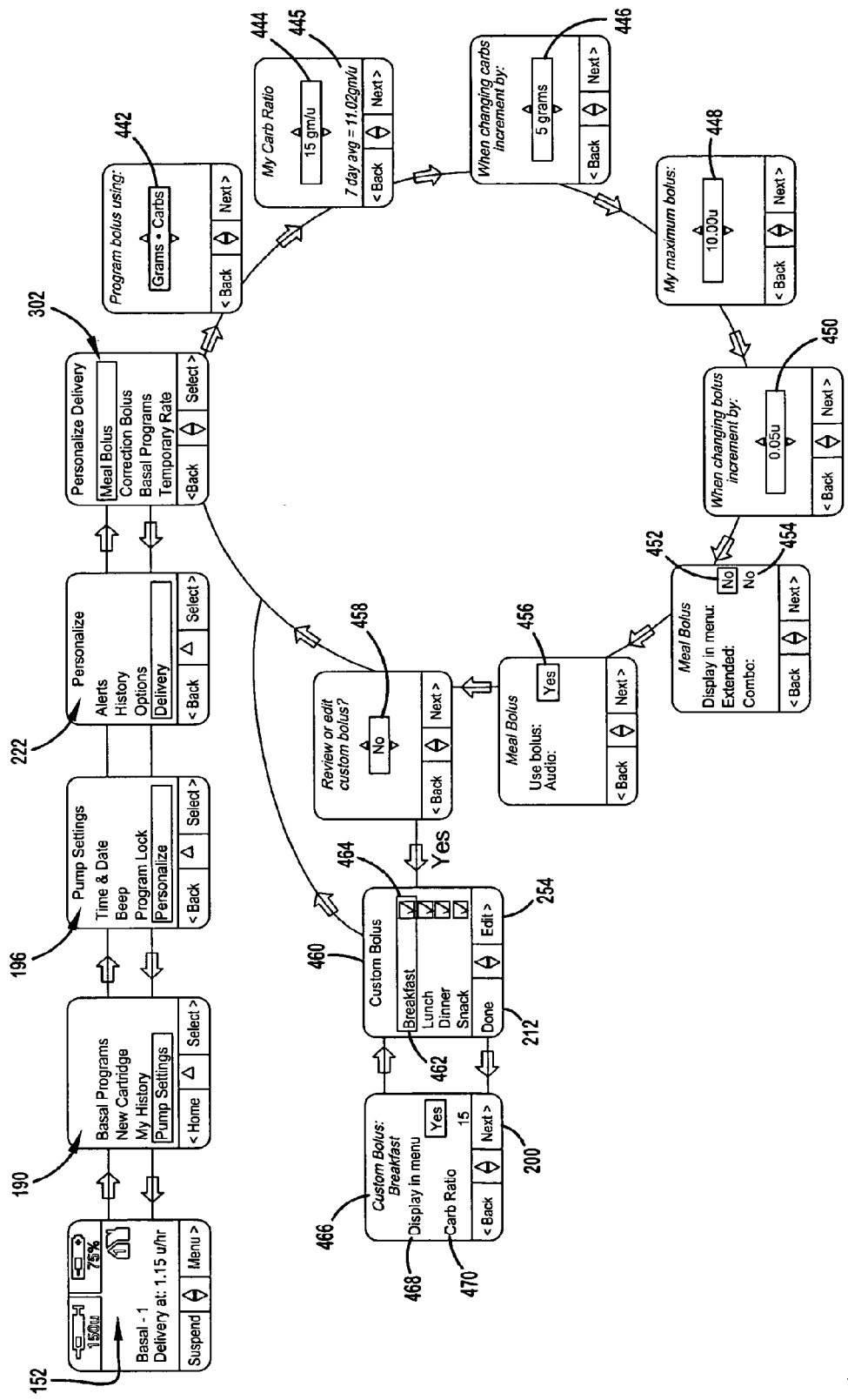

Referring to FIG. 22, to instruct the pump 100 to program the standard meal bolus in number of carbohydrates consumed and to otherwise personalize the meal bolus program, the user accesses the Personalize Delivery submenu 302. From the Personalize Delivery submenu 302, the user selects the Meal Bolus menu item and the pump 100 then prompts 442 the user to select whether to program in units of insulin or carbohydrates. The user highlights units of carbohydrates and activates the Next function 200. The pump 100 prompts 444 the user to enter their carbohydrate ratio, which is the number or grams of carbohydrates that each unit of insulin will counteract. The pump 100 also calculates the historical average carbohydrate ratio 445 for a predetermined time-period and displays that historical average with the prompt 444. In one possible embodiment, the historical average is for the previous 7-day period. As discussed above, other embodiments average the carbohydrate ratio over other periods of time. In yet other embodiments the user can select the period of time over which to average the carbohydrate ratio.

The user enters the carbohydrate ratio by scrolling through values in a predetermined range such as from 0 gm/u to 50 gm/u in increments of 1. When the desired number of carbohydrates is set, the user activates the Next function 200 and the pump 100 prompts 446 the user to set the increment by which the user would like to be able to scroll through the number of carbohydrates when programming the pump 100 to deliver a meal bolus. In one possible embodiment, the user can set the desired increment between 1 and 15 grams.

The pump 100 prompts 448 the user to enter the maximum bolus that can be delivered. In one possible embodiment, the user scrolls through values in the range between 0 units and 40 units of insulin in increments of 1 until the desired value is highlighted. The pump 100 then prompts 450 the user to enter the increments in which the user can select the actual bolus to be delivered. In one possible embodiment, the user scrolls between 0.05 units, 0.10 units, 0.50 units, and 1.00 units and activates the Next function 200.

The pump prompts 452 the user to select whether to enable an extended bolus program and to display an Extended Bolus menu item within the Meal Bolus submenu 434. The extended bolus program is enabled by highlighting and activating a yes value and not enabled by highlighting and selecting a no value. The pump 100 also prompts 454 the user to select whether to enable a combination bolus program and to display a Combo Bolus menu item within a Meal Bolus submenu 434. The combination bolus program is enabled by highlighting and activating a yes value and not enabled by highlighting and selecting a no value. The user activates the Next function 200 to index through these prompts 452 and 454. The pump 100 then prompts 456 the user to choose whether to enable an audio bolus program. The user selects a yes value to enable the audio bolus program and selects a no value to not enable the audio bolus program and then activates the next function 200.

If the pump 100 is preprogrammed with one or more custom meal boluses, the pump 100 then prompts 458 the user to select whether to review or edit a custom bolus. If the user does not want to review or edit a custom bolus, the user selects no and the pump 100 returns to the Personalize Delivery submenu 302. If the user selects yes, the pump indexes to a display 460 entitled "Custom Bolus," which lists the names 462 of the available custom programs. In the illustrated example, there are four custom boluses available on the pump, Breakfast, Lunch, Dinner, and Snack.

The screen also presents a check box 464 for each of the custom meal bolus programs 462. If a custom meal bolus program is enabled, the pump 100 sets the check box 464. If a custom meal bolus program is not enabled, the pump 100 clears the check box 464. When a custom meal bolus program is enabled, it is displayed in the Meal Bolus submenu 434 as a separate menu item. If the custom meal bolus program is not enabled, it is not displayed in the Meal Bolus submenu 434 and the user cannot execute the custom meal bolus program.

To enable or disable a custom meal bolus program, the user selects the desired custom meal bolus program and activates the Edit function 254. The pump 100 indexes to a display 466 entitled "Custom Bolus: X," where X is the name 462 of the selected custom meal bolus program. In the illustrated example, the title of the display 466 is Custom Meal Bolus: Breakfast". The user interface 466 prompts 468 the user to instruct the pump 100 whether to display the custom meal bolus in the Meal Bolus submenu 434 by entering either a yes value or no value. If the user selects the yes value and activates the next function 200, the pump 100 prompts 470 the user to enter the carbohydrate ratio to use with the custom meal bolus program. The value of the carbohydrate ratio 470 may or may not be the same value as the carbohydrate ratio 444. The user enters the carbohydrate ratio by scrolling through values in a predetermined range such as from 0 gm/u to 50 gm/u in increments of 1. When the desired number of carbohydrates is set, the user activates the Next function 200 and the pump 100 returns to the "Custom Bolus" submenu 434.

If the user selects the no value at the prompt 468, the pump 100 will not enable the custom meal bolus program and will not display menu item for the program in the Meal Bolus submenu 434. After the no value is entered, the pump 100 returns to the "Custom Bolus" display 460.

The user repeats this procedure from the "Custom Bolus" display 460 for each custom bolus program for which they desire to change the enabled state. When the user is done changing the enabled states for the available custom meal bolus programs, the user activates the Done function 212. The pump 100 then returns to the Personalize Delivery submenu 302.

Additionally, in one possible embodiment, if there are no custom meal bolus programs available for the user to enable, the pump 100 automatically returns to the Personalize Delivery submenu 302 after the user instructs 456 the pump 100 whether to enable an Audio Bolus.

Figure 23:
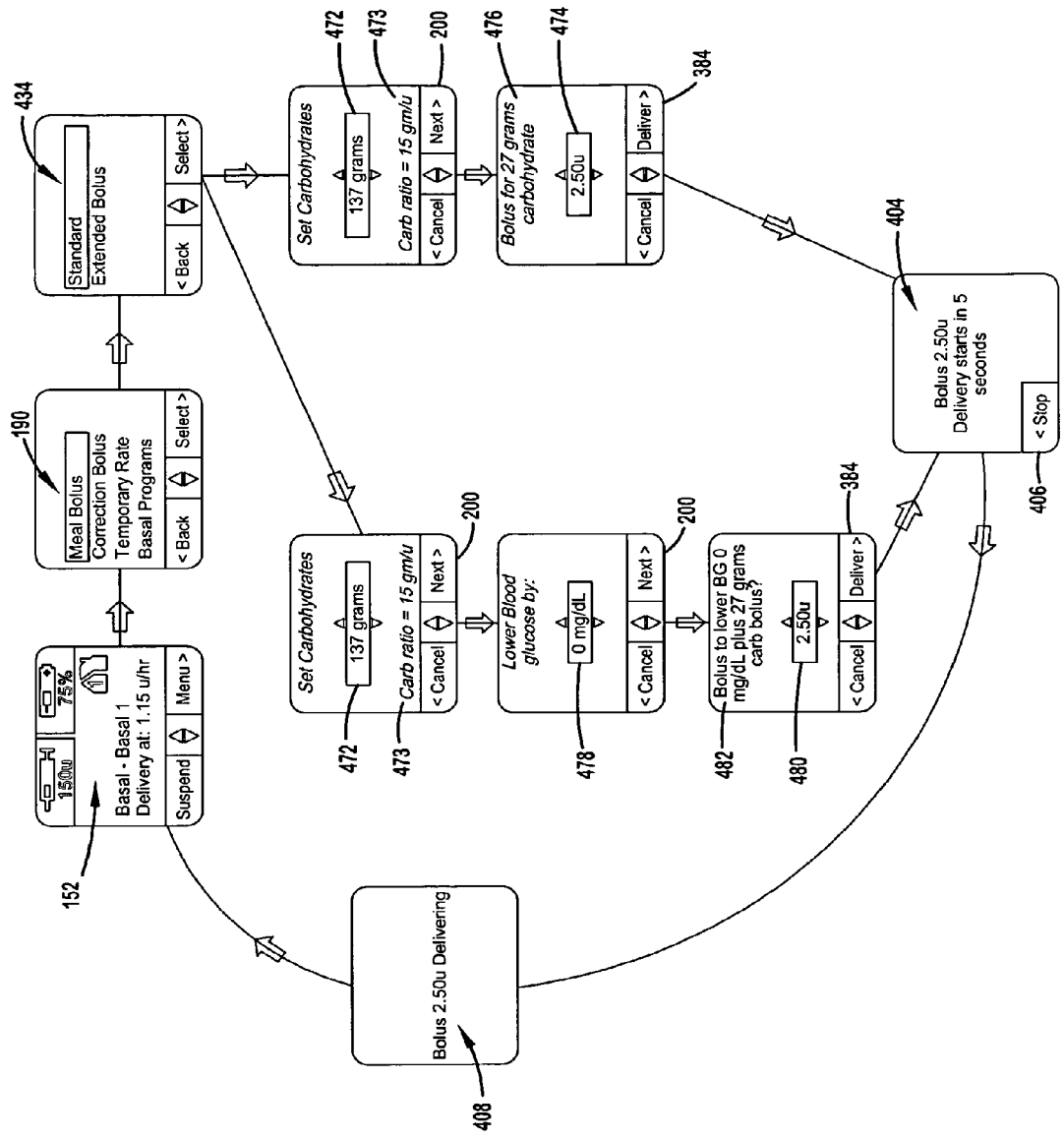

FIG. 23 illustrates administration of a standard meal bolus when the pump 100 is set to program meal boluses using grams of carbohydrates. The user selects the meal bolus menu item from the main menu 190, and the pump indexes to the Meal Bolus submenu 434. The meal bolus submenu 434 lists the available meal bolus programs. Examples include the standard meal bolus program, the extended meal bolus program, the combination meal bolus program, and any enabled custom meal bolus programs. In the illustrated example, only the extended meal bolus program is enabled and thus the meal bolus submenu includes a Standard Bolus and an Extended Bolus.

The user selects the Standard Menu item and the pump 100 prompts 472 the user to enter the number of carbohydrates that the user plans to consume. The user interface also displays the current carbohydrate ratio 473. The user sets the desired number of carbohydrates. In one possible embodiment, the user scrolls through carbohydrates in the range from 0 grams to 225 grams.

The user then activates the Next function 200 and the pump 100 calculates a recommended size for the meal bolus using the equation:

$$\text{Recommended Meal Bolus} = \frac{\text{Grams of Carbohydrates}}{\text{Carbohydrate Ratio}} \quad (5)$$

The pump 100 displays 474 the recommended meal bolus. The user can then adjust the size of the meal bolus by scrolling up or down. In one possible embodiment, the pump 100 scrolls in increments of 1. Once the desired bolus amount is set the user activates the Deliver function 384.

When the pump 100 is programmed to enable administration of a correction bolus through a Meal Bolus, the pump 100 prompts 472 the user to enter the number of carbohydrates to be consumed. The user then activates the Next function 200, and the pump 100 prompts 478 the user to enter the amount by which they want to lower their blood glucose level. The user then activates the Next function 200, which causes the pump 100 to calculate a recommended bolus amount and to display a user interface with a banner 482 stating "Bolus to Lower BG X plus Y grams of carbohydrates." X is the amount by which the user entered to lower the blood glucose level, and Y is the number of carbohydrates that the user entered.

The pump 100 also displays the recommended bolus amount 480 to deliver. The recommended bolus amount 480 is the recommended correction bolus plus the amount of the meal bolus. This feature allows the user to correct a high blood glucose level and deliver additional insulin to work against carbohydrates that they plan to consume. The user can adjust the recommended bolus amount by increasing or decreasing the recommended bolus amount by scrolling up or down. In one possible embodiment, the user scrolls in increments of 0.5 units. Once the desired bolus amount is set, the user activates the Deliver function 384.

Activating the Deliver function 384 causes the pump 100 to start the countdown timer and display the banner 404 that states a bolus will be delivered in predetermined time. In one possible embodiment, that time is 5 seconds and the banner 404 also states the bolus amount. An example of a possible banner 404 states "Bolus X Delivery Starts in 5 Seconds," where X is the bolus amount. The pump 100 also assigns a Stop function 406 to the first function key 138.

If the user activates the Stop function 406 before the countdown timer times out, the pump 100 will terminate delivery of the bolus and return to the home page 152. If the user does not activate the Stop function 406, when the timer times out, the pump 100 will begin to deliver the bolus and display the banner 408 stating that the bolus is being delivered. An example of such a banner is "Bolus X is Delivering", where X is the bolus amount. When delivery of the bolus is complete, the pump returns to the home page 152.

In an alternative embodiment, when the pump 100 is programmed to enable administration of a correction bolus through a Meal Bolus, the pump 100 prompts the user to enter their current blood glucose measurement. The pump 100 calculates the current correction factor and also displays the correction factor and the target blood glucose level with the prompt. The user then enters his or her current blood glucose level in units of either mg/dL or mmol/L, by scrolling through a range of values until the current blood glucose level is displayed. In this embodiment, the target blood glucose level and the appropriate units are programmed into the pump when personalizing or customizing the correction bolus program. Once the user enters the current blood glucose level, the user activates the Next function 200 and the pump 100 calculates a recommended bolus amount and adds it to the meal bolus. The pump 100 displays the user interface with the banner 482 "Bolus to Lower BG X plus Y grams of carbohydrates." The user can then change the amount and activate the Deliver function 384 to begin delivery of the bolus as described above.

Additionally, in one possible embodiment, the pump 100 adjusts the recommended bolus based on the meal bolus or the meal bolus plus the correction bolus to accommodate insulin on board or residual insulin that is still working within the user's body. In this embodiment, the amount of the adjusted correction bolus is adjusted using the equations described above in conjunction with the duration-of-activity function. The methods of adjusting the bolus amount for insulin on board is described herein.

Figure 24:
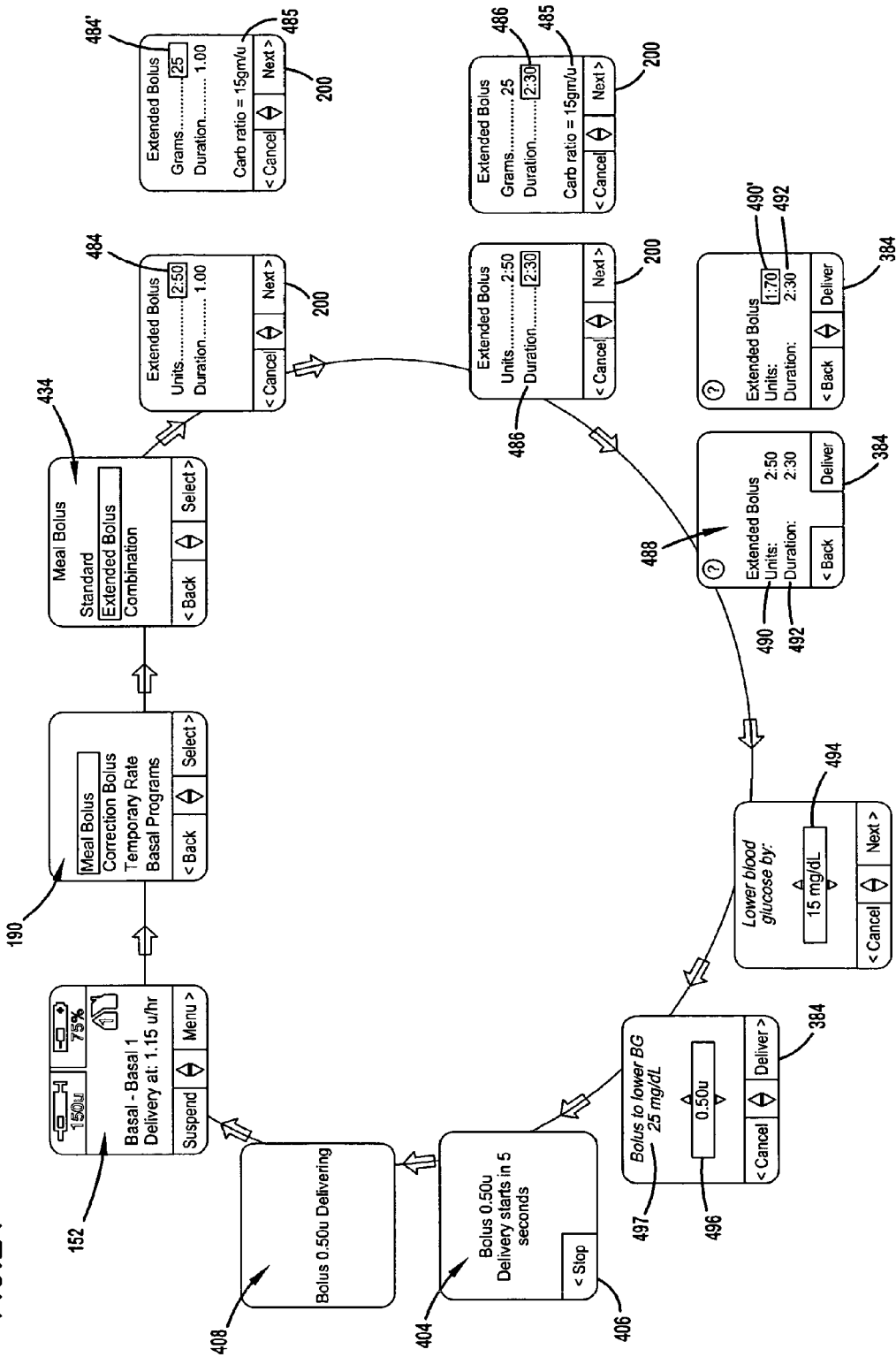

FIG. 24 illustrates administration of an extended bolus. The user selects the meal bolus menu item from the main menu 190, and the pump 100 indexes to a Meal Bolus submenu 434. The meal bolus submenu 434 lists the available meal bolus programs including the extended bolus program. In the illustrated example, the extended meal bolus program and the combination bolus program are enabled and thus the meal bolus submenu includes menu items for a standard bolus, an extended bolus, and a combination bolus.

The user selects the Extended Bolus menu item and, when the pump 100 is set to program in units of insulin, the pump prompts 484 the user to enter the number of units to deliver. In one possible embodiment, the user can scroll through values in the range from 0 units to 17 units in increments of 0.5 units. When the number of units for delivery are entered, the user activates the Next function 200 and the pump 100 prompts 486 the user to enter the duration of length of time over which the extended bolus is to be delivered. In one possible embodiment, the user enters a duration in the range of 0 minutes to 6 hours in increments of 30 minutes.

When the duration is set, the pump 100 displays a user interface 488 that presents the programmed amount 490 of the extended bolus and the duration 492 over which it is to be delivered. To begin delivery of the extended bolus, the user activates the Deliver function 384. The pump 100 then begins delivering the extended bolus and will complete delivery upon expiration of the duration.

Alternatively, when the pump 100 is set to program in grams of carbohydrates, the pump 100 prompts 484' the user to enter the grams of carbohydrates that the user plans to consume rather than the units of insulin to deliver as an extended bolus. The pump 100 also prompts 486 the user to enter the duration for the extended bolus. The pump 100 displays 485 the carbohydrate ratio while prompting the user to enter the grams of carbohydrates 484' and the duration 486. The pump 100 then calculates a recommended bolus amount 490' using the carbohydrate ratio as described above and displays the recommended bolus amount 490', together with the duration 492 in a user interface that confirms the parameters for delivery of the extended bolus. The user can adjust the recommended amount 490' for the extended bolus by scrolling with the up and down keys 142 and 144. The user activates the Deliver function 384 to begin delivery of the extended bolus using the parameters displayed in the user interface.

After delivery of the extended bolus begins, if the pump 100 is programmed to enable administration of a correction bolus through the Meal Bolus program, the pump 100 prompts 494 the user to enter the amount by which they want to lower their blood glucose level. The user then activates the Next function 200 and the pump 100 prompts 496 the user to enter the number of units to deliver as a meal bolus. In one possible embodiment, the user enters the amount by scrolling through values in units of either mg/dL or mmol/L. When the desired drop in blood glucose is entered, the user activates the Next function 200, which causes the pump 100 to calculate a recommended bolus amount and to display the banner 497 "Bolus to Lower BG X." X is the amount by which the user entered to lower the blood glucose level.

The prompt 496 initially displays the recommended bolus amount to deliver. The recommended bolus amount is the recommended correction bolus 490 or 490', which the pump 100 calculates using the correction factor as discussed above. This feature allows the user to correct a high blood glucose level and deliver additional insulin to work against carbohydrates that they plan to consume. The user can adjust the recommended bolus amount 496 by increasing or decreasing the recommended bolus amount 496 by using the up and down keys 142 and 144. In one possible embodiment, the user scrolls in increments of 0.5 units. Once the desired bolus amount is set, the user activates the Deliver function 384.

Activating the Deliver function 384 causes the pump 100 to display the banner 404 that states a bolus will be delivered in predetermined time. In one possible embodiment, that time is 5 seconds and the pump 100 displays the bolus amount 496 in the banner. An example of a possible user interface states "Bolus X Delivery Starts in 5 Seconds," where X is the amount of the correction bolus. The pump 100 also assigns the Stop function 406 to the first function key 138.

If the user activates the Stop function 406 before the countdown timer times out, the pump 100 will terminate delivery of the correction bolus and return to the home page 152. In one possible embodiment, activating the Stop function 406 will terminate delivery of the correction bolus, but not the extended bolus. If the user does not activate the Stop function 406, when the timer times out, the pump 100 will begin to deliver the bolus and display the banner 408 stating that the bolus is being delivered. An example of such a banner is "Bolus X is Delivering", where X is the bolus amount. When delivery of the bolus is complete, the pump 100 returns to the home page 152.

In an alternative embodiment, when the pump 100 is programmed to enable administration of a correction bolus through a Meal Bolus, the pump 100 prompts the user to enter their current blood glucose measurement. The pump 100 calculates the current correction factor and displays the correction factor in the user interface. The pump 100 also displays the target blood glucose level. The user then enters his or her current blood glucose level in units of either mg/dL or mmol/L, by scrolling through a range of values until the current blood glucose level is displayed. In this embodiment, the target blood glucose level and the appropriate units are programmed into the pump 100 when personalizing the correction bolus program. Once the user enters the current blood glucose level, the user activates the Next function 200 and the pump 100 calculates a recommended bolus amount and adds it to the meal bolus. The pump 100 displays the user interface with the banner "Bolus to Lower BG X plus Y Meal Bolus." The user can then change the amount and activate the Deliver function 384 to begin delivery of the bolus as described above.

Additionally, in one possible embodiment, the pump 100 adjusts the recommended correction bolus based on the meal bolus or the meal bolus plus the correction bolus to accommodate insulin on board or residual insulin that is still working within the user's body. In this embodiment, the amount of the adjusted correction bolus is adjusted using the equations described above in conjunction with the duration-of-activity function. The methods of adjusting the bolus amount for insulin on board is described herein.

Figure 25:
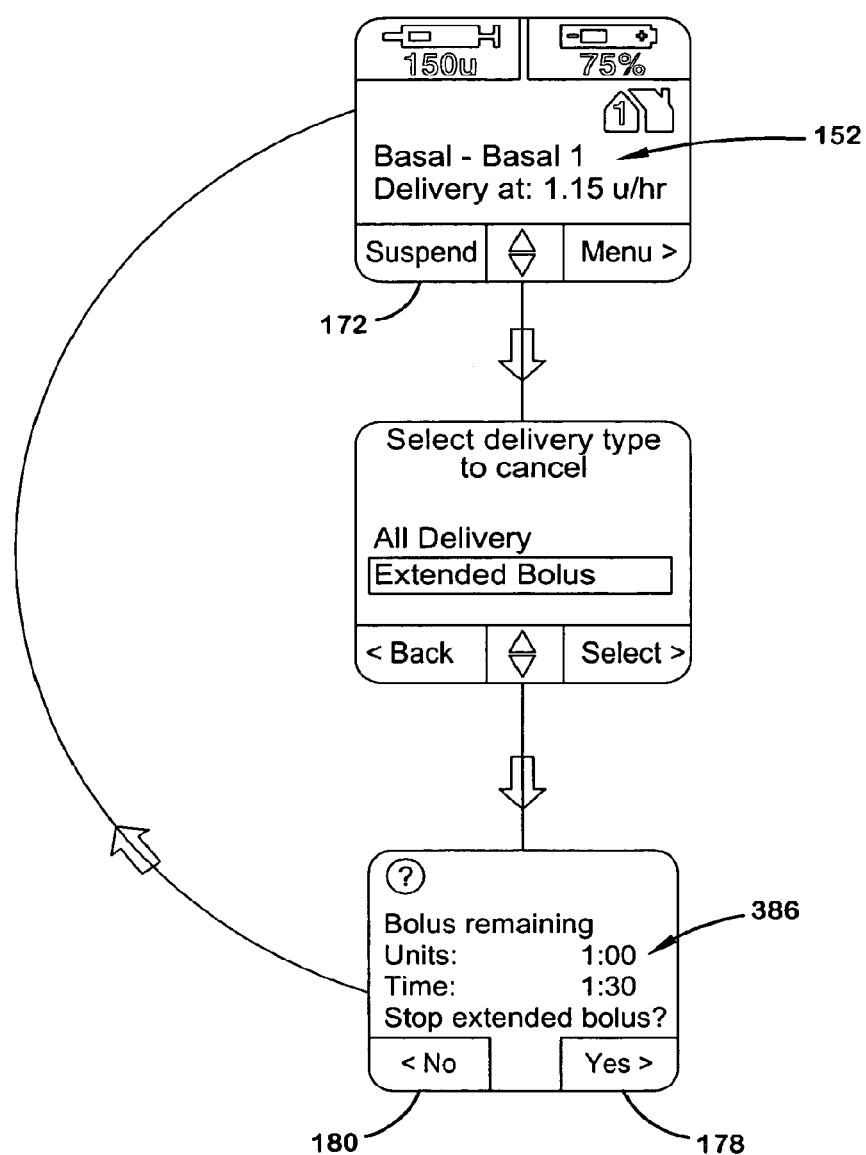

Referring to FIG. 25, the user can suspend delivery of an extended bolus by activating the Suspend function 172 on the home page 152. As described above, the pump 100 prompts the user to select suspension of all delivery or just the extended bolus. The user selects the extended bolus. The pump 100 then prints the banner 386 indicating how much time remains in the duration for the extended bolus and how much of the extended bolus remains to be delivered. The pump 100 also prompts the user to confirm suspension. The user confirms suspension by activating the Yes function 178. The pump 100 then suspends delivery of the extended bolus and returns to pumping according to the normal basal rate. If the user activates the No function 180, the pump 100 will continue delivering according to the extended bolus and will return to the home page 152.

Figure 26:
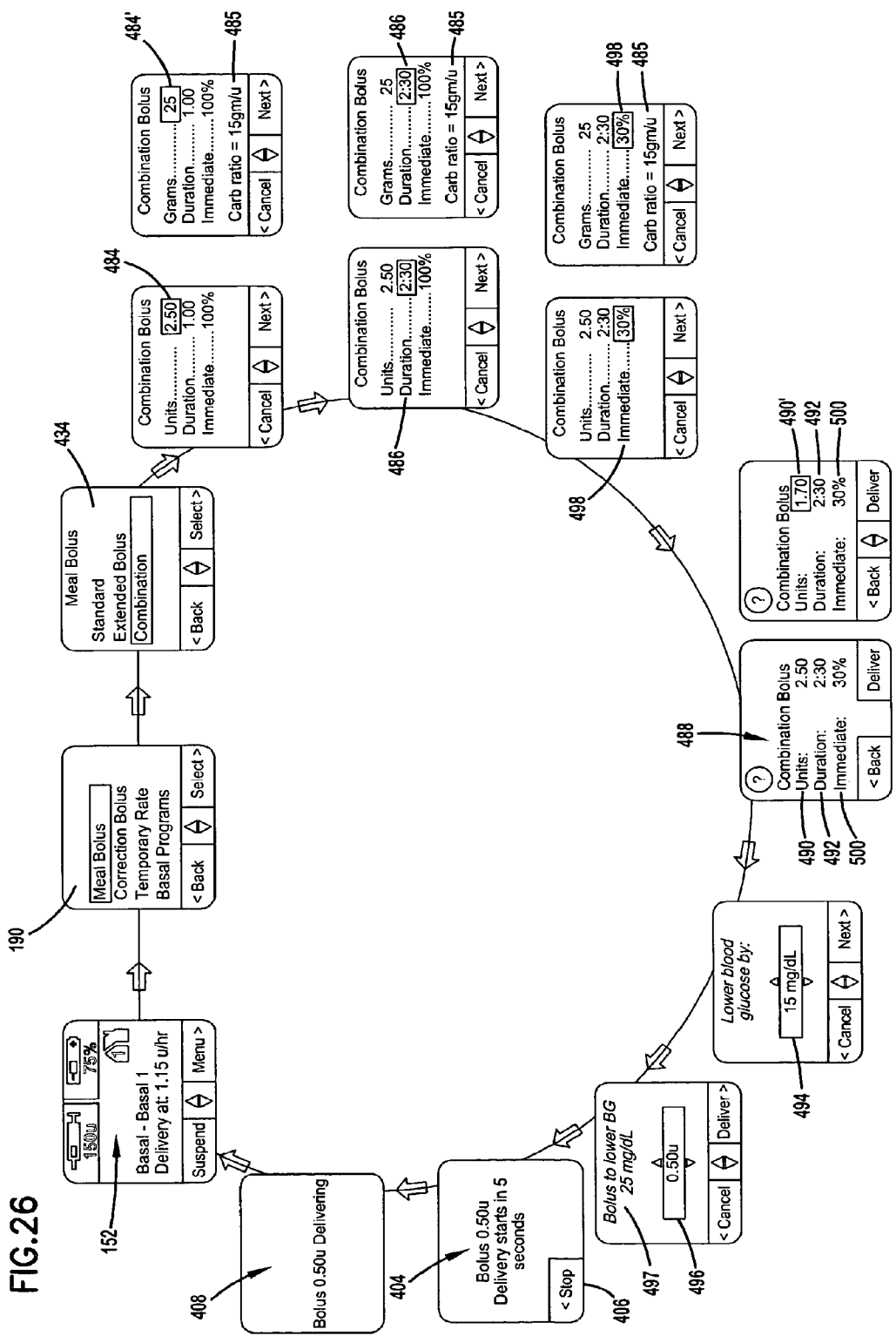

Referring to FIG. 26, delivery of a combination bolus is programmed into the pump in a manner similar to that of an extended bolus. However, the pump also prompts 498 the user to enter the proportion or percent of the bolus that the pump 100 delivers immediately upon activation of the Deliver function 384. To enter the proportion of the amount that is delivered immediately, the user scrolls through percentages until the desired percentage of the bolus for immediate delivery is set. In one possible embodiment, the user scrolls through percentages in the range from 0% to 100% in increments of 1. Additionally when programming the pump to deliver a combination bolus, the pump 100 displays 500 the percentage of the bolus that is to be delivered immediately in the confirmation user interface 488. In an alternative embodiment, the user enters the proportion or percent of the bolus that the pump 100 delivers over an extended period.

Figure 27:
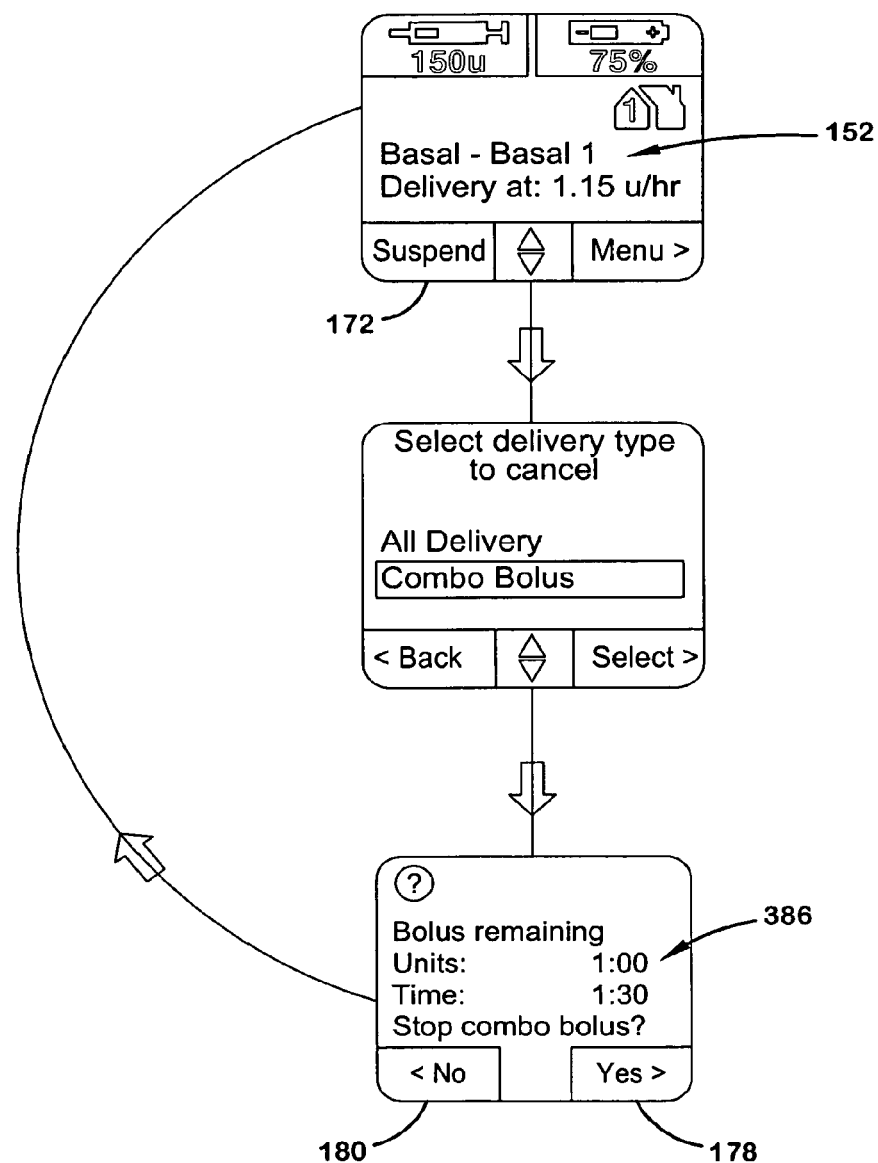

Referring to FIG. 27, the user can suspend delivery of a combination bolus in a manner substantially similar to that of the extended bolus except that the pump 100 displays a combination bolus menu item in the suspend menu. The user selects the combination bolus menu item to suspend delivery of the combination bolus, and then confirms suspension of the combination bolus.

N. Audio Bolus

Figure 28:
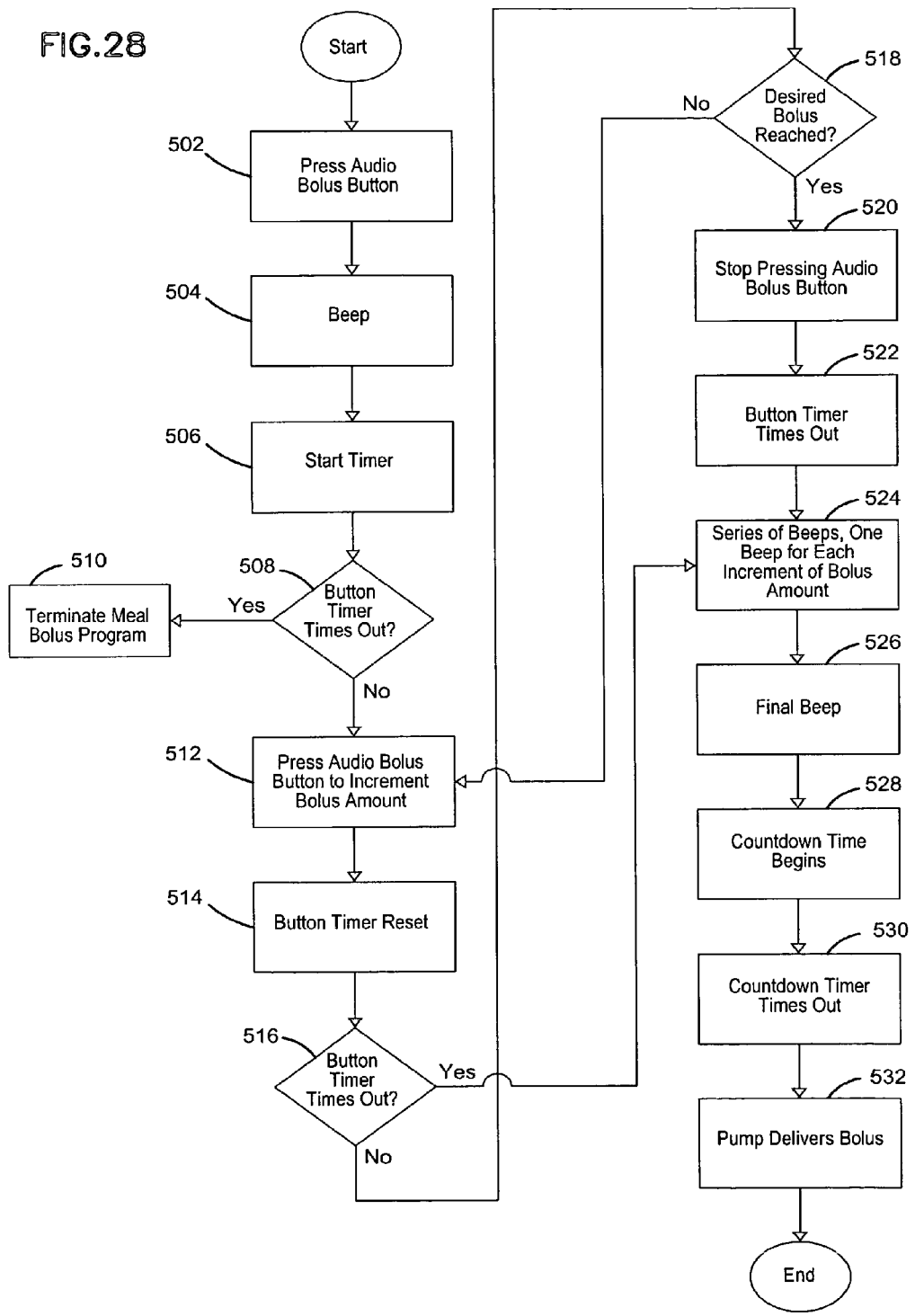
FIG. 28 illustrates the operations of setting and delivering an audio bolus on the pump shown in FIGS. 1 and 2.

Referring to FIG. 28, if audio bolus delivery is enabled, the user can program delivery of a standard meal bolus using a single button. To program an audio bolus, the user presses 502 the audio bolus button 125 once and the pump 100 begins the program for delivering a standard meal bolus. The pump 100 then generates an audible signal 504 in the form of a beep and starts a button-detection timer 506. In an alternative embodiment, the pump 100 does not generate the audible signal 504 and starts the button-detection timer 506 immediately upon initially pressing the audio bolus button 502.

The user then presses 512 the audio bolus button again to increment the amount to be delivered starting from 0. The user stops pressing the audible bolus button 125 when the desired bolus amount is reached 518 and 520. The amount of the increment is the increment size the user set when personalizing the meal bolus program. Each time the audio bolus button is pressed, the amount of the bolus increases by one increment.

The button-detection timer is reset 514 every time the audible bolus button is pressed. If the audible bolus button 125 is not pressed before the button-detection timer times out after the first time the audible bolus button 125 is pressed, the pump 100 cancels 510 the programming sequence. If the button-detection timer times out 516 while the user is incrementing the bolus amount, the pump 100 determines that the proper bolus amount is set. The audio alarm 108 then generates a series of beeps 524 that includes one beep for each bolus increment that was entered. This series of beeps provides an audible confirmation regarding the amount of the meal bolus.

In one possible embodiment, after the last beep in the series of beeps, the pump 100 generates a final beep 526 to signal the end of the series. The final beep 526 has a different tone or volume than the beeps in the series of beeps 524. In an alternative embodiment, the pump 100 does not generate the final beep 524.

If the amount of the bolus is correct, the user presses the audio bolus button 125 again and the meal bolus program starts a countdown timer 528, which gives the user time to cancel delivery of the bolus. When the countdown timer times out 530, the pump 100 delivers 532 the meal bolus.

In an example, if the increment count is set at 0.5 units and the user desires to program a standard meal bolus of 2 units, the user would press the audio bolus once to initiate programming the standard meal bolus and then four more times to increment the bolus amount to 2 units. After the fourth button is pushed, the user pauses and the audible-button timer times out. The pump 100 then generates a series of four beeps to signal that the bolus amount was incremented four times and a final beep to signal completion of the series of beeps. The countdown time would then begin to run, and the pump 100 would deliver a meal bolus of 2 units when the countdown timer times out.

Additionally, the bolus is set in either units of insulin or grams of carbohydrates depending on whether the pump 100 is set for programming in units of insulin or grams of carbohydrates, respectively. If the pump is set to program meal boluses in units of insulin, then each increment using the meal bolus button increments the bolus amount in units of insulin. If the bolus is set in to program meal boluses in grams of carbohydrates, then each increment using the meal bolus button 125 increments the bolus amount in grams of carbohydrates.

In one possible embodiment, the pump 100 displays the user interface that corresponds to the programming step being performed. For example, the user interface for entering the bolus amount is displayed after the user initiates the Audible bolus function by pressing the audible bolus button a first time. The bolus amount is initially set at 0. Every time the user presses the audible bolus button 125 after the first time and before the audible-button timer times out, the bolus amount displayed in the user interface will increment one time. A confirmation banner 404 (FIG. 19) will be displayed while the series of confirmation beeps are generated, and the user interface displaying the countdown timer is displayed while the countdown timer is running Additionally, the Stop function is assigned to the first function key 138. The pump 100 delivers the bolus and returns to the home page 152 after the countdown timer times-out.

O. Computer-Pump Communication and Programming

In one possible embodiment, the pump 100 can communicate with a computer. The computer can upload information from the pump 100, including the historical information generated by and stored on the pump 100. The computer can archive the historical information and maintain a complete historical record about the pump 100. Additionally, the computer can generate various reports regarding use of the pump 100, including information about delivery rates, bolus amounts, and alarms. Additionally, the computer can operate a program that allows the user to enter operating parameters for the various delivery programs that are loaded on the pump 100 and to download those operating parameters to the pump 100. In yet another possible embodiment, the computer can be used to download delivery programs and software updates to the pump 100.

Figure 29:
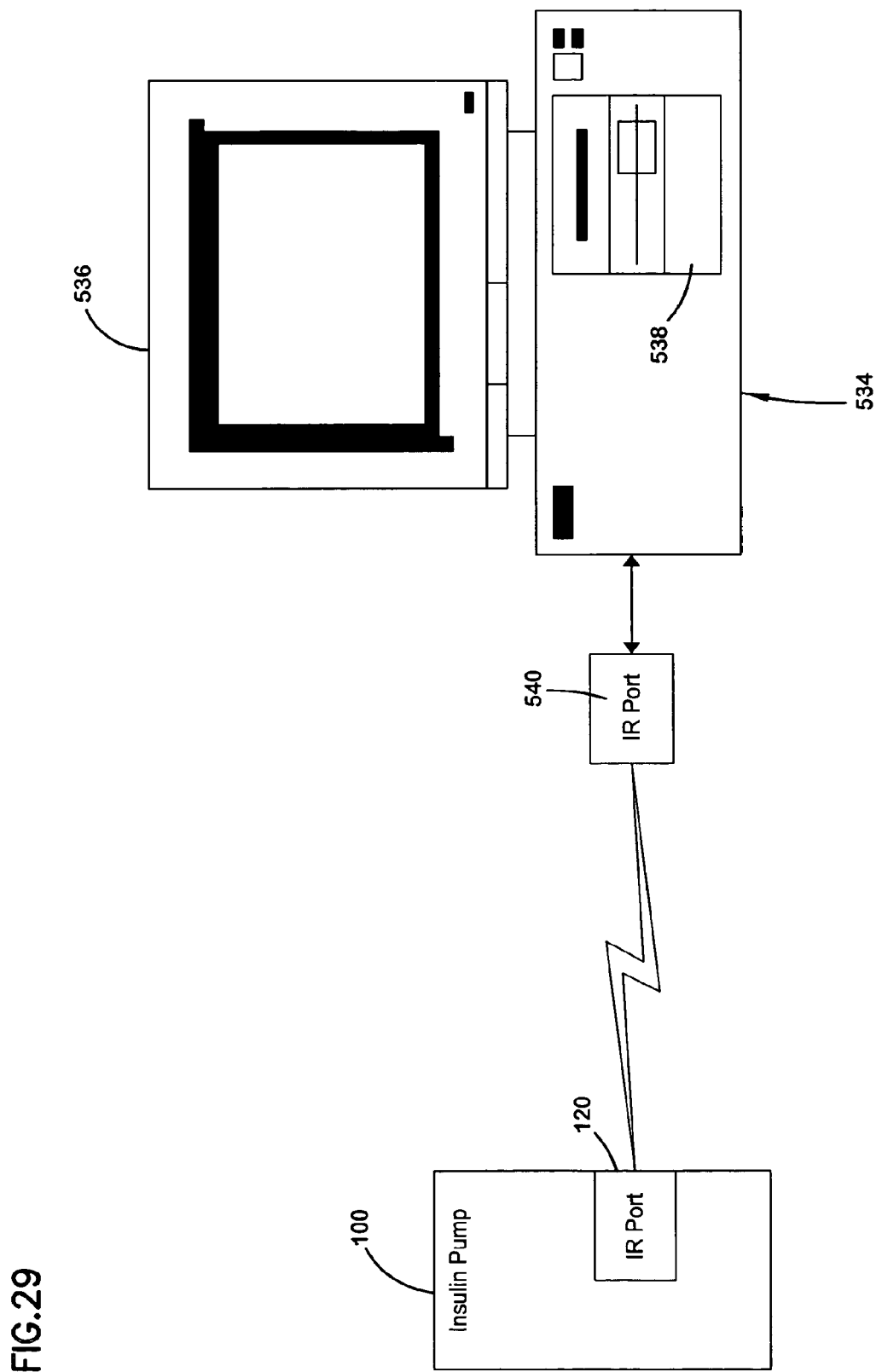
FIG. 29 illustrates the pump shown in FIGS. 1 and 2 communicating with a computer.

Referring to FIG. 29, in one possible embodiment, a computer 534 is a desktop computer that is IBM PC compatible, although other computers can be used. For example, the computer 534 could be an Apple computer, portable computer, a hand-held computer, a mainframe computer, a computer that is connected to a network. The computer 534 has a monitor 536, a storage device 538, and an infrared (IR) communication port 540. The pump 100 communicates with the computer through the IR port 120 on the pump 100 and the IR communication port 540 of the computer 534. In other embodiments, the pump 100 and computer 534 communicate through other types of data links such as a wireless or radio frequency (RF) connection or a wired connection such as USB, RS232, Fire wire, etc.

Communication between a medical pump and a computer is also discussed in U.S. Pat. No. 5,935,099, the disclosure of which was incorporated by reference above.

Referring to FIG. 30A, the software operating on the computer 534 generates a user interface 542 that allows a user to view, edit, and enter operating parameters for the various delivery programs that are loaded on the insulin pump 100. In one possible embodiment, the user interface 542 has a plurality of stacked primary windows 544a-544e. Each primary window includes a tab 546a-546e and data entry features for entering profile settings for the delivery programs. A basal programs primary window 544a is associated with the basal delivery programs, and is marked with a tab 546a bearing the name Basal Programs. A meal boluses primary window 544b is associated with the meal bolus delivery programs, and is marked with a tab 546b bearing the name Meal Boluses. A correction boluses primary window 544c is associated with the correction bolus deliver programs, and is marked with a tab 546c bearing the name Correction Boluses. A temporary rates primary window 544d is associated with the temporary rate delivery programs, and is marked with tab 546d bearing the name Temporary Rates.

A primary window 544 can include a variety of different data entry features for entering the operating parameters including text, numbers, flags, or the like. Examples of the data entry features include buttons, check boxes, spin boxes, text fields, numeric fields, and tables. The buttons and check boxes are alternatively set and cleared by clicking on them with a pointing device such as a mouse. Each spin box is associated with up and down buttons and contains a list of values. The user sets the desired value by spinning though the list of values with the up and down keys until the desired value is visible in the spin box. The tables have rows of cells and a scroll bar. The user can manipulate the scroll bar with a pointing device to scroll through the available rows within the table. Additionally, each primary window has a download button, an upload button, and a save button.

The primary window on the top of the stack is active, and the user can enter, edit, and view operating parameters in the active primary window. The user can bring any one of the primary windows to the top of the stack by clicking on the primary window's tab.

Still referring to FIG. 30A, the first primary window 544a, which is for setting the operating parameters for the basal programs, has three panels. The first panel 548 has a spin box 550 for setting the maximum basal rate for the insulin pump. The spin box 550 is displayed in a first group box 549. The user spins though available values until the desired maximum basal rate is visible within the spin box 550. The maximum basal rate set in the spin box will apply to all of the basal delivery programs. In the illustrated example, there are four possible basal delivery programs. The first spin box 550 is present in a first group box.

The second panel 552 of the screen has one secondary window 554a-554d for each of the basal delivery programs. The secondary windows are stacked and are marked with tabs 556a-556d. Each tab 556 is marked with the name of the basal program associated with the tab's secondary window 554. The secondary window 554 on the top of the stack is active, and the user can enter, edit, and view operating parameters in the active secondary window. The user clicks on the tab 556 for any given secondary window to bring it to the top of the stack. In the illustrated example, there are four basal delivery programs and hence four secondary windows named Basal 1 554a, Basal 2 554b, Basal 3 554c, and Basal 4 554d.

Each secondary window 554 has a button 558, a check box 560, and a text field 562 organized into a second group box 564 for setting program preferences. A table 566 and a graph 568 are organized into a third group box 570 and are for naming, setting, and viewing the basal delivery rates. To activate a basal delivery program, the user sets the button 558 by clicking on it. Any other basal program that was active becomes inactive and the button for the previously active basal delivery program is cleared. Additionally, an asterisk is placed in the tab 556 for the active basal delivery program so that the user can easily identify the active basal delivery program if the secondary window 554 for that basal delivery program is not on top of the stack. When the operating parameters for the basal delivery programs are downloaded to the pump 100, the basal delivery program in which the button 558 is set will become the active basal delivery program on the pump 100.

To display the basal delivery program as a menu item in the Basal Program submenu 318 (FIG. 13) on the pump 100, the user sets the checkbox 560. When the operating parameters for the basal programs are downloaded to the pump 100, the name for the basal program is displayed as a menu item in the Basal Program submenu 318.

To customize the name of the basal delivery program, the user types the custom name into the text field 562. The custom name is assigned to the basal delivery program and appears in the tab 556 for that program. Additionally, the custom name is the name downloaded into the pump 100 and appears in the Basal Program submenu 318, if the checkbox 560 is set. In an alternative embodiment, a spin box is associated with the text field 562. The spin box presents preprogrammed, optional names for the basal delivery programs that the user can select. The selected name would then replace the generic name (e.g., Basal 1, Basal 2, Basal 3, and Basal 4 in the illustrated example) for the program associated with the display. Examples of optional names that might be loaded in the pump 100 include weekday, weekend, sick, and monthly (which is to designate a basal delivery program set for a woman's menstrual cycle).

The basal rate table 566 or grid has a plurality of rows 572 and each row has two cells 574 and 576. When a cell within the table 566 has focus and the user presses the enter key or the tab key, the focus shifts to the next cell to the right. If the current cell is the last cell in the row, focus shifts to the first cell in the next row. If the user presses the enter key while the last cell in the last row is in focus, a new row is created. In this manner, the user can expand the length of the table 572. If the user presses the enter key while the last cell of a row is in focus and there is no data in any cell within that row, the computer will delete the row. The one exception is the first row in the table, which cannot be deleted.

The first cell within a row is a start-time cell 574, and the second cell within a row is a delivery-rate cell 576. Each row corresponds to a different interval in the delivery protocol for the basal delivery program. To set the delivery protocol for a basal program, the user enters the start time for each delivery interval in the start-time cell 574 and the delivery rate in the delivery-rate cell 576. The pump 100 will then deliver at the set delivery rate beginning at the set start time and until the start time for the next delivery interval. In one possible embodiment, the start time for the first interval is 12:00 midnight and cannot be changed.

Accordingly, to set the delivery protocol for the basal delivery program, the user types the start time in the start-time cell 574, hits the enter key and changes the focus to the delivery-rate cell 576 to the right. The user then types in the delivery rate for that interval, hits the cell key, and changes the focus to the start-time cell in the next row (creating the row if the next row does not already exist). A new row will appear in which the user can enter the operating parameters for another delivery interval. The user continues this process until the operating parameters for all of the desired intervals are entered into the table.

In an alternative embodiment, when a cell has focus, a spin box having up and down buttons is presented in that cell. The user can either type a value into the spin box or spin through values until a desired value is visible in the spin box. When the cell and hence the spin box loses focus, the visible value from the spin box is entered into the corresponding cell and the spin box becomes invisible.

The graph 568 provides a graphical illustration of the delivery rate for the basal delivery program over a 24-hour period. In one possible embodiment, the graph 568 is a bar chart illustrating the delivery rate in a resolution of 30 minutes. In the illustrated example, Basal 1 is set to deliver 2 units/hour from 12:00 midnight to 2:00 am, 2.5 units/hour from 2:00 am to 3:00 am, etc.

In one possible embodiment, the graph 568 is automatically updated as the user completes entering the start time and delivery rate for each delivery interval. Additionally, the total daily basal rate is displayed 578, and is automatically calculated and updated as the user completes entering the start time and delivery rate for each delivery interval. Entry of data for an interval is complete when the user enters the start time and delivery rate for the interval and exits both the start-time cell 574 and the delivery-rate cell 576.

The third panel 580 presents instructions to the user. In one possible embodiment, the user interface presents a help label 582 (e.g., the question mark in the illustrated example) in each of the group boxes 549, 564, and 570. When the user clicks on a help label 582, instructions specific to the group box or other aspects of the user interface associated with the help label are presented in the third panel. Alternatively, the user can point to a particular aspect of the user interface and right click on the mouse to present field-specific instructions in the third panel.

Figure 30B:
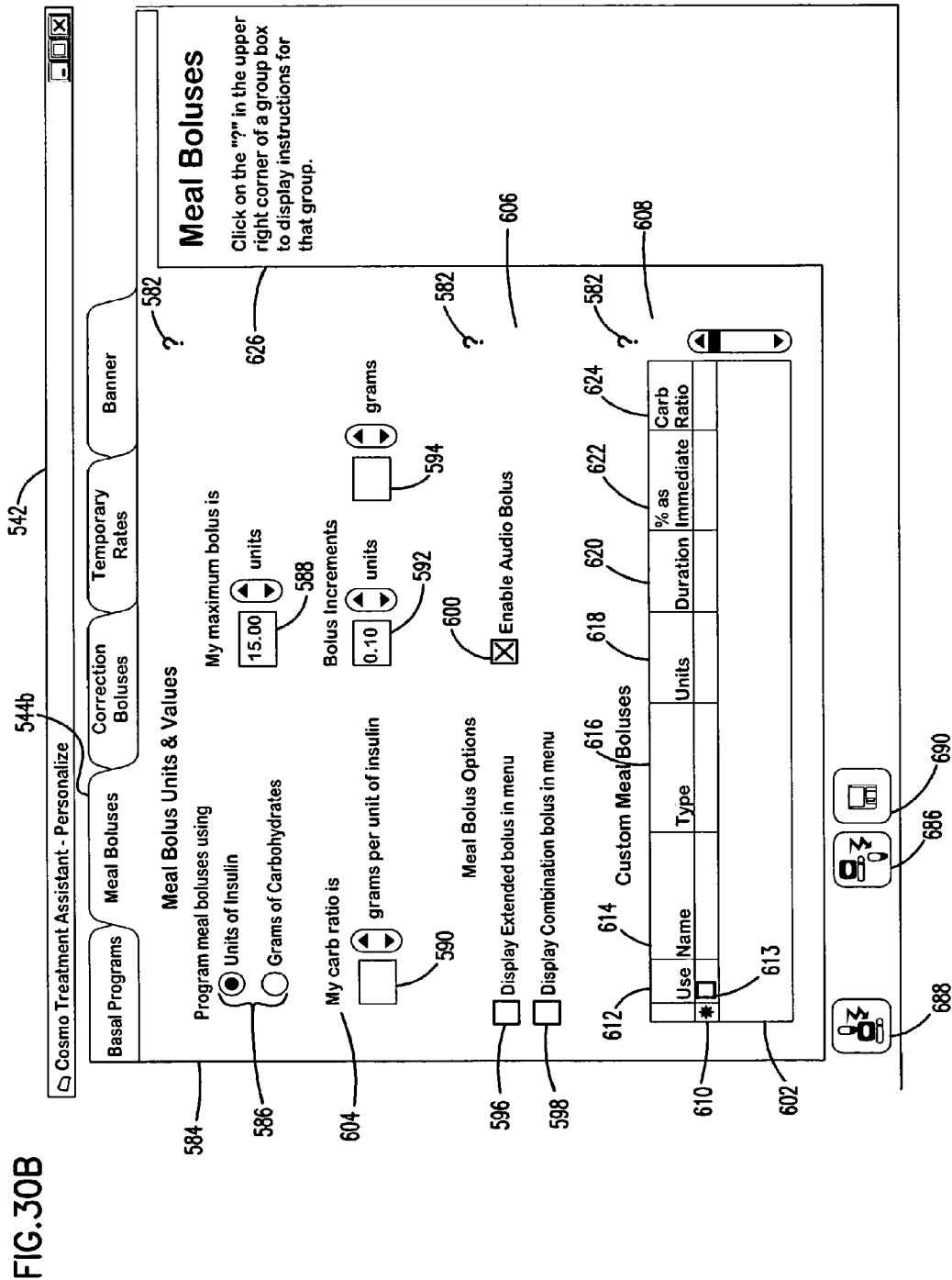

FIG. 30B illustrates the second primary window 544b, which is for setting the operating parameters of the meal bolus delivery programs. The meal bolus primary window includes two panels. The first panel 584 has a pair buttons 586, a first spin box 588, a second spin box 590, a third spin box 592, a fourth spin box 594, a first check box 596, a second check box 598, a third check box 600, and a meal bolus table 602.

The pair of buttons 586 and spin boxes 588, 590, 592, and 594 are present in a first group box 604, the check boxes 596, 598, and 600 are presented in a second group box 606, and the table 602 is present in a third group box 608. The pair of buttons 586 is for setting the meal bolus delivery program to use either units of insulin or grams of carbohydrates. The pair of buttons 586 toggle between set and cleared states so that when one is set the other cleared. The user set the first button to program the meal bolus programs in units of insulin and sets the second button to program the meal bolus programs in grams of carbohydrates The first spin box 588 is for setting the maximum bolus that the pump 100 can deliver when executing the meal bolus program. The second spin box 590 is for setting the users carbohydrate ratio. The third spin box 592 is for programming in units of insulin and is for setting the increments at which a user can spin through bolus amounts. The fourth spin box 594 is for programming in grams of carbohydrates and is for setting the increments at which a user can spin through grams of carbohydrates to be consumed in a meal.

When the user sets the first button for programming in units of insulin, the third spin box 592 is enabled, and the second 590 and fourth 594 spin boxes are disabled. When the user sets the second button for programming in grams of carbohydrates, the second 590 and fourth 594 spin boxes are enabled, and the third spin box 592 is disabled.

To enable the extended bolus program, the user sets the first check box 596. To enable the combination bolus program, the user sets the second check box 598. To enable the audio bolus function, the user sets the third check box 600.

The custom meal bolus table 602 has a plurality of rows 610, each row has a plurality of cells. The user navigates through the meal bolus table 602 using procedures substantially similar to that of the basal rate table. Also similar to the basal rate table, the custom meal bolus table 602 can have various spin boxes that become visible when a cell has focus. The spin boxes are for entering values and pre-typed text into the cell with which it is associated.

Within the meal bolus table 602, each row has seven cells. The first cell 612 has a check box 613. To enable the custom meal bolus defined by that row, the user sets the check box 613. The second cell 614 has a text field in which the user types a name to identify the custom meal bolus defined by that row. An example includes pizza, when the operating parameters for the custom meal bolus are customized to deliver insulin for working against a meal of pizza. Other examples, might include breakfast, lunch, dinner, snack, or any other specific type of food, drink, or meal.

The third cell 616 contain a text field for entering the type of custom meal bolus, whether it is a standard bolus, an extend bolus, or a combination bolus. In one possible embodiment, a spin box is presented in the third cell 616 when focus is placed on the cell. The user can then spin through the types of bolus (e.g., standard, extended, or combination) and set the desired type. The fourth cell 618 is a numeric field for entering the number of units to be delivered by the bolus program defined by that row. The fifth cell 620 is a time field in which the user enters the duration of the bolus delivery if the bolus program defined by that row is an extended bolus or a combination bolus. The sixth cell 622 is a numeric field in which the user enters the percent of the bolus to be delivered immediately if the bolus program defined by that row is a combination bolus.

The seventh cell 624 is a numeric field in which the user enters the carbohydrate ratio the pump 100 is to use when calculating the bolus amount to deliver. The seventh cell 624 allows the user to enter a customized carbohydrate ratio independent of the value set in the second spin box 590. For example, a user might use one carbohydrate for a custom meal bolus to be delivered before an early morning breakfast and a different carbohydrate ratio for a custom meal bolus to be delivered before an evening dinner or snack.

If the type of meal bolus set in the third cell (Type of Meal Bolus) 616 is standard, the fifth cell (Duration) 620 and sixth cell (% as Immediate) 622 are disabled and cleared. If the type of meal bolus set in the third cell 616 is an extended bolus, the fifth cell 620 is enabled and the sixth cell 622 is disabled and cleared. If the type of meal bolus set in the third cell 616 is set as a combination bolus, the fifth 620 and sixth 622 cells are enabled.

Additionally, because a meal bolus delivery program execute operating parameters that are in either units of insulin or grams of carbohydrate, any given row 610 in the meal bolus table 602 can accept a value in either the fourth cell 618 for units of insulin or the seventh cell 624 for the carbohydrate ratio. If the fourth cell 618 is populated with a value, the seventh cell 624 is disabled. If the seventh cell 624 is populated with a value, the fourth cell 618 is disabled. In one possible embodiment, when the user sets the first button for programming in units of insulin, the check box 613 is set in the first cell 612 for each row 610 in which there is a units of insulin value in the fourth cell 618. The check box 613 in the first cell 612 is cleared for each row 610 in which there is a carbohydrate value in the seventh cell 624. Similarly, when the user sets the second button for programming in grams of carbohydrates, the check box 613 is set in the first cell 612 for each row 610 in which there is a carbohydrate value in the seventh cell 624. The check box 613 in the first cell 612 is cleared for each row 610 in which there is a units of insulin value in the fourth cell 618.

The second panel 626 in the primary window 544b for the meal bolus delivery programs presents instructions. It operates in a manner substantially similar to the third, instruction panel 580 in the first primary window 544a for the basal rate delivery programs as described above.

Figure 30C:
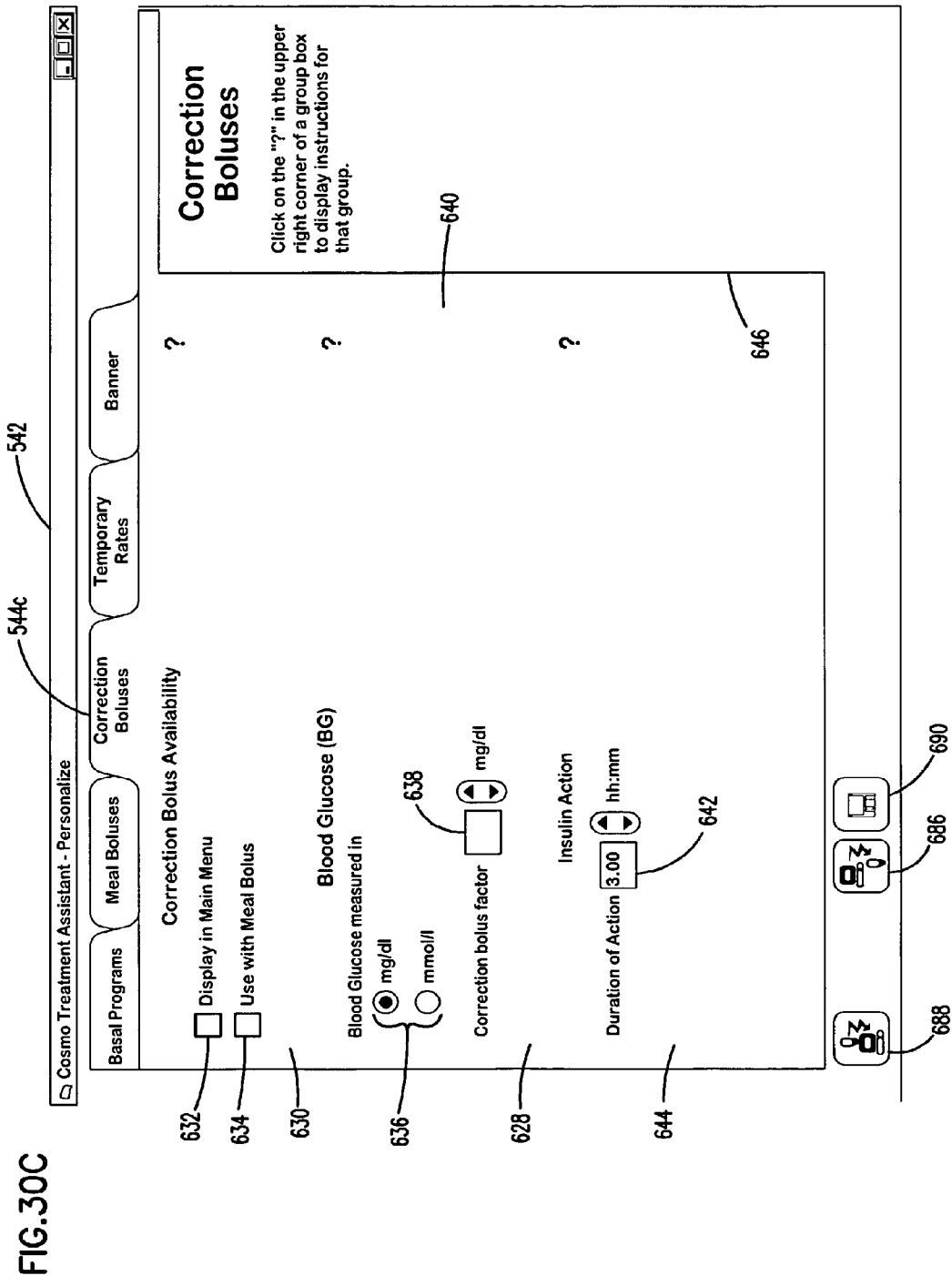

FIG. 30C illustrates the third primary window 544c, which is for setting the operating parameters for the correction bolus delivery program. The primary window 544c contains two panels. The first panel 628 has buttons, check boxes, and spin boxes. A first group box 630 in the first panel 628 has first and second check boxes 632 and 634. To control the pump 100 to make the correction bolus delivery program available through the main menu 190 and to display a correction bolus menu item in the main menu 190, the first check box 632 is set. To make the correction bolus program available through the meal bolus delivery programs described above, the second check box 634 is set.

A pair of buttons 636 set the units for the operating parameters used by the correction bolus program. The pair of buttons 636 toggle between set and cleared states so that when one is set the other is cleared. The first button is set to use mg/dL and the second button is set to use mmol/l. A first spin box 638 is for setting the correction bolus factor. When the first spin box 638 is in focus, the user spins through value until the desired correction factor is set. The pair of buttons 636 and the first spin box 638 are organized into a second group box 640.

A second spin box 642 is for setting the duration of activity or action for the insulin. As discussed above, the duration of activity is the length of time that each bolus remains working in the user's body. To enter the duration of activity, the user spins through values in the second spin box 642 until the desired value is set. The second spin box 642 is in a third group box 644.

The second panel 646 in the primary window 544c for the correction bolus delivery program presents instructions. It operates in a manner substantially similar to the third, instruction panel 580 in the first primary window 544a for the basal rate delivery programs as described above.

Figure 30D:
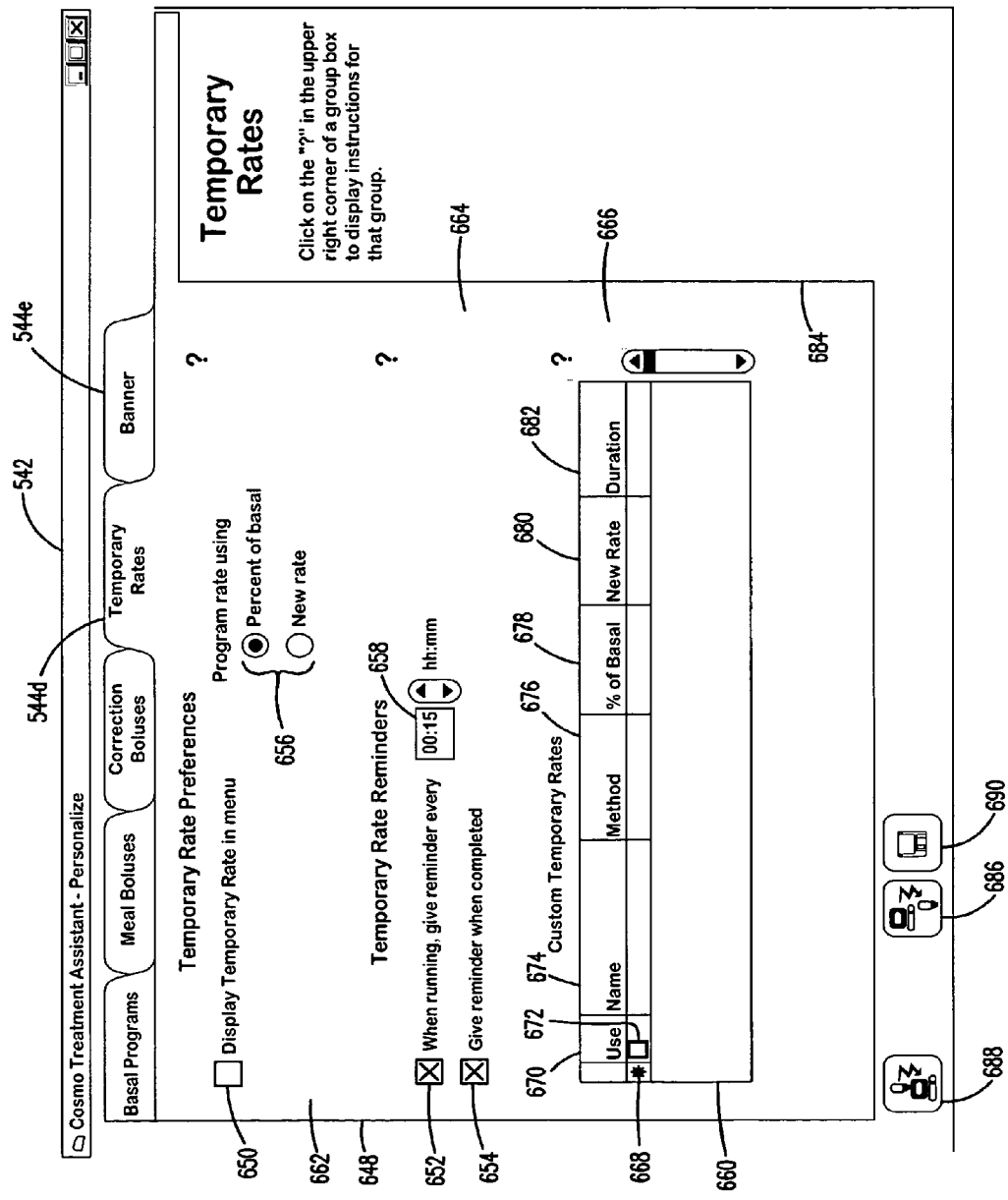

FIG. 30D illustrates the fourth primary window 544d, which is for setting operating parameters for the temporary rate programs. The primary window 544d has two panels. The first panel 648 has a first check box 650, a second check box 652, a third check box 654, a pair of buttons 656, a spin box 658, and a temporary rate table 660. The first check box 650 and pair of buttons 656 are in a first group box 662. The second 652 and third 654 check boxes and the spin box 658 are in a second group box 664. The table 660 is in a third group box 666.

The pair of buttons 656 sets the temporary rate either as a percentage of the running basal rate or as a new temporary basal rate. The pair of buttons 656 toggle between set and cleared states so that when one button is set the other button is cleared. The user sets the first button to set the temporary rate as a percent of the basal rate. The user sets the second button to set the temporary rate as a new, temporary basal rate.

To set a reminder so that the pump 100 intermittently generates a reminder (audible and/or vibratory) while the temporary rate program is running, the user sets the second check box 652. When the second check box 652 is set, the spin box 658 is enabled. The spin box 658 is for setting the interval between reminders. The spin box 658 is disabled when the second check box 652 is cleared. To set the pump 100 to generate a final reminder upon completion of the temporary rate, the user sets the third check box 654.

The temporary rate table 660 has a plurality of rows 668, and each row 668 contains a plurality of cells. The user navigates through the temporary rate table 660 using procedures substantially similar to that of the basal rate table. Also similar to the basal rate table 602, the temporary rate table 660 can have various spin boxes that become visible when a cell has focus. The spin boxes are for entering values and pretyped text into the cell with which it is associated.

Within the temporary rate table 660, each row has six cells. The first cell 670 has a check box 672. To enable the temporary rate defined by that row, the user sets the check box 672. The second cell 674 has a text field in which the user types a name to identify the temporary rate defined by that row. Examples might include exercise, 5-mile run, sick, evening, and the like. The third cell 676 is a text field to set the temporary rate to be programmed as a percent of current basal rate or as a new rate. In one possible embodiment a spin is present in the third cell 676 when focus is place on the cell. The user can then spin box through the types of temporary rates (e.g., % of Basal or New Rate) and set the desired type.

The fourth cell 678 is for assigning the percentage of the running basal rate to set as the temporary rate. The fifth cell 680 is for setting a new rate for the temporary rate. When the user enters % of basal in the third cell 676, the fourth cell 678 is enabled and the fifth cell 680 is disabled. When the user enters New Rate in the third cell 676, the fourth cell 678 is disabled, and the fifth cell 680 is enabled. The sixth cell 682 is for setting the duration of the temporary rate.

Additionally, in one possible embodiment, when the user sets the first button to adjust the delivery rate as a percent of the basal rate, the check box 672 is set in the first cell 670 for each row 668 in which there is a percentage in the fourth cell 678. The check box 672 in the first cell 670 is cleared for each row 668 in which there is a delivery rate value in the fifth cell 680. Similarly, when the user sets the second button to use a new delivery rate, the check box 672 is set in the first cell 670 for each row 668 in which there is a delivery rate value in the fifth cell 680. The check box 672 in the first cell 670 is cleared for each row 668 in which there is a percentage value in the fourth cell 678.

The second panel 684 in the primary window 544d for the temporary rate delivery programs presents instructions. It operates in a manner substantially similar to the third, instruction panel 580 in the first primary window 544a for the basal rate delivery programs as described above.

In addition to operating parameters, one possible embodiment of the user interface 542 also enables a user to view, edit, and enter other data, character strings, and settings that are loaded on the insulin pump 100.

Figure 30E:
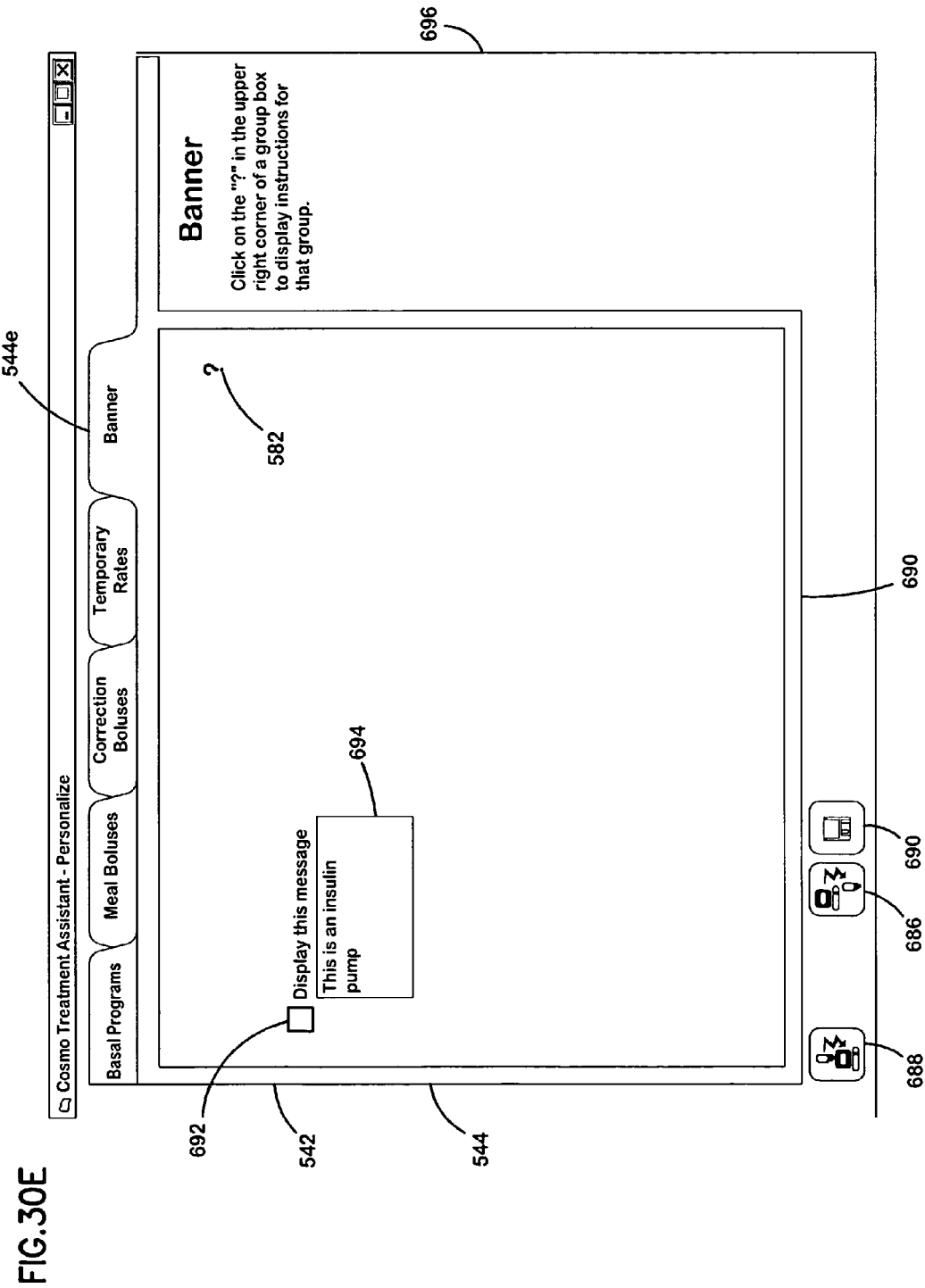

For example, FIG. 30E illustrates the fifth primary window 544e, which is for setting the banner displayed in the home page 152 of the pump 100. Primary window 544e is in the stack of primary windows 544. The fifth primary window 544e includes two panels. The first panel 690 has a field check box 692 and a text field 694 mated to the checkbox 692. To enter text into the home page 152, the user sets the checkbox 692 and enters text (numbers and letters as desired) into the text field 694. If the pump 100 includes multiple home pages 152 through which the user can scroll, an embodiment of the primary window 544e includes a checkbox 692 and mating text field 694 for each of the home pages 152. The user can then designate certain text for a particular home page 152 by setting the checkbox 692 associated with that home page 152 and entering text into the mating text field 694. In an alternative embodiment, if the text in the text field 694 is too long to fit into one display, the pump 100 automatically generates multiple home pages 152 through which the user can scroll and divides the text from the text field 694 between the multiple home pages 152. In another embodiment, similar text fields and associated checkboxes can be used to customize displays and messages for particular alarms, alerts, and reminders.

The second panel 696 in the primary window 544e presents instructions. It operates in a manner substantially similar to the third, instruction panel 580 in the first primary window 544a for the basal rate delivery programs as described above.

Yet other embodiments of the user interface 542 include various windows, buttons, checkboxes, spin boxes, and fields for setting other parameters used to operate the pump 100. Examples of such other parameters that can be set through the user interface 542 include various format settings, alarms, reminders, operating limits, report formats, security settings, character strings, and indeed any other operating parameters, data, settings, and character strings that can be programmed into the pump 100.

Referring to FIGS. 30A-30E, to download the operating parameters displayed in an active primary window 544, the user clicks on the download button 686. The operating parameters relating to the active primary windows are then downloaded into the pump 100 over the communication link. The pump 100 returns the downloaded operating parameters to the computer 534, which compares the returned operating parameters to the sent operating parameters. If the returned and sent operating parameters match, the computer 534 sends a handshake signal to the pump 100 and the microprocessor 102 maps each of the downloaded operating parameters to its designated memory addresses in RAM 116 and saves the downloaded operating parameters in RAM 116. If the returned and sent operating parameters do not match, the computer 534 generates an error signal and sends the error signal to the pump 100. The pump 100 then discards the downloaded operating parameters and preserves the preexisting operating parameters already stored in RAM 116.

To upload operating parameters from the pump 100 into the active primary window 544, the user clicks the upload button 688. The profile settings in RAM 116 that correspond to the active primary window 544 are then retrieved from RAM 116 on the pump 100 and are sent to the computer 534. The uploaded operating parameters are then populated into the fields of the active primary window 544, including all secondary windows 554. To save the profile settings, the user clicks the save button 690. The profile settings that populate the active primary window 544 then are saved in the storage device 538. In one possible embodiment, the name of the file that includes the saved data is the name of the pump user.

Furthermore, the user interface 542 can be used on the computer 534 to program and manage pumps 100 for several different pump users. In one such embodiment, the computer 534 is programmed with an initial interface that includes a text field in which the name of the pump user is entered either through the computer keyboard or through a spin box. Upon entering the name of the pump user, the computer 534 populates the data saved for that pump user's pump 100 into the user interface 542. In an alternative embodiment, the computer 534 is loaded with a menu in which the name of each pump user having stored data is included as a menu item. Selecting the name/menu item causes the computer 534 to populate the user interface 542 with data.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

The invention claimed is:

1. A method of operating a medical infusion pump, the method comprising:
receiving at the pump a selection of a type of alert from a plurality of types of alerts;
receiving at the pump through a user interface of the pump a predetermined interval of time associated with the selected alert;
associating a predetermined event relating to operation of the medical infusion pump with the selected alert; and
generating an alarm signal as the alert based on the predetermined event relative to the interval of time.

2. The method of claim 1 wherein receiving at the pump a predetermined interval of time includes receiving at the pump through the user interface an end time for the interval.

3. The method of claim 2 wherein receiving at the pump a predetermined interval of time further includes receiving at the pump through the user interface a start time for the interval.

4. The method of claim 1, wherein the selected type of alert can be selectively enabled or disabled and the alarm signal is only generated if the alert is enabled, and wherein the selected type of alert is stored in a memory of the pump when the alert is disabled.

5. The method of claim 1, further comprising:
receiving at the pump a selection of a second type of alert from the plurality of types of alerts, the second type of alert being different from the first type of alert;
receiving at the pump through the user interface a second predetermined interval of time associated with the second selected alert;
associating a second predetermined event relating to operation of the medical infusion pump with the second type of alert, the second predetermined event being different from the first predetermined event; and
generating an alarm signal as the second alert based on the second predetermined event relative to the second interval of time.

6. The method of claim 1, wherein generating an alarm signal as the alert based on the predetermined event relative to the interval includes generating the alarm signal an amount of time equal to a length of the interval of time after an occurrence of the predetermined event.

7. The method of claim 6, wherein the type of alert is a glucose reminder and generating an alarm signal includes generating a reminder to check a blood glucose level.

8. The method of claim 7, wherein the predetermined event is selected from the group consisting of: loading a Previously Presented cartridge into the pump and administering a meal bolus with the pump.

9. The method of claim 6, wherein the type of alert is a display-site reminder and the predetermined event is changing an infusion set of the pump.

10. The method of claim 1, wherein generating an alarm signal as the alert based on the predetermined event relative to the interval includes generating the alarm signal if there is no occurrence of the predetermined event within the interval of time.

11. The method of claim 10 wherein the type of alert is a missed meal bolus alert and the predetermined event is delivery of a meal bolus.

12. The method of claim 10, wherein the type of alert is an automatic off alert and the predetermined event is pressing of a button on the pump and generating an alarm signal includes a notification that the pump has automatically been shut off.

13. The method of claim 1, where the types of alerts are distinguished from each other due to at least some of the types of alerts being associated with different types of predetermined events than other types of alerts.

14. A medical infusion pump for delivering a therapeutic agent to a user, the pump comprising:
a pump mechanism, an alarm, and a timer;
an alarm program module in data communication with the alarm and the timer, the alarm program module programmed to operate a plurality of types of alerts and to associate a predetermined interval of time and a predetermined event relating to operation of the medical infusion pump with a selected type of alert, and wherein the alarm program module is programmed to generate an alarm signal as the alert based on the predetermined event relative to the interval.

15. The pump of claim 14, wherein the alarm program module is programmed to receive an end time for the interval.

16. The pump of claim 15, wherein the alarm program module is programmed to receive a start time for the interval.

17. The pump of claim 14, wherein the alarm program module is further programmed to permit each type of alert to be selectively enabled or disabled and wherein when an alert is disabled the alert is stored in a memory of the pump.

18. The pump of claim 14, wherein the alarm program module is further programmed to associate a second predetermined interval of time and a second predetermined event relating to operation of the medical infusion pump with a second selected type of alert, and wherein the alarm program module is programmed to generate an alarm signal as the second alert based on the second predetermined event relative to the second interval.

19. The pump of claim 14, where the types of alerts are distinguished from each other due to at least some of the types of alerts being associated with different types of predetermined events than other types of alerts.

20. The pump of claim 14, wherein the alarm program module is programmed to generate the alarm signal an amount of time equal to the length of the interval of time after the occurrence of the predetermined event.

21. The pump of claim 20, wherein the type of alert is a glucose reminder and the alarm signal includes a reminder to check a blood glucose level.

22. The pump of claim 21, wherein the predetermined event is selected from the group consisting of: loading a Previously Presented cartridge into the pump and administering a meal bolus with the pump.

23. The pump of claim 20, wherein the type of alert is a display-site reminder and the predetermined event is changing an infusion set of the pump.

24. The pump of claim 14, wherein the alarm program module is programmed to generate the alarm signal if there is no occurrence of the predetermined event within the interval of time.

25. The pump of claim 24, further comprising a meal bolus module programmed to control the pump mechanism to deliver a meal bolus, and wherein the type of alert is a missed meal bolus alert and the predetermined event is delivery of a meal bolus.

26. The pump of claim 24, wherein the type of alert is an automatic off alert and the predetermined event is pressing of a button on the pump and the alarm program module is programmed to generate an alarm signal indicating that the pump has automatically been shut off.

* * * * *